US011512315B2

(12) United States Patent
Sathyanarayanan et al.

(10) Patent No.: US 11,512,315 B2
(45) Date of Patent: Nov. 29, 2022

(54) METHODS AND COMPOSITIONS FOR MACROPHAGE POLARIZATION

(71) Applicant: CODIAK BIOSCIENCES, INC., Cambridge, MA (US)

(72) Inventors: Sriram Sathyanarayanan, Lexington, MA (US); Douglas E. Williams, Boston, MA (US); Dalia Burzyn, Newton, MA (US); Adam Thomas Boutin, Cambridge, MA (US); Sushrut Kamerkar, Cambridge, MA (US)

(73) Assignee: CODIAK BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 16/969,511

(22) PCT Filed: Feb. 12, 2019

(86) PCT No.: PCT/US2019/017731
§ 371 (c)(1),
(2) Date: Aug. 12, 2020

(87) PCT Pub. No.: WO2019/157535
PCT Pub. Date: Aug. 15, 2019

(65) Prior Publication Data
US 2020/0407725 A1    Dec. 31, 2020

Related U.S. Application Data

(60) Provisional application No. 62/629,563, filed on Feb. 12, 2018.

(51) Int. Cl.
| *C12N 15/11* | (2006.01) |
| *C12N 15/113* | (2010.01) |
| *A61K 9/50* | (2006.01) |
| *A61K 45/06* | (2006.01) |

(52) U.S. Cl.
CPC ........ *C12N 15/1135* (2013.01); *A61K 9/5068* (2013.01); *C12N 15/113* (2013.01); *A61K 45/06* (2013.01); *C12N 2310/11* (2013.01); *C12N 2310/321* (2013.01); *C12N 2310/3515* (2013.01); *C12N 2320/32* (2013.01)

(58) Field of Classification Search
CPC .............. C12N 15/1135; C12N 15/113; C12N 2310/11; A61K 9/5068
See application file for complete search history.

(56) References Cited

U.S. PATENT DOCUMENTS

| 10,195,290 B1 | 2/2019 | Dooley et al. | |
| 2016/0243192 A1* | 8/2016 | Seeger | A61K 39/39558 |

FOREIGN PATENT DOCUMENTS

| WO | WO-2010115202 A2 * | 10/2010 | ............ C07H 21/02 |
| WO | WO-2014082083 A1 | 5/2014 | |
| WO | WO-2016201323 A1 | 12/2016 | |
| WO | WO-2017053722 A1 | 3/2017 | |
| WO | WO-2017161010 A1 | 9/2017 | |
| WO | WO-2018039119 A1 | 3/2018 | |
| WO | WO-2019040920 A1 | 2/2019 | |
| WO | WO-2019157535 A1 | 8/2019 | |

OTHER PUBLICATIONS

Vickers et al., Efficient Reduction of Target RNAs by Small Interfering RNA and RNase H-dependent Antisense Agents, The Journal of Biological Chemistry, 2003, vol. 278, No. 9: 7108-7118 (Year: 2003).*
Ambros V., et al., "A Uniform System for Microma Annotation," RNA 9(3):277-279, Cold Spring Harbor Laboratory Press, United states (Mar. 2003).
Aranda F., et al., "Trial Watch: Immunostimulatory Monoclonal Antibodies in Cancer Therapy," Oncoimmunology 3(1):e27297, Landes Bioscience, United states (Jan. 2014).
Bacchetti S. and Graham F.L., "Transfer of the Gene for Thymidine Kinase to Thymidine Kinase-deficient Human Cells by Purified Herpes Simplex Viral Dna," Proceedings of the National Academy of Sciences 74(4):1590-1594, (May 1977).
Bartel D.P., "MicroRNAs: Genomics, Biogenesis, Mechanism, and Function," Cell 116(2):281-297, Elsevier (Jan. 2004).
Cannarile M.A., et al., "Colony-stimulating Factor 1 Receptor (Csf1r) Inhibitors in Cancer Therapy," Journal for immunotherapy of cancer 5(1):53, BMJ Publishing Group Ltd, England (Jul. 2017).
Chalasani N., et al., "The Diagnosis and Management of Nonalcoholic Fatty Liver Disease: Practice Guidance From the American Association for the Study of Liver Diseases," Hepatology 67(1):328-357, Elsevier (Jan. 2018).
Child P., et al., "Acyl Selectivity in the Transfer of Molecular Species of Phosphatidylcholines From Human Erythrocytes," Biochimica et Biophysica Acta 812(2):321-332, Elsevier (Jan. 1985).
Cuccarese, M.F., et al., "Heterogeneity of Macrophage Infiltration and Therapeutic Response in Lung Carcinoma Revealed by 3d Organ Imaging," Nature Communications vol. 8:14293 (2017).
Elbashir, S.M., et al., "Duplexes of 21-nucleotide RNAs mediate RNA interference in cultured mammalian cells, Nature 411(6836):494-498, Nature Publishing Group, United States (2001).
Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).
Felgner P.L., et al., "Lipofection: a Highly Efficient, Lipid-mediated Dna-transfection Procedur," Proceedings of the National Academy of Sciences of the United States of America 84(21): 7413-7417, National Academy of Sciences, United states (Nov. 1987).

(Continued)

*Primary Examiner* — Ekaterina Poliakova-Georgantas
(74) *Attorney, Agent, or Firm* — Sterne, Kessler, Goldstein & Fox P.L.L.C.

(57) ABSTRACT

Disclosed herein are compositions and methods comprising extracellular vesicles comprising nucleic acid that target genes, leading to macrophage polarization of tumor associated macrophages. In certain embodiments, disclosed herein are methods and compositions for increasing macrophage polarization for the treatment of cancer.

9 Claims, 15 Drawing Sheets

Specification includes a Sequence Listing.

(56) References Cited

OTHER PUBLICATIONS

Funes S.C., et al., "Implications of Macrophage Polarization in Autoimmunity," Immunology 154(2):186-195, Blackwell Scientific Publications, England (Jun. 2018).
Furuta, Y., et al., "Favipiravir (T-705), a Novel Viral RNA Polymerase Inhibitor," Antiviral Research 100(2): 446-454, Elsevier B.V (Nov. 2013).
Gautier E.L., et al., "Gene-expression Profiles and Transcriptional Regulatory Pathways That Underlie the Identity and Diversity of Mouse Tissue Macrophages," Nature immunology 13(11):1118-1128, Nature America Inc, United states (Nov. 2012).
Goodchild J., et al., "Therapeutic Oligonucleotides," Methods in molecular biology 764:1-15, Humana Press,United states (2011).
Gross, T.J and Hunninghake, G.W., "Idiopathic PulmonaryFibrosis, "The New England Journal of Medicine345(7):517-525 MassachusettsMedical Society, United States (Aug. 2001).
Guerriero J.L., et al., "Class IIa Hdac Inhibition Reduces Breast Tumours and Metastases Through Anti-tumour Macrophages," Nature 543(7645):428-432, Macmillan Journals ltd, England (Mar. 2017) with Supplemental Information.
International search report and Written opinion for the application PCT/US2019/017731 dated Jul. 25, 2019, 19 pages.
Kahlert, C., et al., "Identification of Double-Stranded Genomic DNA Spanning all Chromosomes with Mutated Kras and P53 Dna in the Serum Exosomes of Patients with Pancreatic Cancer," Journal of Biological Chemistry 289(7):3869-3875, American Society for Biochemistry and Molecular Biology, United States (Feb. 2014).
Krausgruber T., et al., "Irf5 Promotes Inflammatory Macrophage Polarization and Th1-th17 Responses," Nature immunology 12(3):231-238, Nature America Inc, United states (Mar. 2011).
Lewis C.E., and Pollard J.W., "Distinct Role of Macrophages in Different Tumor Microenvironments," Cancer Research 66(2):605-612, Cancer research (Jan. 2006).
Liu Y.C., et al., "Macrophage Polarization in Inflammatory Diseases," International journal of biological sciences 10(5):520-529, Ivyspring International, Australia (May 2014).
Ma L., et al., "On the Classification of Long Non-coding Rnas," RNA biology 10(6):925-933, Landes Bioscience, United states (Jun. 2013).
Martinez F.O., and Gordon S., "The M1 and M2 Paradigm of Macrophage Activation: Time for Reassessment,"F1000prime reports 6:13, Faculty of 1000, England (Mar. 2014).
Mayo Clinic Staff., "Definition [of pulmonary fibrosis] Mayo Foundation for Medical Education and Research," Retrieved Jul. 26, 2014, available from the world wide at webmayoclinic.org/diseases-conditions/pulmonary-fibrosis/symptoms-causes/syc-20353690 , (Jul. 2014).
Mills C.D., et al., "M-1/m-2 Macrophages and the Th1/th2 Paradigm," Journal of immunology 164(12):6166-6173, American Association of Immunologists, United states (Jun. 2000).
Mosser, D.M and Edwards, J.M., "Exploring the Full Spectrum of Macrophage Activation," Nature reviews Immunology 8(12):958-969, Nature Publishing Group, England (Dec. 2008).
Murray P.J., et al., "Macrophage Activation and Polarization: Nomenclature and Experimental Guidelines," Immunity 41(1):14-20, Cell Press, United states (Jul. 2014).
Nakada Y., et al., "Antisense Oligonucleotides Specific to Mutated K-ras Genes Inhibit Invasiveness of Human Pancreatic Cancer Cell Lines," Pancreatology 1(4):314-319, Elsevier (2001).
Neumann E., et al., "Gene Transfer Into Mouse Lyoma Cells by Electroporation in High Electric Fields," The EMBO journal 1(7): 841-845, Wiley Blackwell, England (1982).
Paddison P. J., et al., "Short Hairpin Rnas (Shrnas) Induce Sequence-specific Silencing in Mammalian Cells," Genes & development 16(8):948-958, Cold Spring Harbor Laboratory Press, United states (Apr. 2002).

Papapetrou, P.U., et al.," Genetic Modification of Hematopoietic Stem Cells With Nonviral Systems: Past Progress and Future Prospects," Gene Therapy 12(Suppl 1):S118-S130, Nature Publishing Group, England(Oct. 2005).
Pardoll D.M., "The Blockade of Immune Checkpoints in Cancer Immunotherapy," Nature reviews Cancer 12(4):252-264, Nature Pub, England (Mar. 2012).
Patel S., and Player M.R., "Colony-stimulating Factor-1 Receptor Inhibitors for the Treatment of Cancer and Inflammatory Disease," Current topics in medicinal chemistry 9(7):599-610, Bentham Science Publishers, UAE (2009).
Petersen, M and Wengel, G., "LNA: a Versatile Tool forTherapeutics and Genomics," Trends in Biotechnology 21 (2):74-81, ElsevierScience Publishers, England (Feb. 2003).
Rejiba, S., et al., "K☐Ras Oncogene Silencing Strategy Reduces Tumor Growth and Enhances Gemcitabine Chemotherapy Efficacy for Pancreatic Cancer Treatment," Cancer Science 98(7):1128-1136, Japanese Cancer Association (Jul. 2007).
Rodell C.B., et al., "TLR7/8-agonist-loaded Nanoparticles Promote the Polarization of Tumour-associated Macrophages to Enhance Cancer Immunotherapy," Nature Biomedical Engineering 2:578-588, Springer Nature, England(2018).
Roszer T., "Understanding the Mysterious M2 Macrophage Through Activation Markers and Effector Mechanisms," Mediators of inflammation, 816460, Rapid Communications of Oxford Ltd, United states (2015).
Sambrook, J., et al., "Molecular Cloning: A Laboratory Manual," Second Edition, Cold Spring Harbor Laboratory Press, United States (1989).
Sau S., et al., "Multifunctional Nanoparticles for Cancer Immunotherapy: a Groundbreaking Approach for Reprogramming Malfunctioned Tumor Environment," Journal of Controlled Release 274:24-34, Elsevier (Mar. 2018).
Selvam C., et al., "Therapeutic Potential of Chemically Modified Sirna: Recent Trends," Chemical biology & drug design 90(5):665-678, Wiley-Blackwell, England (Nov. 2017).
Senti G., et al., "Intralymphatic Allergen Administration Renders Specific Immunotherapy Faster and Safer: a Randomized Controlled Trial," PNAS 105(46):17908-17912 (Apr. 2008).
Sharei A., et al., "A Vector-free Microfluidic Platform for Intracellular Delivery," Proceedings of the National Academy of Sciences 110(6):2082-2087, National Academy of Sciences, United States (Feb. 2013).
Sica A., et al., "Autocrine Production of IL-10 Mediates Defective IL-12 Production and NF-κB Activation in Tumor-Associated Macrophages," Journal of Immunology 164 (2):762-767, (Jan. 2000).
Sica A., et al., "Macrophage Polarization in Tumour Progression," Seminars in cancer biology 18(5):349-355, Academic Press, England (Oct. 2008).
Song Y., et al., "Ultrasound-mediated Dna Transfer for Bacteria," Nucleic acids research 35(19):e129, Oxford University Press, England (2007).
Storz P., "The Crosstalk Between Acinar Cells With Kras Mutations and M1-polarized Macrophages Leads to Initiation of Pancreatic Precancerous Lesions," Oncoimmunology 4(6): e1008794, Landes Bioscience, United states (Jun. 2015).
Su M.J., et al., "Pancreatic Cancer Cell Exosome-mediated Macrophage Reprogramming and the Role of Micrornas 155 and 125b2 Transfection Using Nanoparticle Delivery Systems," Scientific Reports, 6:30110, (Jul. 2016).
Summerton, J. and Weller, D., "Morpholino Antisense Oligomers: Design, Preparation, and Properties," Antisense & Nucleic Acid Drug Development 7(3):187-195, Mary Ann Liebert, Inc., United States (Jun. 1997).
Wang Q., et al., "Fra-1 Protooncogene Regulates Il-6 Expression in Macrophages and Promotes the Generation of M2d Macrophages," Cell Research 20(6):701-712, Nature Publishing Group, England(Jun. 2010).
Weiss B., et al., "Antisense Oligodeoxynucleotides and Antisense RNA : Novel Pharmacological and Therapeutic Agents," CRC-Press, 252 (1997).

(56) References Cited

OTHER PUBLICATIONS

Wynn T.A., et al., "Macrophage Biology in Development, Homeostasis and Disease," Nature 496(7446):445-455, Nature Publishing Group, England (Apr. 2013).

Xue J., et al., "Alternatively Activated Macrophages Promote Pancreatic Fibrosis in Chronic Pancreatitis," Nature Communications 6:7158 (May 2015).

Xue J., et al., "Transcriptome-based Network Analysis Reveals a Spectrum Model of Human Macrophage Activation," Immunity 40(2):274-288, Cell Press, United states (Feb. 2014).

Zeisberger, S.M., et al., "Clodronate-liposome-mediated Depletion of Tumour-associated Macrophages: a New and Highly Effective Antiangiogenic Therapy Approach," British Journal of Cancer 95(3):272-281, Nature Publishing Group on behalf of Cancer Research UK, England(Aug. 2006).

Zhang Y., et al., "Adipocyte-derived Microvesicles From Obese Mice Induce M1 Macrophage Phenotype Through Secreted Mir-155," Journal of Molecular Cell Biology 8(6):505-517, Chinese Academy of Sciences (Dec. 2016).

\* cited by examiner

Stat 3 (24h)

CD163 (48h)

US 11,512,315 B2

METHODS AND COMPOSITIONS FOR MACROPHAGE POLARIZATION

REFERENCE TO A SEQUENCE LISTING SUBMITTED ELECTRONICALLY VIA EFS-WEB

The instant application contains a Sequence Listing which has been submitted in ASCII format via EFS-Web, and is hereby incorporated by reference in its entirety. Said ASCII copy, created on Nov. 16, 2021, is named 4000_0190001_Seq_Listing.txt and is 1,878 bytes in size.

FIELD OF THE INVENTION

This invention relates to compositions and methods comprising extracellular vesicles harboring nucleic acid that target genes, leading to macrophage polarization of tumor associated macrophages.

BACKGROUND

Immunotherapy is the treatment of disease by inducing, enhancing, or suppressing the immune response. Cancer immunotherapy usually has fewer side effects than traditional cancer therapies, such as chemotherapy and radiation therapy. In one approach, cancer immunotherapy has been used to stimulate the patient's own macrophages to attack cancer cells. Macrophages display different phenotypes, e.g., they can be cancer-promoting or they can possess anti-cancer activity. The M2 phenotype, or "alternatively activated macrophages," typically exhibit cancer-promoting activities, such as the suppression of the immune system and the production of extracellular matrix- and tissue-remodeling activities. The M1 phenotype, or "classically activated macrophages," typically exhibit anti-cancer activities such as the phagocytosis of tumor cells and the stimulation of adaptive immunity so that tumor cells can be recognized and attacked. Improvements in immunomodulatory methods and compositions that promote macrophage polarization (i.e., conversion to the M1 phenotype) are needed.

SUMMARY

Aspects of the disclosure encompass an extracellular vesicle comprising one or more immunomodulating component(s) that, upon contact with a macrophage, selectively repolarizes the macrophage from an M2 to an M1 phenotype. In some aspects the disclosure encompasses an extracellular vesicle that is an exosome comprising one or more immunomodulating component(s) that, upon contact with a macrophage, selectively repolarizes the macrophage from an M2 to an M1 phenotype In some aspects, the extracellular vesicle, e.g., the exosome, comprises one or more immunomodulating component(s) that, upon contact with a macrophage, selectively repolarizes the macrophage from an M2 to an M1 phenotype, and the immunomodulating component(s) is a nucleic acid, e.g., an inhibitory RNA, e.g., an antisense RNA, an siRNA, an shRNA, a miRNA, a lncRNA, a pri-miRNA or a pre-miRNA, or, e.g., an antisense oligonucleotide (ASO) or, e.g., the immunomodulating component is an antisense oligonucleotide comprising a sequence at least 95% identical to a sequence selected from SEQ ID NOs:1-6.

In some aspects, the extracellular vesicle, e.g., the exosome, comprises one or more immunomodulating component(s) that, upon contact with a macrophage, selectively repolarizes the macrophage from an M2 to an M1 phenotype, and the immunomodulating (components), e.g., a nucleic acid, e.g., an inhibitory RNA, e.g., an antisense RNA, an siRNA, an shRNA, a miRNA, a lncRNA, a pri-miRNA or a pre-miRNA, or, e.g., an antisense oligonucleotide (ASO) or, e.g., the immunomodulating component is an antisense oligonucleotide comprising a sequence at least 95% identical to a sequence selected from SEQ ID NOs:1-6, inhibit(s) at least one macrophage target gene, e.g., at least one gene is selected from the group consisting of: KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, Glutaminase, CEBP/β, Pi3Kγ, and PKM2, e.g., STAT3, STAT6, CEBP/β, Pi3Kγ, KRAS, and HIF1-alpha, e.g., STAT3, e.g., KRAS.

In some aspects, the extracellular vesicle, e.g., the exosome, comprises one or more immunomodulating component(s) that, upon contact with a macrophage, selectively repolarizes the macrophage from an M2 to an M1 phenotype, and the immunomodulating component is an antisense oligonucleotide that targets STAT3.

In some aspects, the extracellular vesicle, e.g., the exosome, comprises one or more immunomodulating component(s) that, upon contact with a macrophage, selectively repolarizes the macrophage from an M2 to an M1 phenotype, and the immunomodulating component is an antisense oligonucleotide that targets KRAS.

In some aspects, the extracellular vesicle, e.g., the exosome, comprises one or more immunomodulating component(s) that, upon contact with a macrophage, selectively repolarizes the macrophage from an M2 to an M1 phenotype, and the immunomodulating component is an inhibitory RNA, e.g., an antisense RNA, an siRNA, an shRNA, a miRNA, a lncRNA, a pri-miRNA or a pre-miRNA that targets KRAS, e.g., wild-type human KRAS, or wild-type human KRAS and also mouse $KRAS^{G12D}$.

In any of the above-described aspects, the extracellular vesicle, e.g., the exosome, comprises one or more immunomodulating component(s), e.g., a nucleic acid, inhibitory RNA, antisense RNA, siRNA, an shRNA, a miRNA, a lncRNA, a pri-miRNA or a pre-miRNA, or an ASO that, upon contact with a macrophage, selectively repolarizes the macrophage from an M2 to an M1 phenotype, and the macrophage is a tumor- (e.g., pancreatic tumor) resident macrophage.

In any of the above-described aspects, the extracellular vesicle, e.g., the exosome, comprises one or more immunomodulating component(s), e.g., a nucleic acid, inhibitory RNA, antisense RNA, siRNA, an shRNA, a miRNA, a lncRNA, a pri-miRNA or a pre-miRNA, or an ASO that, upon contact with a macrophage, selectively repolarizes the macrophage from an M2 to an M1 phenotype, and further comprise an additional immunomodulating component, e.g., a small molecule drug, an antibody or active fragment thereof, e.g., an immune checkpoint inhibitor that binds to CTLA-4, PD-1, or PD-L1, or an inhibitor that binds to CSF1-R, or a therapeutic protein or active fragment thereof.

In any of the above-described aspects, the extracellular vesicle, e.g., the exosome, comprises one or more immunomodulating component(s), e.g., a nucleic acid, inhibitory RNA, antisense RNA, siRNA, an shRNA, a miRNA, a lncRNA, a pri-miRNA or a pre-miRNA, or an ASO that, upon contact with a macrophage, selectively repolarizes the macrophage from an M2 to an M1 phenotype, and further comprise an additional immunomodulating component, e.g., an antibody or active fragment thereof, e.g., an immune checkpoint inhibitor that binds to CTLA-4, PD-1, or PD-L1, or an inhibitor that binds to CSF1-R, wherein the antibody or active fragment thereof comprises CDRs that are at least 95% identical to the CDRs of Ipilimumab, or at least 95% identical to the CDRs of Nivolumab, or at least 95% identical to the CDRs of Cemiplimab, or at least 95% identical to the CDRs of Pembrolizumab, or at least 95% identical to the CDRs of Atezolizumab, or at least 95% identical to the CDRs of Avelumab, or at least 95% identical to the CDRs of Durvalumab, or at least 95% identical to the CDRs of Pexidartinib, or at least 95% identical to the CDRs of PLX7486, or at least 95% identical to the CDRs of ARRY-382, or at least 95% identical to the CDRs of JNJ-40346527, or at least 95% identical to the CDRs of BLZ945, or at least 95% identical to the CDRs of Emactuzumab, or at least 95% identical to the CDRs of AMG820, or at least 95% identical to the CDRs of IMC-CS4, or at least 95% identical to the CDRs of Cabiralizumab, or wherein the antibody or active fragment thereof is at least one antibody selected from the group consisting of Ipilimumab, Nivolumab, Cemiplimab, Pembrolizumab, Atezolizumab, Avelumab, Durvalumab, Pexidartinib, PLX7486, ARRY-382, JNJ-40346527, BLZ945, Emactuzumab, AMG820, IMC-CS4 and Cabiralizumab, or wherein the antibody or active fragment thereof is at least one antibody that competes for binding with antibody selected from the group consisting of Ipilimumab, Nivolumab, Cemiplimab, Pembrolizumab, Atezolizumab, Avelumab, Durvalumab, Pexidartinib, PLX7486, ARRY-382, JNJ-40346527, BLZ945, Emactuzumab, AMG820, IMC-CS4 and Cabiralizumab.

In any of the above-described aspects, wherein the extracellular vesicle, e.g., the exosome, comprises one or more immunomodulating component(s), e.g., a nucleic acid, inhibitory RNA, antisense RNA, siRNA, an shRNA, a miRNA, a lncRNA, a pri-miRNA or a pre-miRNA, or an ASO that, upon contact with a macrophage, selectively repolarizes the macrophage from an M2 to an M1 phenotype and further comprise an additional immunomodulating component, e.g., an antibody or active fragment thereof, e.g., an immune checkpoint inhibitor that binds to CTLA-4, PD-1, or PD-L1, or an inhibitor that binds to CSF1-R, wherein the antibody or active fragment thereof comprises CDRs that are at least 95% identical to the CDRs of Ipilimumab, or at least 95% identical to the CDRs of Nivolumab, or at least 95% identical to the CDRs of Cemiplimab, or at least 95% identical to the CDRs of Pembrolizumab, or at least 95% identical to the CDRs of Atezolizumab, or at least 95% identical to the CDRs of Avelumab, or at least 95% identical to the CDRs of Durvalumab, or at least 95% identical to the CDRs of Pexidartinib, or at least 95% identical to the CDRs of PLX7486, or at least 95% identical to the CDRs of ARRY-382, or at least 95% identical to the CDRs of JNJ-40346527, or at least 95% identical to the CDRs of BLZ945, or at least 95% identical to the CDRs of Emactuzumab, or at least 95% identical to the CDRs of AMG820, or at least 95% identical to the CDRs of IMC-CS4, or at least 95% identical to the CDRs of Cabiralizumab, or wherein the antibody or active fragment thereof is at least one antibody selected from the group consisting of Ipilimumab, Nivolumab, Cemiplimab, Pembrolizumab, Atezolizumab, Avelumab, Durvalumab, Pexidartinib, PLX7486, ARRY-382, JNJ-40346527, BLZ945, Emactuzumab, AMG820, IMC-CS4 and Cabiralizumab, or wherein the antibody or active fragment thereof is at least one antibody that competes for binding with antibody selected from the group consisting of Ipilimumab, Nivolumab, Cemiplimab, Pembrolizumab, Atezolizumab, Avelumab, Durvalumab, Pexidartinib, PLX7486, ARRY-382, JNJ-40346527, BLZ945, Emactuzumab, AMG820, IMC-CS4 and Cabiralizumab, it further comprises PTGFRN or a fragment thereof, and the antibody or fragment thereof may optionally be fused to the PTGFRN or the fragment thereof.

In any of the above-described aspects, the comparison is determined using an assay selected from the group consisting of an extracellular vesicle uptake assay, a target gene expression assay, a downstream gene expression assay, a cytokine release assay and a macrophage cell surface protein assay.

In any of the above-described aspects, the M2 macrophage is a tumor associated macrophage is a tumor associated macrophage selected from the group consisting of a M2a, M2b, and M2c macrophage.

In any of the above-described aspects, the M1 macrophage exhibits increased secretion of inflammatory cytokines and chemokines selected from the group consisting of INFγ, IL-12, IL-23, TNFα, IL-6, IL-1, CSCL9, CXCL10 and CXCL11 compared to the M2 macrophage prior to polarization, and/or exhibits decreased secretion of immunosuppressive cytokines and chemokines selected from the group consisting IL-10, TGFβ, PGE2, CCL2, CCL17, CCL18, CCL22 and CCL24 compared to the M2 macrophage prior to polarization, and/or expresses increased tumor associated antigen compared to the M2 macrophage prior to polarization, and/or increases stimulation of CD8$^+$ T-Cells and/or Natural Killer cells compared to the M2 macrophage prior to polarization.

In aspects, the disclosure encompasses a pharmaceutical composition comprising the extracellular vesicle, e.g., exosome, that comprises one or more immunomodulating component(s) that, upon contact with a macrophage, selectively repolarizes the macrophage from an M2 to an M1 phenotype.

In some aspects, the disclosure encompasses a method of treating a disease (e.g., cancer such as, e.g., pancreatic cancer) in a patient (e.g., a human) in need thereof, comprising administering (e.g., via a route selected from the group consisting of intravenous, intraperitoneal and intratumoral administration) the extracellular vesicle of any of the above-described aspects, e.g., the exosome that comprises one or more immunomodulating component(s) (e.g., an inhibitory RNA targeting a proto-oncogene (e.g., KRAS)) that, upon contact with a macrophage, selectively repolarizes the macrophage from an M2 to an M1 phenotype of any of the above-described aspects, or comprising administering a pharmaceutical composition comprising the extracellular vesicle of any of the above-described aspects, e.g., the exosome that comprises one or more immunomodulating component(s) that, upon contact with a macrophage, selectively repolarizes the macrophage from an M2 to an M1 phenotype of any of the above-described aspects.

In some aspects, the disclosure encompasses the methods of treatment described above and further comprises a second therapy, e.g., a surgical therapy, chemotherapy, radiation therapy, cryotherapy, hormonal therapy, or immunotherapy.

In some aspects, the disclosure encompasses methods of modulating gene expression in a macrophage comprising contacting the macrophage with an extracellular vesicle comprising one or more immunomodulating components that inhibit at least one gene and thereby increase macrophage polarization from an M2 to an M1 phenotype, as compared to contacting the macrophage with equimolar amount(s) of the immunomodulating components alone.

In some aspects, the methods of modulating gene expression in a macrophage comprising contacting the macrophage ex vivo or in vitro with an extracellular vesicle comprising one or more immunomodulating components that inhibit at least one gene and thereby increase macrophage polarization from an M2 to an M1 phenotype, as compared to contacting the macrophage with equimolar amount(s) of the immunomodulating components alone.

In some aspects, the methods of modulating gene expression in a macrophage comprising contacting the macrophage in vivo, with an extracellular vesicle (e.g., by administering the extracellular vesicle to a subject, e.g., a human subject, e.g., by a route selected from the group consisting of intravenous, intraperitoneal and intratumoral administration) comprising one or more immunomodulating components that inhibit at least one gene and thereby increase macrophage polarization from an M2 to an M1 phenotype, as compared to contacting the macrophage with equimolar amount(s) of the immunomodulating components alone.

In some aspects, the subject of the above-disclosed methods of modulating gene expression in a macrophage, is suffering from a condition selected from cancer (e.g., pancreatic cancer) and fibrosis In some aspects, the extracellular vesicle used in any of the above-disclosed methods of modulating gene expression in a macrophage is an exosome, and the immunomodulating component is a nucleic acid, e.g., an inhibitory RNA, such as, e.g., an antisense RNA, an siRNA, an shRNA, a miRNA, a lncRNA, a pri-miRNA or a pre-miRNA.

In some aspects, the extracellular vesicle used in any of the above-disclosed methods of modulating gene expression in a macrophage is an exosome, and the immunomodulating component is a nucleic acid, e.g., an ASO.

In some aspects, the extracellular vesicle used in any of the above-disclosed methods of modulating gene expression in a macrophage is an exosome, and the immunomodulating component is a nucleic acid, e.g., an antisense oligonucleotide comprising a sequence at least 95% identical to a sequence selected from SEQ ID NOs: 1-6 or an antisense oligonucleotide comprising a sequence selected from SEQ ID NOs: 1-6, and the at least one gene is selected from the group consisting of KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, Glutaminase, CEBP/β, Pi3Kγ, and PKM2, or from the group consisting of: STAT3, STAT6, CEBP/β, Pi3Kγ, KRAS, and HIF1-alpha, or is STAT3, or is KRAS, and if KRAS, the immunomodulatory component can optionally be an inhibitory RNA that targets wild-type human KRAS.

In some aspects, the disclosure provides a method of treating pancreatic cancer in a subject comprising: administering to the subject an extracellular vesicle comprising an inhibitory RNA targeting human wild-type KRAS; wherein the treatment increases the percentage of polarization of tumor-resident macrophages from an M2 to an M1 phenotype to a greater level than that observed in a patient treated with an inhibitory RNA targeting human $KRAS^{G12D}$.

In some aspects the disclosure provides the above-described method of treating pancreatic cancer in a subject, wherein the percentage of polarization of tumor-resident macrophages is determined using an ex-vivo assay of tumor-resident macrophages obtained from a tumor sample.

Provided herein are compositions and methods comprising extracellular vesicles selected, enriched, or engineered with one or more immunomodulating components that can modify the activity of macrophages, promoting switching of macrophages from the M2 to the M1 phenotype (macrophage polarization) and boosting the patient's immune system to fight cancer.

Accordingly, in a first aspect, provided herein is an extracellular vesicle comprising one or more immunomodulating components, e.g., nucleic acid molecules that inhibits at least one gene in a target cell. In certain embodiments the target cell is a macrophage and the gene inhibition increases macrophage polarization from the M2 to M1 phenotype as compared to an equimolar amount of the immunomodulating component(s) alone. In certain embodiments, the extracellular vesicle is an exosome. In certain embodiments, the nucleic acid is an inhibitory RNA. In certain embodiments, the inhibitory RNA is an antisense RNA, an siRNA, an shRNA, a miRNA, a lncRNA, a pri-miRNA or a pre-miRNA. In certain embodiments, the at least one gene is selected from the group consisting of: KRAS, HRAS, NRAS, HIF1-alpha, HIF1-beta, Sp1, P300, LKB1, AMPK, STAT3, STATE, n-MYC, c-MYC, HCAR1, A2AB, IDO, TDO, Arginase, Glutaminase, CEBP/β, Pi3Kγ, and PKM2. In certain embodiments, the gene is KRAS. In certain embodiments, the nucleic acid is an inhibitory RNA that targets wild-type human KRAS. In certain embodiments, the inhibitory RNA also targets mouse $Kras^{G12D}$. In certain embodiments, the macrophage is a tumor resident macrophage. In certain embodiments, the tumor is a pancreatic tumor. In certain embodiments, the extracellular vesicle further comprises an additional immunomodulating component. In certain embodiments, the additional immunomodulating component is a small molecule drug, an antibody or a therapeutic protein. In certain embodiments, the antibody is an immune checkpoint inhibitor. In certain aspects, provided herein is a pharmaceutical composition comprising any of the above mentioned extracellular vesicles.

In certain aspects, described herein is a method of treating a disease in a patient in need thereof comprising administering the extracellular vesicles or the pharmaceutical compositions described herein to the patient, thereby treating the disease in the patient. In certain embodiments, the disease is a cancer. In certain embodiments, the cancer is pancreatic cancer. In some embodiments, the disease is a fibrotic condition. In some embodiments, the fibrotic condition is lung fibrosis, liver fibrosis, or pancreatic fibrosis. In certain embodiments, the liver fibrosis is non-alcoholic steatohepatitis, or NASH. In certain embodiments, the patient is human. In certain embodiments, the nucleic acid is an inhibitory RNA targeting a proto-oncogene. In certain embodiments, the proto-oncogene is human KRAS. In certain embodiments, the cancer is pancreatic cancer. In certain embodiments, the methods further comprise performing at least a second therapy. In certain embodiments, the second therapy comprises a surgical therapy, chemotherapy, radiation therapy, cryotherapy, hormonal therapy, or immunotherapy.

In certain embodiments, the target cell M2 macrophage is a tumor associated macrophage selected from the group consisting of a M2a, M2b, and M2c macrophage. In certain embodiments, the M1 macrophage exhibits increased secretion of inflammatory cytokines and chemokines selected from the group consisting of INFγ, IL-12, IL-23, TNFα, IL-6, IL-1, CSCL9, CXCL10 and CXCL11 compared to the M2 macrophage prior to polarization. In certain embodiments, the M1 macrophage exhibits decreased secretion of immunosuppressive cytokines and chemokines selected from the group consisting IL-10, TGFβ, PGE2, CCL2, CCL17, CCL18, CCL22 and CCL24 compared to the M2 macrophage prior to polarization. In certain embodiments, the M1 macrophage expresses increased tumor associated antigen compared to the M2 macrophage prior to polarization. In certain embodiments, the M1 macrophage increases stimulation of CD8+ T-Cells and/or Natural Killer cells compared to the M2 macrophage prior to polarization.

In certain aspects, described herein is a method of treating pancreatic cancer in a subject comprising administering to the subject an extracellular vesicle comprising an inhibitory RNA targeting human wild-type KRAS; wherein the treatment increases the percentage of polarization of tumor-resident macrophages from the M2 to M1 phenotype to a greater level than that observed in a patient treated with an inhibitory RNA targeting human KRAS$^{G12D}$.

DETAILED DESCRIPTION

Figure 1:
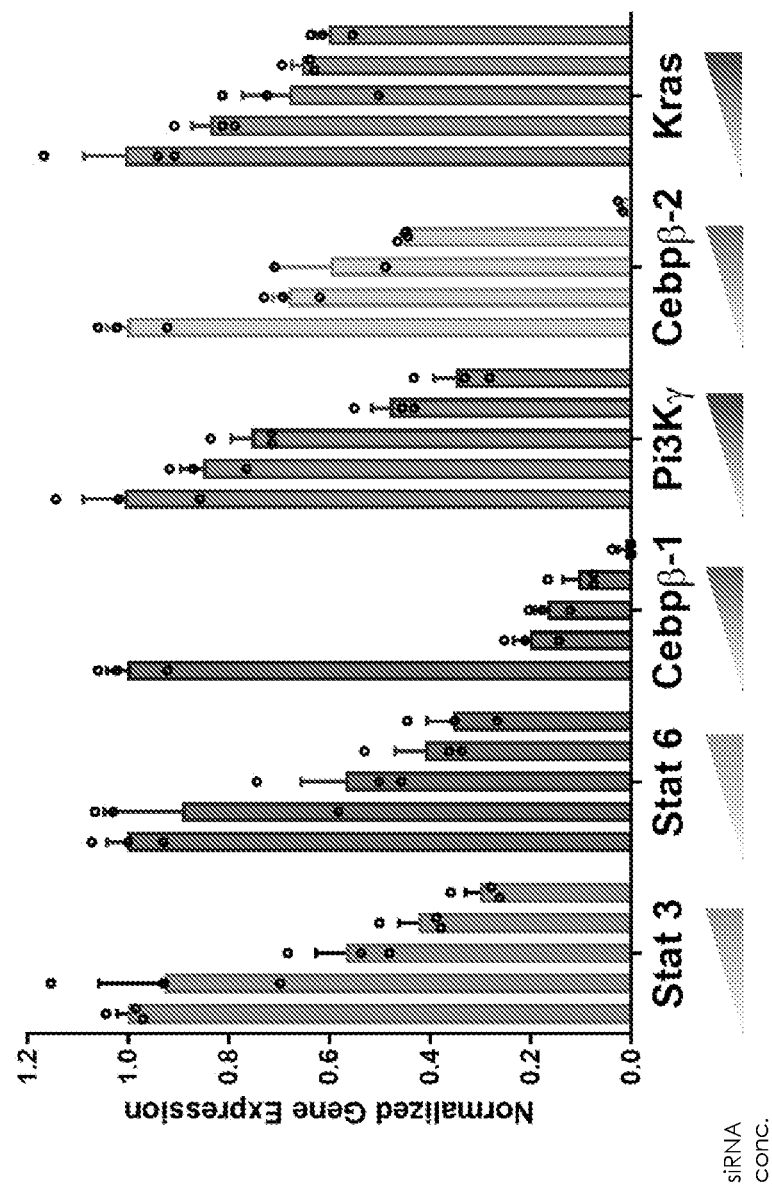
FIG. 1 shows the gene expression levels of Stat 3, Stat 6, Cebpβ-1, Pi3Kγ, CEBPβ-2, and Kras after transfection of increasing amounts of siRNAs targeting each of the gene.

Macrophage polarization is a process by which macrophages adopt different functional programs in response to the signals from their microenvironment. This ability is connected to their multiple roles in the organism: they are powerful effector cells of the innate immune system, but also important in removal of cellular debris, embryonic development and tissue repair.

Macrophage phenotypes are broadly divided into 2 groups: M1 (classically-activated macrophages) and M2 (alternatively-activated macrophages). This broad classification is based on in vitro studies, in which cultured macrophages were treated with molecules that stimulated their phenotype switching to particular state. M1 macrophages are pro-inflammatory, important in direct host-defense against pathogen, such as phagocytosis and secretion of pro-inflammatory cytokines and microbicidal molecules. M2 macrophages have quite the opposite function: regulation of the resolution phase of inflammation and the repair of damaged tissues. See, e.g., Wynn, T. A., Chawla, A., & Pollard, J. W. (2013). Origins and Hallmarks of Macrophages: Development, Homeostasis, and Disease. *Nature,* 496(7446), 445-455; Mills, C. D., Kincaid, K., Alt, J. M., Heilman, M. J., & Hill, A. M. (2000). M-1/M-2 Macrophages and the Th1/Th2 Paradigm. *The Journal of Immunology,* 164(12), 6166-6173. Many solid tumors are characterized by a myeloid-rich cellular infiltrate, often comprising a type of M2 macrophage known as tumor-associated macrophages (TAMs). M2 macrophages (such as TAMs) express high levels of phosphorylated STAT3 and STATE, which promote the expression of the metabolic enzyme Arginase (Arg1). TAMs mediate a number of tumor-promoting activities such as, e.g., promotion of cancer cell motility, metastasis formation and angiogenesis and TAM formation is dependent on microenvironmental factors which are present in developing tumor. TAMs produce immunosuppressive cytokines such as, e.g., IL-10, TGFβ, PGE2 and a very small amount of NO or ROI and low levels of inflammatory cytokines (IL-12, IL-1β, TNFα, IL-6). As compared to "classically-activated" M1 macrophages, presentation of tumor-associated antigens by TAMs is decreased, as is stimulation of the anti-tumor functions of T and NK cells. Unlike M1 macrophages, TAMs are unable to lyse tumor cells. https://en.wikipedia.org/wiki/Macrophage_polarization-cite_note-Sica2008-31 Thus, targeting of TAMs and other M2 macrophages provides a novel therapeutic strategy against cancer, as has been demonstrated through the delivery of agents to either alter the recruitment and distribution of TAMs, deplete existing TAMs, or induce the re-education of TAMs from an M2 to an M1 phenotype.

The exosome therapeutics of the present invention have selective effects on M2 macrophages to promote a tissue-resident microenvironment to treat diseases like cancer and fibrosis by "repolarizing" the aberrant macrophages to an M1 phenotype in the context of these disease. The exosomes described herein are precisely engineered with various biologically active molecules onto the exosome surface or inside the exosome lumen to create candidates that engage pathways that repolarize the M2 macrophages to M1 phenotype to treat human disease.

Tumor associated M2 polarized macrophages, or TAMs, can effectively suppress T cell proliferation and effector function and promote tumor growth. Reversion of TAMs back to an M1 phenotype has also been reported using an antibody which depletes macrophages directed against the CSF-1 receptor. These approaches have shown limited success in clinic trials due to a narrow therapeutic window and lack of specificity due to targeting all macrophages and not just the aberrant M2 macrophages as intended. Such wholesale depletion of macrophages would be expected to result in increased infection risk and other safety concerns. The exosomes of the present invention more selectively target the M2 macrophages due to natural exosome tropism for macrophages and tip the balance of function towards the desired M1 phenotype. These exosomes repolarize macrophages, resulting in the production of the desired spectrum of inflammatory cytokines needed for anti-tumor immune responses. As shown in the examples below, the exosomes have reprogrammed the immunosuppressive M2 macrophages to M1 phenotype in vitro.

In addition to the immune suppression induced in the tumor microenvironment, M2 polarized macrophages secrete large amounts of transforming growth factor beta, or TGFβ, an important cytokine involved in cellular signaling, which induces fibroblast accumulation leading to collagen deposition and tissue remodeling, ultimately resulting in tissue fibrosis. Reprogramming these M2 macrophages to reduce TGFβ production by targeting key signaling molecules, like STAT3, has been shown to have beneficial activity in preclinical models of lung fibrosis. Several small molecule approaches to targeting STAT3 have been employed, but the lack of specificity of inhibition only within the aberrant M2 macrophages has prevented this approach to treatment from being viable. Certain exosomes described here selectively target key pathways in M2 macrophages allowing them to target STAT3 and other cellular pathways in lung and other tissue fibrosis syndromes.

Disclosed herein are extracellular vesicles useful for modulating macrophages of the immune system. These extracellular vesicles comprise one or more immunomodulating component(s) that, upon contact with a macrophage, inhibit at least one macrophage target gene thereby increasing macrophage polarization from an M2 to an M1 phenotype, as compared to equimolar amount(s) of the one or more immunomodulating component(s) alone. Also provided are methods for producing the extracellular vesicles, and methods of using these extracellular vesicles to treat cancer and other immune system related diseases such as, e.g., fibrotic conditions.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It is noted that, as used herein and in the appended claims, the singular forms "a," "an," and "the" include plural referents unless the context clearly dictates otherwise. Similarly, the term "at least one" includes plural referents (i.e., is equivalent to the phrase "one or more," unless the context clearly dictates otherwise). It is further noted that the claims can be drafted to exclude any optional element. As such, this statement is intended to serve as antecedent basis for use of such exclusive terminology as "solely," "only" and the like in connection with the recitation of claim elements, or use of a negative limitation.

The term "about" when used to modify numeric values, is intended to encompass variations in the stated values that are functionally equivalent to the stated values for purposes of practicing the described technology, as can be readily determined by the skilled artisan. In certain embodiments the term "about" includes +/−5%, +/−10%, +/−20%, +/−30%, +/−40% or +/−50% variation from the stated values.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject systems for use in practicing the subject methods will be discussed in greater detail, followed by a review of associated methods.

As used herein, the term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells. Species of extracellular vesicles include exosomes and nanovesicles, as described, e.g., in co-owned U.S. Pat. No. 10,195,290, incorporated herein by reference for all purposes.

As used herein the term "exosome" refers to a cell-derived small (between 20-300 nm in diameter, more preferably 40-200 nm in diameter) vesicle comprising a membrane that encloses an internal space, and which is generated from the cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof.

As used herein, the term "nanovesicle" refers to a cell-derived small (between 20-250 nm in diameter, more preferably 30-150 nm in diameter) vesicle comprising a membrane that encloses an internal space, and which is generated from the cell by direct or indirect manipulation such that the nanovesicle would not be produced by the producer cell without the manipulation. Appropriate manipulations of the producer cell include but are not limited to serial extrusion, treatment with alkaline solutions, sonication, or combinations thereof. The production of nanovesicles can, in some instances, result in the destruction of the producer cell. Preferably, populations of nanovesicles are substantially free of vesicles that are derived from producer cells by way of direct budding from the plasma membrane or fusion of the late endosome with the plasma membrane. The nanovesicle is a species of extracellular vesicle. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to the manipulation, can be isolated from the producer cell based on its size, density, biochemical parameters, or a combination thereof.

The term "M2 phenotype" as used herein, refers to macrophages that exhibit one or more tumor promoting activities or express markers known in the art to be associated with the M2 phenotype such as, but not limited to, reduced or lack of stimulation of $CD8^+$ T-Cells and/or Natural Killer cells; lack of phagocytosis of tumor cells; secretion and/or expression of M2 associated cytokines (e.g., IL-10, TGFβ, PGE2, CCL2, CCL17, CCL18, CCL22 and CCL24); secretion and/or expression of growth factors (e.g., VEGF-A, VEGF-C, EGF, and TGF-β); secretion and/or expression of metastatic enzymes (e.g., matrix metalloproteinases MMP2, MMP9, cysteine cathepsin proteases); secretion/expression of immunosuppressive factors (e.g., Arginase I (ArgI), which withdraws the substrate L-arginine from inducible nitric oxide synthase (iNOS)); expression of cell surface markers YM1, FIZZ1, Dectin-1, MGL, expression of M2 associated miRNAs (e.g., miRNA146a, miRNA let 7b, and miR-223) (see, e.g., Mosser, D. M., & Edwards, J. P. (2008). Exploring the full spectrum of macrophage activation. *Nature Reviews Immunology,* 8(12), 958-96; Murray, P. J., Allen, J. E., Biswas, S. K., Fisher, E. A., Gilroy, D. W., Goerdt, S., Wynn, T. A. (2014). Macrophage activation and polarization: nomenclature and experimental guidelines. *Immunity,* 41(1), 14-20; and Liu, Y. C., Zou, X. B., Chai, Y. F., & Yao, Y. M. (2014). Macrophage polarization in inflammatory diseases. *International Journal of Biological Sciences,* 10(5), 520-5299, and references cited therein, each incorporated by reference for all purposes) and/or reduced expression/secretion of M1 associated factors or reduced M1 associated activities listed below compared to at least one reference sample, wherein the reference sample comprises a population of M1-activated macrophages. M1-activation in vitro is evoked by treatment with TLR ligands such as bacterial lipopolysaccharide (LPS)-typical for Gram-negative bacteria and lipoteichoic acid (LTA)-typical for Gram-positive bacteria, granulocyte-macrophage colony-stimulating factor (GM-CSF) or combination of LPS and interferon-gamma (IFN-γ). See Mills, C. D., Kincaid, K., Alt, J. M., Heilman, M. J., & Hill, A. M. (2000). M-1/M-2 Macrophages and the Th1/Th2 Paradigm. *The Journal of Immunology,* 164(12), 6166-6173; Krausgruber, Thomas, et al. "IRF5 promotes inflammatory macrophage polarization and TH1-TH17 responses." *Nature immunology* 12.3 (2011): 231-238 and Martinez, F. O., & Gordon, S. (2014). The M1 and M2 paradigm of macrophage activation: time for reassessment. F1000Prime Reports, 6 (March), 1-13, and references cited therein, each incorporated herein by reference for all purposes.

The term "M1 phenotype" as used herein, refers to macrophages that exhibit anti-tumor activities or markers known in the art to be associated with the M1 phenotype such as, but not limited to, stimulation of $CD8^+$ T-Cells and/or Natural Killer cells, phagocytosis of tumor cells, secretion and/or expression of M1 associated cytokines (e.g., INFγ, IL-12, IL-23, TNFα, IL-6, IL-1, CCLS, CSCL9, CXCL10 and CXCL11), expression of M1 associated miR-NAs (e.g., miRNA155, miR-33) (see, e.g., Mosser, D. M., & Edwards, J. P. (2008). Exploring the full spectrum of macrophage activation. *Nature Reviews Immunology*, 8(12), 958-96; Murray, P. J., Allen, J. E., Biswas, S. K., Fisher, E. A., Gilroy, D. W., Goerdt, S., Wynn, T. A. (2014). Macrophage activation and polarization: nomenclature and experimental guidelines. *Immunity*, 41(1), 14-20; and Liu, Y. C., Zou, X. B., Chai, Y. F., & Yao, Y. M. (2014). *Macrophage polarization in inflammatory diseases. International Journal of Biological Sciences*, 10(5), 520-5299, and references cited therein, each incorporated by reference for all purposes) and/or reduced expression/secretion of M2 associated factors or reduced M2 associated activities listed above compared to at least one reference sample, wherein the reference sample comprises a population of M2-activated macrophages. M2-activation in vitro is evoked by treatment with IL-4 and IL-13 (see, e.g., Liu, Y. C., Zou, X. B., Chai, Y. F., & Yao, Y. M. (2014). *Macrophage polarization in inflammatory diseases. International Journal of Biological Sciences*, 10(5), 520-529, incorporated by references for all purposes).

The term "macrophage polarization" as used herein, refers to change of a macrophage from an M2 to an M1 phenotype and/or refers to an increase in the percentage of a population of macrophages found in a patient (e.g., macrophages associated with a tumor, or circulating macrophages) of macrophages exhibiting the M1 phenotype as compared to at least one reference sample (e.g., a sample taken from the same patient prior to the test sample or historical data). See, e.g., Mills, C. D., Kincaid, K., Alt, J. M., Heilman, M. J., & Hill, A. M. (2000). M-1/M-2 Macrophages and the Th1/Th2 Paradigm. *The Journal of Immunology*, 164(12), 6166-6173; Mosser, D. M., & Edwards, J. P. (2008). Exploring the full spectrum of macrophage activation. *Nature Reviews Immunology*, 8(12), 958-969; and Xue, J., Schmidt, S. V. and Schultze, J. L. (2014), Transcriptome-Based Network Analysis Reveals a Spectrum Model of Human Macrophage Activation. *Immunity*, 40(2)L 274-288, each incorporated by reference for all purposes.

The term "extracellular vesicle delivery" or "delivery of extracellular vesicles" refers to the administration and localization of extracellular vesicles to target tissues, cells, and/or organs of the subject. In some embodiments, the immunomodulating component can be delivered to the cytoplasm of a target cell. In other embodiments, the immunomodulating component is delivered to the membrane of the target cell. In some embodiments, the membrane of the extracellular vesicle fuses with a membrane of a target cell.

As used herein, the term "producer cell" refers to any cell from which an extracellular vesicle can be isolated. A producer cell is a cell which serves as a source for the extracellular vesicle. A producer cell can share a protein, lipid, sugar, or nucleic acid component with the extracellular vesicle. In some embodiments, the producer cell is a modified or synthetic cell. In some embodiments, the producer cell is a cultured or isolated cell. In certain embodiments, the producer cell is a cell line. In some embodiments, the producer cell line is a human embryonic kidney cell line. In some embodiments, the producer cell line is a HEK293SF cell line. In certain other embodiments, the producer cell is a primary cell. In some particular embodiments, the producer cell is an immune cell, such as, e.g., a B lymphocyte, a T lymphocyte, a dendritic cell, a mast cell, a macrophage, a natural killer cell (NK cell), an antigen presenting cell, a T helper cell, or a regulatory T cell (Treg cell).

"Membrane" as used herein is a boundary layer that separates an interior space from an exterior space comprising one or more biological compounds, typically lipids, and optionally polypeptides and/or carbohydrates. In some embodiments, the membrane comprises lipids and fatty acids. In some embodiments, the membrane comprises phospholipids, glycolipids, fatty acids, sphingolipids, phosphoglycerides, sterols, cholesterols, and phosphatidylserines. In some of these embodiments, the membrane further comprises one or more polypeptide and/or one or more polysaccharide, such as glycan. The extracellular vesicle comprises a membrane as defined herein.

As used herein, the term "immunomodulating component" refers to a therapeutic agent that acts on a target (e.g., a target gene, including by way of example but not limitation KRAS, HRAS, NRAS, HIF1-alpha, HIF1-beta, Sp1, P300, LKB1, AMPK, STAT3, STATE, n-MYC, c-MYC, HCAR1, A2AB, IDO, TDO, Arginase, Glutaminase, CEBP/β, Pi3Kγ, and PKM2) that is contacted with the agent, and modifies an immune cell (e.g., a macrophage or other immune cells). The immunomodulating component that can be introduced into an extracellular vesicle and/or a producer cell include therapeutic agents such as, a polynucleotide, such as an inhibitory nucleic acid (e.g., antisense oligonucleotide (ASO), siRNA, miRNA, antisense RNA, shRNA, lncRNA, pri-miRNA and pre-miRNA), an agonist, an antagonist, an antibody, and/or an antigen-binding fragment, modulators of immune checkpoint inhibitors or ligands of immune checkpoint inhibitors, surface antigens and derivatives thereof, and/or cytokines and derivatives thereof. In certain embodiments the immunomodulating component is an inhibitory nucleic acid (e.g., antisense oligonucleotide (ASO), siRNA, miRNA, antisense RNA, shRNA, lncRNA, pri-miRNA and pre-miRNA). See, e.g., Weiss, B. (ed.): Antisense Oligodeoxynucleotides and Antisense RNA: Novel Pharmacological and Therapeutic Agents, CRC Press, Boca Raton, Fla., 1997; Elbashir S, Harborth J, Lendeckel W, Yalcin A, Weber K, Tuschl T (2001). "Duplexes of 21-nucleotide RNAs mediate RNA interference in cultured mammalian cells". *Nature*. 411 (6836): 494-988; Bartel D P (January 2004). "MicroRNAs: genomics, biogenesis, mechanism, and function". *Cell*. 116 (2): 281-97; Paddison, P J; Caudy, A A; Bernstein, E; Hannon, G J; Conklin, D S (15 Apr. 2002). "Short hairpin RNAs (shRNAs) induce sequence-specific silencing in mammalian cells". *Genes & Development*. 16 (8): 948-58; Ma L, Bajic V B, Zhang Z (June 2013). "On the classification of long non-coding RNAs". *RNA Biology*. 10 (6): 925-33; and Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T (March 2003). "A uniform system for microRNA annotation". *RNA*. 9 (3): 277-9, each of which is incorporated herein for all purposes.

As used herein, the phrase "nucleic acid molecule that inhibits" or "inhibitory nucleic acid" refers to any nucleic acid that, when introduced into a cell so that it interacts with a target gene, results in inhibition of the expression or activity of that target gene. A nucleic acid molecule that inhibits, i.e., an inhibitory nucleic acid may be DNA, or an inhibitory RNA (e.g., siRNA, miRNA, antisense RNA, shRNA, lncRNA, pre-miRNA, or mRNA), wherein said RNA is single stranded, double stranded, or contains both single stranded and double stranded regions. In some embodiments, an inhibitory nucleic acid is an antisense oligonucleotide (ASO). The ASO can be a single-stranded or double-stranded DNA, RNA, or DNA/RNA hybrid. See, e.g., Antisense Oligodeoxynucleotides and Antisense RNA: Novel Pharmacological and Therapeutic Agents, CRC Press, Boca Raton, Fla., 1997, incorporated herein by reference for all purposes. An "EXO ASO" is an ASO that is physically associated with an extracellular vesicle such as, e.g., an exosome, through interactions with the vesicle membrane (e.g., as occurs with cholesterol- or fatty-acyl-derivatized ASOs), or by loading into the vesicle lumen using techniques such as electroporation, or via genetic engineering of a producer cell such as by, e.g., transfection or transduction to introduce into the producer cell a construct that encodes the desired ASO, followed by isolation of extracellular vesicles from the engineered producer cell.

The term "receiver" refers to a molecule that directs the extracellular vesicle to a target and/or promotes the interaction of the extracellular vesicle with the target in the subject. In some embodiments, the receiver is a polypeptide, also sometimes referred to herein as a "receiver polypeptide." In some embodiments, the receiver is capable of increasing the concentration of the immunomodulating component in the tissue of the subject, such as by directed trafficking to the target tissue of the subject. Examples of receivers include, but are not limited to, examples listed in Table 3.

The term "target" can refer to a gene, the activity of which is to be modulated by an immunomodulatory component of the present disclosure (i.e., a target gene). In certain embodiments, the target gene is inhibited by a nucleic acid molecule associated with (i.e., bound to the membrane surface, intercalated within the lipid bilayer, or encapsulated within the vesicle's enclosed volume) extracellular vesicles, such as, e.g., an inhibitory ASO. Examples of target genes include, but are not limited to, KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, Glutaminase, CEBP/β, Pi3Kγ, and PKM2. "Target" can also refer to a cell to which the extracellular vesicles of the present disclosure are directed (i.e., a target cell). In certain embodiments, the target cell is an immune cell (e.g., a macrophage). In certain embodiments, the target cell is a hematopoietic stem cell or pluripotent stem cell. In certain embodiments, the target cell is a circulating macrophage. In certain embodiments, the target cell is a tumor resident macrophage (i.e., a macrophage located in the tumor microenvironment, in the tumor tissue or near the tumor surface). Additionally, "target" can also refer to a protein on a target cell, whose activity is modulated by contact with an immunomodulatory component of the present disclosure, or a protein that acts as a ligand for binding the extracellular vesicles of the present disclosure (i.e., a target protein), Thus, in certain embodiments, the target protein is on the target cell and interacts with the extracellular vesicle.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

The term "immune checkpoint inhibitor" or "checkpoint inhibitor" as used herein, refers to a therapeutic agent that stimulates immune cell activity by reducing immunosuppressive checkpoint pathways that suppress immune cells (e.g., agents that inhibit PD-1/PD-L1 (such as Nivolumab Cemiplimab and Pembrolizumab targeting PD-1, and Atezolizumab, Avelumab, Durvalumab, each targeting PD-L1) and CTLA-4/B7-1/B7-2, such as Ipilimumab). See, e.g., Pardoll D M (March 2012). "The blockade of immune checkpoints in cancer immunotherapy". *Nature Reviews. Cancer.* 12 (4): 252-64.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibody includes bispecific antibodies and multispecific antibodies so long as they exhibit the desired biological activity or function. Exemplary antibody compositions include antibodies that inhibit CTLA-4, such as, e.g., Ipilimumab, those that inhibit PD-1, such as, e.g., Nivolumab Cemiplimab and Pembrolizumab, those that inhibit PD-L1, such as, e.g., Atezolizumab, Avelumab, Durvalumab, and those that inhibit CSFR1, such as, e.g., Pexidartinib, PLX7486, ARRY-382, JNJ-40346527, BLZ945, Emactuzumab, AMG820, IMC-CS4 and Cabiralizumab.

The term "antigen-binding fragment" used herein refers to fragments of an intact immunoglobulin, and any part of a polypeptide including antigen binding regions having the ability to specifically bind to the antigen. For example, the antigen-binding fragment can be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CHI of the heavy chain. A Fab' fragment differs from a Fab fragment in that the Fab' fragment additionally includes the hinge region of the heavy chain, including at least one cysteine residue at the C-terminal of the heavy chain CHI region. The F(ab')$_2$ fragment is produced whereby cysteine residues of the Fab' fragment are joined by a disulfide bond at the hinge region. An Fv fragment is the minimal antibody fragment having only heavy chain variable regions and light chain variable regions, and a recombinant technique for producing the Fv fragment is well-known in the art. Two-chain Fv fragments can have a structure in which heavy chain variable regions are linked to light chain variable regions by a non-covalent bond. Single-chain Fv (scFv) fragments generally can have a dimer structure as in the two-chain Fv fragments in which heavy chain variable regions are covalently bound to light chain variable regions via a peptide linker or heavy and light chain variable regions are directly linked to each other at the C-terminal thereof. The antigen-binding fragment can be obtained using a protease (for example, a whole antibody is digested with papain to obtain Fab fragments, and is digested with pepsin to obtain F(ab')$_2$ fragments), and can be prepared by a genetic recombinant technique. A dAb fragment consists of a VH domain. Single-chain antibody molecules can comprise a polymer with a number of individual molecules, for example, dimer, trimer or other polymers.

The phrase "nucleic acid molecule" refers to a single or double-stranded polymer of deoxyribonucleotide or ribonucleotide bases. It includes chromosomal DNA and self-replicating plasmids, vectors, mRNA, tRNA, siRNA, miRNA, etc. The nucleic acid molecule can be recombinant and exogenous polypeptides can be expressed when the nucleic acid is introduced into a cell. The term encompasses chemically modified nucleic acids, such as those described in, e.g., Selvam C, Mutisya D, Prakash S, Ranganna K, Thilagavathi R. "Therapeutic potential of chemically modified siRNA: Recent trends," *Chem Biol Drug Des.* 2017 November; 90(5):665-678, Locked Nucleic Acids (LNAs) as described in, e.g., Petersen M, Wengel J (February 2003). "LNA: a versatile tool for therapeutics and genomics". *Trends Biotechnol.* 21 (2): 74-81; and other types of clinically-relevant, chemically modified nucleic acids such as those described in, e.g., Summerton, J; Weller, D (1997). "Morpholino Antisense Oligomers: Design, Preparation and Properties". *Antisense & Nucleic Acid Drug Development.* 7 (3): 187-195; Goodchild, J (2011). Therapeutic oligonucleotides. *Methods in Molecular Biology.* 764. pp. 1-15, each incorporated herein by reference for all purposes.

The term "agonist" refers to a molecule that binds to a receptor and activates the receptor to produce a biological response. Receptors can be activated by either an endogenous or an exogenous agonist. Non-limiting examples of endogenous agonist include hormones and neurotransmitters. Non-limiting examples of exogenous agonists include various classes of compounds including small molecules, antibodies, synthetic peptides, etc. The agonist can be a full, partial, or inverse agonist.

The term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

As used herein, the term "pharmaceutical composition" refers to one or more of the compounds described herein, such as, e.g., an extracellular vesicle mixed or intermingled with, or suspended in one or more other chemical components, such as pharmaceutically-acceptable carriers and excipients. One purpose of a pharmaceutical composition is to facilitate administration of preparations of extracellular vesicles to a subject. The term "pharmaceutically-acceptable" and grammatical variations thereof, refers to compositions, carriers, diluents and reagents capable of administration to or upon a subject without the production of undesirable physiological effects to a degree that prohibits administration of the composition. The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired extracellular vesicles, that have undergone one or more processes of purification, e.g., a selection or an enrichment of the desired extracellular vesicle preparation. In some embodiments, isolating or purifying as used herein is the process of removing, partially removing (e.g. a fraction) of the extracellular vesicles from a sample containing producer cells. In some embodiments, an isolated extracellular vesicle composition has no detectable undesired activity or, alternatively, the level or amount of the undesired activity is at or below an acceptable level or amount. In other embodiments, an isolated extracellular vesicle composition has an amount and/or concentration of desired extracellular vesicles at or above an acceptable amount and/or concentration. In other embodiments, the isolated extracellular vesicle composition is enriched as compared to the starting material (e.g. producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated extracellular vesicle preparations are substantially free of residual biological products. In some embodiments, the isolated extracellular vesicle preparations are 100% free, 99% free, 98% free, 97% free, 96% free, or 95% free of any contaminating biological matter. Residual biological products can include abiotic materials (including chemicals) or unwanted nucleic acids, proteins, lipids, or metabolites. Substantially free of residual biological products can also mean that the extracellular vesicle composition contains no detectable producer cells and that only extracellular vesicles are detectable.

The terms "administration," "administering" and variants thereof refer to introducing a composition, such as an extracellular vesicle, or agent into a subject and includes concurrent and sequential introduction of one or more additional compositions or agents on any schedule consistent with producing a therapeutic effect. Timing of dose administration can be selected to achieve constant levels within a subject (e.g., plasma levels) of the administered agent, or to episodic exposure, e.g., to reduce toxicity or prevent desensitization. Methods of achieving these results are well known to the ordinarily-skilled practitioner, based on known pharmacokinetic principles as set out in, e.g., Goodman & Gilman's The Pharmacological Basis of Therapeutics (Macmillan Publishing Co. 13$^{th}$ Ed.) The introduction of a composition or agent into a subject is by any suitable route, including orally, pulmonarily, intranasally, parenterally (intravenously, intra-arterially, intramuscularly, intraperitoneally, or subcutaneously), rectally, intralymphatically, intrathecally, periocularly, intra-tumorally or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "modulate," "modulating," "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity. The terms "inhibition," "repression," "modulation," are used herein to describe the changes in the expression or activity of the target gene as compared to the conditions without the immunomodulating component(s). Inhibition refers to elimination or substantial elimination of the gene expression or activity. Repression means a reduction, but not complete elimination or substantial elimination, of the gene expression or activity. Modulation means any alteration, up or down, of the gene expression or activity.

The term "sufficient amount" means an amount sufficient to produce a desired effect, e.g., an amount sufficient to modulate a condition in the subject.

The term "therapeutically effective amount" is an amount that is effective to ameliorate a symptom of a disease. A therapeutically effective amount can be a "prophylactically effective amount" as prophylaxis can be considered therapy.

Percent "identity" between a nucleotide sequence and a reference sequence, is defined as the percentage of single nucleotides in the nucleotide sequence that are identical to the single nucleotides in the reference sequence, after aligning the sequences and introducing gaps, if necessary, to achieve the maximum percent sequence identity. Alignment for purposes of determining percent nucleotide sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared. For further details about the BLAST algorithm, see Mount, D. W. (2004). Bioinformatics: Sequence and Genome Analysis (2nd ed.). Cold Spring Harbor Press. ISBN 978-0-87969-712-9.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared. For further details about the BLAST algorithm, see Mount, D. W. (2004). Bioinformatics: Sequence and Genome Analysis (2nd ed.). Cold Spring Harbor Press. ISBN 978-0-87969-712-9.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline.

The term "in vivo" refers to processes that occur in a living organism.

The term "mammal" as used herein includes both humans and non-human mammals.

Abbreviations used in this application include the following: "mRNA" refers to messenger RNA; "miRNA" refers to microRNA; "siRNA" refers to small interfering RNA; "antisense RNA" refers to single stranded RNA that is complementary to an mRNA, which may additionally comprise DNA nucleotides, and is often referred to as an antisense oligonucleotide or "ASO"; "shRNA" refers to small or short hairpin RNA; "lncRNA" refers to long non-coding RNA; and "dsDNA" refers to double stranded DNA.

Compositions

Aspects of the subject disclosure include compositions capable of regulating the immune system. The composition comprises an extracellular vesicle comprising a cell membrane, and at least one immunomodulating component associated with the cell membrane or enclosed within the membrane-bound enclosed volume. Enclosure within the membrane-bound volume can be accomplished using techniques including electroporation, lyophilization, or through engineering of producer cells (such as, e.g., HEK293 cells, Chinese hamster ovary (CHO) cells, and mesenchymal stem cells (MSCs)) to introduce constructs that encode the immunomodulatory component such as a nucleic acid (encoding an ASO) or a protein. Association with cell membrane encompasses binding to the inner or outer lipid leaflet of the membrane and transmembrane insertion into the lipid bilayer. In some instances membrane association is achieved using a protein (e.g., a scaffold protein or fragment thereof) such as, e.g., prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4 that have been identified to be highly enriched on the surface of exosomes (as described in co-owned U.S. Pat. No. 10,195,290) which can provide an element of a fusion protein comprising the scaffold and the immunomodulatory component. Such extracellular vesicles and exemplary techniques are described in detail in co-owned U.S. Pat. No. 10,195,290, incorporated herein by reference for all purposes. As described in co-owned U.S. Pat. No. 10,195,290, surface-engineered exosomes can be generated by chemical and/or physical methods, such as PEG-induced fusion and/or ultrasonic fusion to introduce these scaffold proteins (and fragments thereof) into the exosomes or producer cells. A complex can be generated between an exogenous therapeutic protein and the scaffold protein. Alternatively, a fusion protein can be produced by conjugating a scaffold protein and an exogenous therapeutic protein, such as, e.g., an immunomodulating protein, and producing an engineered exosome containing the complex or fusion protein on the surface, using the aforementioned chemical and/or physical methods. A native full-length or a biologically active fragment of the therapeutic protein can be transported to the surface of exosomes by being conjugated to the scaffold protein. Such exosomes can also be obtained from a producer cell that comprises the exogenous sequence inserted into a genome of the cell. For example, the exogenous sequence can be inserted into a genomic site located 3' or 5' end of a genomic sequence encoding PTGFRN, BSG, IGSF2, IGSF3, IGSF8, ITGB1, ITGA4, SLC3A2 or ATP transporter. For example, the exogenous sequence can be inserted into a genomic sequence encoding PTGFRN, BSG, IGSF2, IGSF3, IGSF8, ITGB1, ITGA4, SLC3A2 or ATP transporter. Association with the cell membrane encompasses binding of the immunomodulating component to the internal or external membrane surface, anchoring of the immunomodulating component within the lipid bilayer, or extension of the immunomodulating component through the lipid bilayer. The immunomodulating component can be tethered to a scaffold protein, or expressed as a fusion protein with a scaffold protein as described in co-owned U.S. Pat. No. 10,195,290.

The Extracellular Vesicle

In various embodiments, the composition comprises an extracellular vesicle. In certain embodiments, the extracellular vesicle is a cell-derived vesicle comprising a membrane that encloses an internal space, as described in co-owned U.S. Pat. No. 10,195,290.

In various embodiments, the extracellular vesicle can be a membrane-bound vesicle that has a smaller diameter than the cell from which it is derived. In some embodiments, the extracellular vesicle has a longest dimension between about 20-1000 nm, such as between about 20-100 nm, 20-200 nm, 20-300 nm, 20-400 nm, 20-500 nm, 20-600 nm, 20-700 nm, 20-800 nm, 20-900 nm, 30-100 nm, 30-200 nm, 30-300 nm, 30-400 nm, 30-500 nm, 30-600 nm, 30-700 nm, 30-800 nm, 30-900 nm, 40-100 nm, 40-200 nm, 40-300 nm, 40-400 nm, 40-500 nm, 40-600 nm, 40-700 nm, 40-800 nm, 40-900 nm, 50-150 nm, 50-500 nm, 50-750 nm, 100-200 nm, 100-500 nm, or 500-1000 nm.

In certain embodiments, the extracellular vesicle is an exosome. In certain embodiments, the extracellular vesicle is a nanovesicle. In certain embodiments, the extracellular vesicle is an apoptotic body. In certain embodiments, the extracellular vesicle is a fragment of cell. In certain embodiments, the extracellular vesicle is a vesicle derived from cell by direct or indirect manipulation. In certain embodiments, the extracellular vesicle is a vesiculated organelle. In various embodiments, the extracellular vesicle is a vesicle produced by living cells.

In some embodiments, the extracellular vesicle is derived from a living organism. In some embodiments, the extracellular vesicle is derived from a dead organism. In some embodiments, the extracellular vesicle is derived from an explanted tissue. In some embodiments, the extracellular vesicle is derived from an explanted organ. In some embodiments, the extracellular vesicle is derived from cultured cells. In some of these embodiments, when the extracellular vesicle is generated in a cell culture system, the extracellular vesicle is further isolated (e.g., by separating the extracellular vesicle from the cultured cells). Separation can be achieved by sedimentation. For example, the extracellular vesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more proteins on the surface of the extracellular vesicle. The proteins may be a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc.

In various embodiments, the extracellular vesicle comprises lipids or fatty acids and polypeptides. In certain embodiments, the extracellular vesicle further comprises a sugar. In certain embodiments, the extracellular vesicle further comprises a polynucleotide.

In various embodiments, the extracellular vesicle membrane comprises an interior surface and an exterior surface and encloses an internal space. In some embodiments, the extracellular vesicle further comprises a payload, such as an immunomodulatory component as described herein. In certain embodiments, the payload is enclosed within the internal space. In certain embodiments, the payload is displayed on the external surface of the extracellular vesicle. In certain embodiments, the payload is spanning the membrane of the extracellular vesicle. In various embodiments, the payload comprises nucleic acids, proteins, carbohydrates, lipids, small molecules, and/or combinations thereof. Methods for producing extracellular vesicles with payloads include electroporation, lyophilization, and genetic engineering of producer cells from which extracellular vesicles can be isolated. See, e.g., co-owned U.S. Pat. No. 10,195,290 and supra. In some embodiments, the extracellular vesicle further comprises a receiver, i.e., a targeting moiety that can be specific to an organ, a tissue, or a cell as described in co-owned U.S. Pat. No. 10,195,290. Fusion proteins having a targeting moiety are used. For example, fusion proteins can comprise PTGFRN, BSG, IGSF2, IGSF3, IGSF8, ITGB1, ITGA4, SLC3A2, ATP transporter, or a fragment or a variant thereof, and a targeting moiety. The targeting moiety can be used for targeting the exosome to a specific organ, tissue, or cell for a treatment using the exosome. In some embodiments, the targeting moiety is an antibody or antigen-binding fragment thereof. Antibodies and antigen-binding fragments thereof include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)2, Fab, Fab', and F(ab') 2, F(ab1)2, Fv, dAb, and Fd fragments, diabodies, and antibody-related polypeptides. Antibodies and antigen-binding fragments thereof also includes bispecific antibodies and multispecific antibodies so long as they exhibit the desired biological activity or function.

The Exosome

In various embodiments, the extracellular vesicle is an exosome. In certain embodiments, the exosome is a small membrane-bound vesicle secreted by producer cells.

In some embodiments, the exosome from the producer cell has a longest dimension between about 20-300 nm, such as between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm.

In particularly preferred embodiments, the exosome from the producer cell described herein has a longest dimension between about 30-100 nm. In another preferred embodiment, the exosome from the producer cell has a longest dimension between about 20-300 nm. In another preferred embodiment, the exosome from the producer cell has a longest dimension between about 40-200 nm. In another embodiment, a population of the exosomes described herein comprise a population wherein 90% of the exosomes have a longest dimension 20-300 nm. In another embodiment, a population of the exosomes described herein comprise a population wherein 95% of the exosomes have a longest dimension 20-300 nm. In another embodiment, a population of the exosomes described herein comprise a population wherein 99% of the exosomes have a longest dimension 20-300 nm. In another embodiment, a population of the exosomes described herein comprise a population wherein 90% of the exosomes have a longest dimension 40-200 nm. In another embodiment, a population of the exosomes described herein comprise a population wherein 95% of the exosomes have a longest dimension 40-200 nm. In another embodiment, a population of the exosomes described herein comprise a population wherein 99% of the exosomes have a longest dimension 40-200 nm. In other preferred embodiments, the size of the exosome or population of exosomes described herein is measured according to methods described, infra.

In some embodiments, the exosome is generated by a producer cell. In some embodiments, the membrane of the exosome comprises one or more molecules derived from the producer cell. In some embodiments, the exosome is generated in a cell culture system and isolated (e.g., by separating the exosome from the producer cell). Separation can be achieved by sedimentation. For example, the exosome can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more proteins on the surface of the extracellular vesicle. The one or more proteins on the surface of the extracellular vesicle may be a tetraspanin (e.g., CD63, CD81 and/or CD9), an EWI protein/immunoglobulin superfamily member (e.g., PTGFRN, IGSF8 and/or IGSF3), an integrin (e.g., ITGB1 and/or ITGA4), an ATP transporter protein (e.g., ATP1A1, ATP1A2, ATP1A3, ATP1A4, ATP1B3, ATP2B1, ATP2B2, ATP2B3 and/or ATP2B4), SLC3A2, BSG, or CD98hc. The protein may additionally have activity as an immunomodulating component displayed on the surface of the exosomes, optionally via fusion to a polypeptide moiety that has a desired pharmacologic activity, such as, e.g., an antibody, antibody fragment, scFv, etc. with checkpoint inhibition activity. Such antibodies are known in the art, e.g., Ipilimumab, targeting CTLA-4, Nivolumab Cemiplimab and Pembrolizumab targeting PD-1, and Atezolizumab, Avelumab, Durvalumab, each targeting PD-L1 (see, e.g., Pardoll D M (March 2012). "The blockade of immune checkpoints in cancer immunotherapy". *Nature Reviews. Cancer.* 12 (4): 252-64, incorporated herein by reference.

In some embodiments, the exosome membrane comprises an interior surface and an exterior surface. In certain embodiments, the interior surface faces the inner core of the exosome. In certain embodiments, the exterior surface can be in contact with the endosome, the multivesicular bodies, or the membrane/cytoplasm of a producer cell or a target cell.

In some embodiments, the exosome membrane comprises lipids and fatty acids. In some embodiments, the exosome membrane comprises phospholipids, glycolipids, fatty acids, sphingolipids, phosphoglycerides, sterols, cholesterols, and phosphatidylserines. In some embodiments, the lipid and fatty acid can be one or more of those listed in Table 1.

In certain embodiments, the exosome comprises a lipid bilayer composed of an inner leaflet and an outer leaflet. The composition of the inner and outer leaflet can be determined by transbilayer distribution assays known in the art, see e.g., Kuypers et al. Biohim Biophys Acta 1985 819:170. In some embodiments, the composition of the outer leaflet is between approximately 70-90% choline phospholipids, between approximately 0-15% acidic phospholipids, and between approximately 5-30% phosphatidylethanolamine. In some embodiments, the composition of the inner leaflet is between approximately 15-40% choline phospholipids, between approximately 10-50% acidic phospholipids, and between approximately 30-60% phosphatidylethanolamine.

In some embodiments, the exosome membrane further comprises one or more polypeptides. In certain embodiments, the exosome comprises one or more polypeptide selected from the following list, including but not limited to, spectrin, myosin-like polypeptide, band 3, SLC4A1, actin, actin-like polypeptide, glyceraldehyde 3-P dehydrogenase (G3PD), tetraspanins (e.g., CD63, CD81 and/or CD9), Alix and TSG101, integrins (e.g., ITGB1 and/or ITGA4), selectins, CR1, TNFRI, proteolytic enzymes, glycosylphosphatidylinositol (GPI)-linked proteins or histones, EWI protein/immunoglobulin superfamily members (e.g., PTGFRN, IGSF8 and/or IGSF3), ATP transporter proteins (e.g., ATP1A1, ATP1A2, ATP1A3, ATP1A4, ATP1B3, ATP2B1, ATP2B2, ATP2B3 and/or ATP2B4), SLC3A2, BSG, or CD98hc.) In some embodiments, the exosome comprises at least one polypeptide selected from Table 2.

In some embodiments, the exosome comprises polypeptides on its surface. In some embodiments, the exosome is modified to contain the one or more polypeptides. In some embodiments, the producer cell is modified to contain the one or more polypeptides. In some embodiments, the producer cell naturally contains the one or more polypeptides and exosomes derived therefrom also contain the polypeptides. The levels of any desired surface marker can be modified directly on the exosome (e.g., by contacting the complex with recombinantly produced polypeptides to bring about insertion in or conjugation to the membrane of the complex). Alternatively or in addition, the levels of any desired surface marker can be modified directly on the producer cell (e.g., by contacting the complex with recombinantly produced polypeptides to bring about insertion in or conjugation to the membrane of the cell). Alternatively, the producer cell can be modified by transducing an exogenous nucleic acid into the producer cell to express a desired surface marker. The surface marker can already be naturally present on the producer cell, in which case the exogenous construct can lead to overexpression of the marker and increased concentration of the marker in or on the producer cell. Alternatively, a naturally expressed surface marker can be removed from the producer cell (e.g., by inducing gene silencing in the producer cell). The polypeptides can confer different functionalities to the exosome (e.g., specific targeting capabilities, delivery functions (e.g., fusion molecules), enzymatic functions, increased or decreased half-life in vivo, etc.). In some embodiments, the polypeptides include, but are not limited to CD47, CD55, CD49, CD40, CD133, CD59, glypican-1, CD9, CD63, CD81, integrins, selectins, lectins, and cadherins.

In specific embodiments, the exosomes comprise one or more polypeptides on their surface, wherein said polypeptides are selected from a group of proteins that was recently identified to be enriched on the surface of exosomes (described in detail in co-owned U.S. Patent Application 62/550,543, and PCT/US2018/048026, which is incorporated herein by reference in their entireties). This group of polypeptides includes prostaglandin F2 receptor negative regulator (PTGFRN); basigin (BSG); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4)).

In various embodiments, the one or more polypeptides on the exosome surface comprises an antibody or an antigen-binding fragment. The antibody or antigen-binding fragment can be derived from natural sources, or partly or wholly synthetically produced. In some embodiments, the antibody is a monoclonal antibody. In some of these embodiments, the monoclonal antibody is an IgG antibody. In certain embodiments, the monoclonal antibody is an IgG1, IgG2, IgG3, or IgG4. In some other embodiments, the antibody is a polyclonal antibody. In certain embodiments, the antigen-binding fragment is selected from Fab, Fab', and F(ab')$_2$, F(ab1)$_2$, Fv, dAb, and Fd fragments. In certain embodiments, the antigen-binding fragment is an scFv or (scFv)$_2$ fragment. In certain other embodiments, the antibody or antigen-binding fragment is a Nanobody® (single-domain antibody). In some embodiments, the antibody or antigen-binding fragment is a bispecific or multispecific antibody. In various embodiments, the antibody or antigen-binding fragment thereof binds to mesothelin.

In some embodiments, the exosomes comprise on their surface a fusion protein comprising (1) PTGFRN or a fragment thereof and (2) an antibody or antigen-binding fragment thereof, wherein the antibody or antigen binding fragment thereof binds to PD-1, PD-1L, CSF1-R, or other immunomodulatory component.

In some embodiments, the exosome membrane further comprises one or more polysaccharide, such as glycan.

In some embodiments, the exosome delivers the payload (therapeutic agent) to a target. The payload is a therapeutic agent that acts on a target (e.g., a target cell) that is contacted with the exosome. In certain embodiments, the payload is an immunomodulating component, e.g., an inhibitory RNA. Contacting can occur in vitro or in a subject. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), amino acids (e.g., amino acids comprising a detectable moiety or a toxin that disrupt translation), polypeptides (e.g., enzymes), lipids, carbohydrates, small molecules (e.g., small molecule drugs and toxins), and combinations thereof. In certain embodiments, the exosome delivers more than one therapeutic agent. In certain embodiments, the therapeutic agents are one or more nucleic acids that inhibits one or more target genes. In certain embodiments, the therapeutic agents comprise an antibody and a nucleic acid. In certain embodiments, the therapeutic agents comprise a nucleic acid and a small molecule. In certain embodiments, the therapeutic agent comprises a CSF1R inhibitor, such as clinical candidates Pexidartinib, PLX7486, ARRY-382, JNJ-40346527, BLZ945, Emactuzumab, AMG820, and IMC-CS4 and others described in e.g., Cannarile M A, Weisser M, Jacob W, Jegg A M, Ries C H, RUttinger D (2017). "Colony-stimulating factor 1 receptor (CSF1R) inhibitors in cancer therapy". *Journal for Immunotherapy of Cancer.* 5 (1): 53; see also, e.g., Patel S, Player M R (2009). "Colony-stimulating factor-1 receptor inhibitors for the treatment of cancer and inflammatory disease". Curr Top Med Chem. 9: 599-610, Cabiralizumab (cabira; FPA-008) which is a monoclonal antibody and is in early clinical trials for metastatic pancreatic cancer (see A phase I/II dose escalation and expansion study of cabiralizumab (cabira; FPA-008), an anti-CSF1R antibody, in tenosynovial giant cell tumor (TGCT, diffuse pigmented villonodular synovitis D-PVNS; A Study of Cabiralzumab Given by Itself or With Nivolumab in Advanced Cancer or Cancer That Has Spread; and Novel Combination Shows Promising Responses in Pancreatic Cancer November 2017) In certain embodiments, the therapeutic agent comprises an immune checkpoint inhibitor. In certain embodiments, the immune checkpoint inhibitor in an antibody such as, e.g., Ipilimumab, targeting CTLA-4, Nivolumab Cemiplimab and Pembrolizumab targeting PD-1, and Atezolizumab, Avelumab, Durvalumab, each targeting PD-L1

The exosome can interact with the target cell via membrane fusion and deliver payloads (e.g., therapeutic agents) in an exosome composition to the surface or cytoplasm of a target cell. In some embodiments, membrane fusion occurs between the exosome and the plasma membrane of a target cell. In other embodiments, membrane fusion occurs between the exosome and an endosomal membrane of a target cell.

In some embodiments, the exosome comprises a receiver polypeptide. The receiver polypeptide can be synthetic. In some embodiments, the receiver polypeptide is introduced into the producer cell (e.g., an exogenous nucleic acid that encodes the receiver polypeptide is introduced into the producer cell) or a recombinant receiver polypeptide that is made outside the producer cell (e.g., synthesized by a protein expression system). In some embodiments, the receiver polypeptide (e.g., a recombinantly produced polypeptide) is introduced into the exosome directly (e.g., after the exosome is isolated from the producer cell). In some embodiments, the receiver polypeptide can be on the surface of the exosomes. In some embodiments, the receiver polypeptide is capable of targeting the exosome to a specific target (e.g., a target such as a pathogen, a metabolite, a protein, a polypeptide complex or a cell such as non-functional cell or cancer cell) that circulates in the circulatory system of the subject, such as the blood, or a target that resides in a tissue (such as a diseased tissue).

In some embodiments, the exosome is synthetic. That is to say that modifications are made to the exosomes after their recovery from the producer cell to add additional components. For example, the exosome can comprise a payload, such as, e.g., a therapeutic polypeptide, nucleic acid (such as DNA or RNA) or other polynucleotide, polysaccharide or glycan, lipid or fatty acid, large biologic, small molecule or toxin not found in exosomes upon recovery from the producer cell. In some embodiments, the exosome is modified (e.g., by introducing a payload or otherwise modifying the content of the complex, such as by changing the protein, lipid or glycan content of the membrane). For example, exosomes are first isolated from a producer cell and then modified as desired, thereby generating synthetic exosomes. In some embodiments, the producer cell is modified. For example, an exogenous nucleic acid, an exogenous polypeptide or small molecule or toxin can be introduced into the producer cell. Alternatively or in addition, the producer cell can otherwise be modified (e.g., by modifying the cellular or membrane content, such as by changing the lipid or glycan content of the cell membrane). Exosomes generated from the modified producer cells comprise one or more of the modifications of the producer cell. The process produces synthetic exosomes. In some embodiments, both the producer cell and the exosome isolated from the producer cell are modified as described herein.

Nanovesicle

In various embodiments, the extracellular vesicle is a nanovesicle. In certain embodiments, the nanovesicle is a cell-derived small vesicle comprising a membrane that encloses an internal space, and which is generated from the cell by direct or indirect manipulation such that the nanovesicle would not be produced by the cell without the manipulation. Appropriate manipulations of the cell include but are not limited to serial extrusion, treatment with alkaline solutions, sonication, or combinations thereof and can, in some instances, result in the destruction of the producer cell.

In various embodiments, the nanovesicle has a longest dimension between about 20-250 nm, such as between about 20-100 nm, 20-150 nm, 20-200 nm, 30-100 nm, 30-150 nm, 30-200 nm, 30-250 nm, 40-100 nm, 40-150 nm, 40-200 nm, 40-250 nm, 50-100 nm, 50-150 nm, 50-200 nm, 50-250 nm, 100-200 nm, or 150-250 nm.

In various embodiments, the nanovesicle is derived from a producer cell. In certain embodiments, the nanovesicle is generated from a producer cell by direct or indirect manipulation. Appropriate manipulations include but are not limited to serial extrusion, treatment with alkaline solutions, sonication, or combinations thereof. In some of these embodiments, the manipulation can result in the destruction of the producer cell. In some preferred embodiments, the population of the nanovesicle is substantially free of vesicles that are derived from producer cells by way of direct budding from the plasma membrane or fusion of the late endosome with the plasma membrane.

In some embodiments, the nanovesicle is isolated from the producer cell based on its size, density, biochemical parameters, or a combination thereof. In certain embodiments, the isolation can be achieved by sedimentation. For example, the nanovesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$.

In various embodiments, the nanovesicle comprises lipids or fatty acids and polypeptides. In certain embodiments, the nanovesicle further comprises a sugar. In certain embodiments, the nanovesicle further comprises a polynucleotide. In some embodiments, the nanovesicle further comprises a receiver. In some embodiments, the nanovesicle further comprises a payload. In some of these embodiments, the payload comprises nucleic acids, proteins, carbohydrates, lipids, small molecules, and/or combinations thereof.

The Immunomodulating Component

In an aspect, the extracellular vesicle, e.g., an exosome, comprises at least one immunomodulating component that increases macrophage polarization from an M2 to an M1 phenotype. In an aspect the increase from an M2 to an M1 phenotype is assessed with respect to a reference sample comprising a population of M2 macrophages. In an aspect the increase achieved by the extracellular vesicles of the present disclosure is greater than or equal to that achieved by an equimolar amount of the immunomodulating component alone. In certain embodiments, the immunomodulating component is a polynucleotide that increases macrophage polarization. In certain embodiments, the polynucleotide is a nucleic acid that inhibits at least one gene, such as, e.g., protooncogenes and other type of genes, the inhibition of which promote increased polarization from an M2 to an M1 phenotype, including by way of example, but not limitation, the following genes: KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, Glutaminase, CEBP/β, Pi3Kγ, and PKM2. In certain embodiments, combinations of polynucleotide and proteinaceous immunomodulating components are contemplated, including proteinaceous immunomodulating components such as, e.g., antibodies or antibody fragments that target PD-1, PD-L1, CTLA-4 (such as, e.g., Ipilimumab, targeting CTLA-4, Nivolumab Cemiplimab and Pembrolizumab targeting PD-1, and Atezolizumab, Avelumab, Durvalumab, each targeting PD-L1), CSF1R inhibitors (such as, e.g., such as clinical candidates Pexidartinib, PLX7486, ARRY-382, JNJ-40346527, BLZ945, Emactuzumab, AMG820, and IMC-CS4 and others described in e.g., Cannarile M A, Weisser M, Jacob W, Jegg A M, Ries C H, Rüttinger D (2017). "Colony-stimulating factor 1 receptor (CSF1R) inhibitors in cancer therapy". *Journal for Immunotherapy of Cancer.* 5 (1): 53; see also, e.g., Patel S, Player M R (2009). "Colony-stimulating factor-1 receptor inhibitors for the treatment of cancer and inflammatory disease". Curr Top Med Chem. 9: 599-610, Cabiralizumab (cabira; FPA-008) which is a monoclonal antibody and is in early clinical trials for metastatic pancreatic cancer (see A phase I/II dose escalation and expansion study of cabiralizumab (cabira; FPA-008), an anti-CSF1R antibody, in tenosynovial giant cell tumor (TGCT, diffuse pigmented villonodular synovitis D-PVNS; A Study of Cabiralzumab Given by Itself or With Nivolumab in Advanced Cancer or Cancer That Has Spread; and Novel Combination Shows Promising Responses in Pancreatic Cancer November 2017, and other immunomodulatory components useful in the treatment of cancer and inflammatory conditions.

In some of these embodiments, the nucleic acid includes, but is not limited to, an mRNA, a miRNA, an siRNA, an antisense RNA, an shRNA, a lncRNA, and a dsDNA. In some embodiments, the nucleic acid is an RNA (e.g., an mRNA, a miRNA, an siRNA, an antisense RNA, an shRNA, or an lncRNA). In some of these embodiments, when the polynucleotide is an mRNA, it can be translated into a desired polypeptide. In some embodiments, the polynucleotide is a microRNA (miRNA), pri-miRNA, or pre-miRNA molecule. In some of these embodiments, the miRNA is delivered to the cytoplasm of the target cell, such that the miRNA molecule can silence a native mRNA in the target cell. In some embodiments, the polynucleotide is a small interfering RNA (siRNA) or a short hairpin RNA (shRNA) capable of interfering with the expression of an oncogene or other dysregulating polypeptides. In some of these embodiments, the siRNA is delivered to the cytoplasm of the target cell, such that the siRNA molecule can silence a native mRNA in the target cell. In some embodiments, the polynucleotide is an antisense RNA that is complementary to an mRNA. In some embodiments, the polynucleotide is a long non-coding RNA (lncRNA) capable of regulating gene expression and modulating diseases. In some embodiments, the polynucleotide is an antisense oligonucleotide (ASO). In various embodiments, the ASO is a single-stranded or double-stranded DNA, RNA, or DNA/RNA hybrid. See, e.g., Antisense Oligodeoxynucleotides and Antisense RNA: Novel Pharmacological and Therapeutic Agents, CRC Press, Boca Raton, Fla., 1997, incorporated herein by reference for all purposes.

In some embodiments, the polynucleotide is a DNA that can be transcribed into an RNA. In some of these embodiments, the transcribed RNA can be translated into a desired polypeptide. In certain embodiments, the nucleic acid inhibits at least one gene consisting of: KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, CEBP/β, Pi3Kγ, Glutaminase, and PKM2. In certain embodiments, the nucleic acid inhibits at least one gene consisting of: STAT3, STAT6, CEBP/β, Pi3Kγ, KRAS, and HIF1-alpha. In certain embodiments, the nucleic acid is an inhibitory RNA that inhibits at least one gene consisting of: KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, CEBP/β, Pi3Kγ, Glutaminase, and PKM2. In certain embodiments, the nucleic acid is an inhibitory RNA that inhibits at least one gene consisting of: STAT3, STAT6, CEBP/β, Pi3Kγ, KRAS, and HIF1-alpha. In certain embodiments, the nucleic acid is an antisense oligonucleotide (ASO) that inhibits at least one gene consisting of: KRAS, HRAS, NRAS, HIF1-alpha, HIF1-beta, Sp1, P300, LKB1, AMPK, STAT3, STAT6, n-MYC, c-MYC, HCAR1, A2AB, IDO, TDO, Arginase, CEBP/β, Pi3Kγ, Glutaminase, and PKM2. In certain embodiments, the nucleic acid is an antisense oligonucleotide (ASO) that inhibits at least one gene consisting of: STAT3, STAT6, CEBP/β, Pi3Kγ, KRAS, and HIF1-alpha. In certain embodiments, the nucleic acid inhibits the human KRAS proto-oncogene. In certain embodiments, the nucleic acid is an inhibitory RNA that inhibits the human KRAS proto-oncogene. In certain embodiments, the nucleic acid inhibits STAT3.

In some embodiments of the present invention, the nucleic acid is a known antisense oligonucleotide (ASO), examples of which are listed in Table 0. In certain embodiments the ASO comprises a sequence at least 90% to 99% identical to a known ASO, e.g., those listed in Table 0. In certain embodiments the ASO inhibits STAT3. In various embodiments, the ASO comprises a sequence at least 90% to 99% identical to TAAGCTGATAATTCAACTCA (SEQ ID NO:1). In certain embodiments, the ASO comprises a sequence at least 90% identical to SEQ ID NO:1. In certain embodiments, the ASO comprises a sequence at least 91% identical to SEQ ID NO:1. In certain embodiments, the ASO comprises a sequence at least 92% identical to SEQ ID NO:1. In certain embodiments, the ASO comprises a sequence at least 93% identical to SEQ ID NO:1. In certain embodiments, the ASO comprises a sequence at least 94% identical to SEQ ID NO:1. In certain embodiments, the ASO comprises a sequence at least 95% identical to SEQ ID NO:1. In certain embodiments, the ASO comprises a sequence at least 96% identical to SEQ ID NO:1. In certain embodiments, the ASO comprises a sequence at least 97% identical to SEQ ID NO:1. In certain embodiments, the ASO comprises a sequence at least 98% identical to SEQ ID NO:1. In certain embodiments, the ASO comprises a sequence at least 99% identical to SEQ ID NO:1. In certain embodiments, the ASO comprises a sequence of SEQ ID NO:1. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits STAT6. In various embodiments, the ASO comprises a sequence at least 90% to 99% identical to TGAGCGAATGGACAGGTCTT (SEQ ID NO:2). In certain embodiments, the ASO comprises a sequence at least 90% identical to SEQ ID NO:2. In certain embodiments, the ASO comprises a sequence at least 91% identical to SEQ ID NO:2. In certain embodiments, the ASO comprises a sequence at least 92% identical to SEQ ID NO:2. In certain embodiments, the ASO comprises a sequence at least 93% identical to SEQ ID NO:2. In certain embodiments, the ASO comprises a sequence at least 94% identical to SEQ ID NO:2. In certain embodiments, the ASO comprises a sequence at least 95% identical to SEQ ID NO:2. In certain embodiments, the ASO comprises a sequence at least 96% identical to SEQ ID NO:2. In certain embodiments, the ASO comprises a sequence at least 97% identical to SEQ ID NO:2. In certain embodiments, the ASO comprises a sequence at least 98% identical to SEQ ID NO:2. In certain embodiments, the ASO comprises a sequence at least 99% identical to SEQ ID NO:2. In certain embodiments, the ASO comprises a sequence of SEQ ID NO:2. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits CebpB. In various embodiments, the ASO comprises a sequence at least 90% to 99% identical to TGGATTTAAAGGCAGGCGGC (SEQ ID NO:3). In certain embodiments, the ASO comprises a sequence at least 90% identical to SEQ ID NO:3. In certain embodiments, the ASO comprises a sequence at least 91% identical to SEQ ID NO:3. In certain embodiments, the ASO comprises a sequence at least 92% identical to SEQ ID NO:3. In certain embodiments, the ASO comprises a sequence at least 93% identical to SEQ ID NO:3. In certain embodiments, the ASO comprises a sequence at least 94% identical to SEQ ID NO:3. In certain embodiments, the ASO comprises a sequence at least 95% identical to SEQ ID NO:3. In certain embodiments, the ASO comprises a sequence at least 96% identical to SEQ ID NO:3. In certain embodiments, the ASO comprises a sequence at least 97% identical to SEQ ID NO:3. In certain embodiments, the ASO comprises a sequence at least 98% identical to SEQ ID NO:3. In certain embodiments, the ASO comprises a sequence at least 99% identical to SEQ ID NO:3. In certain embodiments, the ASO comprises a sequence of SEQ ID NO:3. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits Pi3Kγ. In various embodiments, the ASO comprises a sequence at least 90% to 99% identical to TTGGGTAAAGTCGTGCAGCA (SEQ ID NO:4). In certain embodiments, the ASO comprises a sequence at least 90% identical to SEQ ID NO:4. In certain embodiments, the ASO comprises a sequence at least 91% identical to SEQ ID NO:4. In certain embodiments, the ASO comprises a sequence at least 92% identical to SEQ ID NO:4. In certain embodiments, the ASO comprises a sequence at least 93% identical to SEQ ID NO:4. In certain embodiments, the ASO comprises a sequence at least 94% identical to SEQ ID NO:4. In certain embodiments, the ASO comprises a sequence at least 95% identical to SEQ ID NO:4. In certain embodiments, the ASO comprises a sequence at least 96% identical to SEQ ID NO:4. In certain embodiments, the ASO comprises a sequence at least 97% identical to SEQ ID NO:4. In certain embodiments, the ASO comprises a sequence at least 98% identical to SEQ ID NO:4. In certain embodiments, the ASO comprises a sequence at least 99% identical to SEQ ID NO:4. In certain embodiments, the ASO comprises a sequence of SEQ ID NO:4. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits HIF1α. In various embodiments, the ASO comprises a sequence at least 90% to 99% identical to SEQ ID NO:5. In certain embodiments, the ASO comprises a sequence at least 90% identical to SEQ ID NO:5. In certain embodiments, the ASO comprises a sequence at least 91% identical to SEQ ID NO:5. In certain embodiments, the ASO comprises a sequence at least 92% identical to SEQ ID NO:5. In certain embodiments, the ASO comprises a sequence at least 93% identical to SEQ ID NO:5. In certain embodiments, the ASO comprises a sequence at least 94% identical to SEQ ID NO:5. In certain embodiments, the ASO comprises a sequence at least 95% identical to SEQ ID NO:5. In certain embodiments, the ASO comprises a sequence at least 96% identical to SEQ ID NO:5. In certain embodiments, the ASO comprises a sequence at least 97% identical to SEQ ID NO:5. In certain embodiments, the ASO comprises a sequence at least 98% identical to SEQ ID NO:5. In certain embodiments, the ASO comprises a sequence at least 99% identical to SEQ ID NO:5. In certain embodiments, the ASO comprises a sequence of SEQ ID NO:5. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits HIF1α. In various embodiments, the ASO comprises a sequence at least 90% to 99% identical to GTGCAGTATTGTAGCCAGGC (SEQ ID NO:5). In certain embodiments, the ASO comprises a sequence at least 90% identical to SEQ ID NO:5. In certain embodiments, the ASO comprises a sequence at least 91% identical to SEQ ID NO:5. In certain embodiments, the ASO comprises a sequence at least 92% identical to SEQ ID NO:5. In certain embodiments, the ASO comprises a sequence at least 93% identical to SEQ ID NO:5. In certain embodiments, the ASO comprises a sequence at least 94% identical to SEQ ID NO:5. In certain embodiments, the ASO comprises a sequence at least 95% identical to SEQ ID NO:5. In certain embodiments, the ASO comprises a sequence at least 96% identical to SEQ ID NO:5. In certain embodiments, the ASO comprises a sequence at least 97% identical to SEQ ID NO:5. In certain embodiments, the ASO comprises a sequence at least 98% identical to SEQ ID NO:5. In certain embodiments, the ASO comprises a sequence at least 99% identical to SEQ ID NO:5. In certain embodiments, the ASO comprises a sequence of SEQ ID NO:5. In some embodiments, the ASO is modified by MOE, O-methyl, or LNA chemistry. In some embodiments, the ASO further comprises a cholesterol tag at the 5' or 3' end.

In some embodiment, the nucleic acid is an antisense oligonucleotide (ASO) that inhibits Kras. In various embodiments, the ASO comprises a sequence at least 90% to 99% identical to GTAGCATGTAAATATAGCCC (SEQ ID NO:6). In certain embodiments, the ASO comprises a sequence at least 90% identical to SEQ ID NO:6. In certain embodiments, the ASO comprises a sequence at least 91% identical to SEQ ID NO:6. In certain embodiments, the ASO comprises a sequence at least 92% identical to SEQ ID NO:6. In certain embodiments, the ASO comprises a sequence at least 93% identical to SEQ ID NO:6. In certain embodiments, the ASO comprises a sequence at least 94% identical to SEQ ID NO:6. In certain embodiments, the ASO comprises a sequence at least 95% identical to SEQ ID NO:6. In certain embodiments, the ASO comprises a sequence at least 96% identical to SEQ ID NO:6. In certain embodiments, the ASO comprises a sequence at least 97% identical to SEQ ID NO:6. In certain embodiments, the ASO comprises a sequence at least 98% identical to SEQ ID NO:6. In certain embodiments, the ASO comprises a sequence at least 99% identical to SEQ ID NO:6. In certain embodiments, the ASO comprises a sequence of SEQ ID NO:6. In some embodiments, the ASO is modified by MOE, O-methyl, or LNA chemistry. In some embodiments, the ASO further comprises a cholesterol tag at the 5' or 3' end.

In certain embodiments, the composition comprises an extracellular vesicle, e.g., an exosome, further comprising an additional immunomodulating component that is a small molecule, antibody or antibody fragment known to promote macrophage polarization. In certain embodiments, the additional immunomodulating component is a Colony Stimulating Factor 1 Receptor (CSF1R) inhibitor.

In certain embodiments, the composition comprises an additional immunomodulating component that has anti-tumor activity. In some embodiments, the additional immunomodulating component regulates the innate immune response. In some of these embodiments, the additional immunomodulating component targets the natural killer cells. In some other embodiments, the additional immunomodulating component regulates the adaptive immune response. In some of these embodiments, the additional immunomodulating component targets the cytotoxic T cells.

In some embodiments, the additional immunomodulating component is located on the surface of the extracellular vesicle. In some embodiments, the additional immunomodulating component is located inside the extracellular vesicle. In some embodiments, the additional immunomodulating component is located both on the surface of and inside the extracellular vesicle.

In some embodiments, the additional immunomodulating component is expressed in the producer cell in its full-length form. In other embodiments, the additional immunomodulating component is expressed as a translational fusion protein to an exosome surface protein, which results in a higher level of expression of the biologically active portion of the immunomodulating compound on the surface of the exosome. In some embodiments, the additional immunomodulating compound is a soluble protein that is expressed as a translational fusion protein to an exosome surface protein, such that said soluble protein is retained on the surface of the exosome.

In some embodiments, the additional immunomodulating component is an inhibitor for a negative checkpoint regulator, such as, e.g., A2AR, B7-H3 (CD276), B7-H4 (VTCN1), BTLA, CTLA-4, IDO, KIR, LAG3, NOX2, PD-1, TIM-3, VISTA, SIGLEC7 (CD328) and SIGLEC9 (CD329). In some embodiments, the additional immunomodulating component is an inhibitor for a binding partner of a negative checkpoint regulator, such as, e.g., PD-L1 and PD-L2.

In certain embodiments, the additional immunomodulating component is an inhibitor of cytotoxic T-lymphocyte-associate protein 4 (CTLA-4). In some of these embodiments, the CTLA-4 inhibitor is a monoclonal antibody of CTLA-4. In certain embodiments, the inhibitor is a fragment of a monoclonal antibody of CTLA-4. In certain embodiments, the antibody fragment is a scFv, (scFv)$_2$, Fab, Fab', and F(ab')$_2$, F(ab1)$_2$, Fv, dAb, or Fd of a monoclonal antibody of CTLA-4. In certain embodiments, the inhibitor is a nanobody, a bispecific antibody, or a multispecific antibody against CTLA-4. In some specific embodiments, the monoclonal antibody is ipilimumab. In some specific embodiments, the monoclonal antibody is tremelimumab.

In certain embodiments, the additional immunomodulating component is an inhibitor of programmed cell death protein 1 (PD-1). In certain embodiments, the additional immunomodulating component is an inhibitor of programmed death-ligand 1 (PD-L1). In certain embodiments, the additional immunomodulating component is an inhibitor of programmed death-ligand 2 (PD-L2). In some embodiments, the inhibitor of PD-1, PD-L1, or PD-L2 is a monoclonal antibody of PD-1, PD-L1, or PD-L2. In certain embodiments, the inhibitor is a fragment of a monoclonal antibody of PD-1, PD-L1, or PD-L2. In certain embodiments, the antibody fragment is a scFv, (scFv)$_2$, Fab, Fab', and F(ab')$_2$, F(ab1)$_2$, Fv, dAb, or Fd of a monoclonal antibody of PD-1, PD-L1, or PD-L2. In certain embodiments, the inhibitor is a nanobody, a bispecific antibody, or a multispecific antibody against PD-1, PD-L1, or PD-L2. In some specific embodiments, the monoclonal antibody is nivolumab. In some specific embodiments, the monoclonal antibody is pembrolizumab. In some specific embodiments, the monoclonal antibody is pidilizumab. In some specific embodiments, the monoclonal antibody is atezolizumab. In some specific embodiments, the monoclonal antibody is avelumab.

In certain embodiments, the additional immunomodulating component is an inhibitor of lymphocyte-activated gene 3 (LAG3). In some of these embodiments, the inhibitor of LAG3 is a monoclonal antibody of LAG3, such as, e.g., BMS-986016 (see Clinical trial number NCT01968109 for "Safety Study of Anti-LAG-3 With and Without Anti-PD-1 in the Treatment of Solid Tumors" at ClinicalTrials.gov).

In certain embodiments, the additional immunomodulating component is an inhibitor of T-cell immunoglobulin mucin-containing protein 3 (TIM-3). In certain embodiments, the additional immunomodulating component is an inhibitor of B and T lymphocyte attenuator (BTLA). In certain embodiments, the additional immunomodulating component is an inhibitor of T cell immunoreceptor with Ig and ITIM domains (TIGIT). In certain embodiments, the additional immunomodulating component is an inhibitor of V-domain Ig suppressor of T cell activation (VISTA). In certain embodiments, the additional immunomodulating component is an inhibitor of adenosine A2a receptor (A2aR). In certain embodiments, the additional immunomodulating component is an inhibitor of killer cell immunoglobulin like receptor (KIR). In certain embodiments, the additional immunomodulating component is an inhibitor of indoleamine 2,3-dioxygenase (IDO). In certain embodiments, the additional immunomodulating component is an inhibitor of CD20, CD39, or CD73.

In some embodiments, the additional immunomodulating component is an activator for a positive co-stimulatory molecule. In some embodiments, the additional immunomodulating component is an activator for a binding partner of a positive co-stimulatory molecule.

In some embodiments, the additional immunomodulating component is an activator of a TNF receptor superfamily member, such as an agonistic antibody or a natural ligand or a TNF receptor superfamily member. In certain embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, GITR, TROY, CD358, TRAMP, and XEDAR. In some embodiments, the additional immunomodulating component is a TNF superfamily member. In certain embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2.

In certain embodiments, the additional immunomodulating component is an activator of TNF Receptor Superfamily Member 4 (OX40). In some of these embodiments, the activator of OX40 is an agonist antibody of OX40. In some other of these embodiments, the activator of OX40 is OX40 ligand (OX40L).

In certain embodiments, the additional immunomodulating component is an activator of CD27. In some of these embodiments, the activator of CD27 is an agonist antibody of CD27. In some other of these embodiments, the activator of CD27 is CD27 ligand (CD27L).

In certain embodiments, the additional immunomodulating component is an activator of CD40. In some of these embodiments, the activator of CD40 is an agonist antibody of CD40. In some other of these embodiments, the activator of CD40 is CD40 ligand (CD40L).

In certain embodiments, the additional immunomodulating component is an activator of glucocorticoid-induced TNFR-related protein (GITR). In some of these embodiments, the activator of GITR is an agonist antibody of GITR. In some other of these embodiments, the activator of GITR is a natural ligand of GITR.

In certain embodiments, the additional immunomodulating component is an activator of 4-1BB. In some of these embodiments, the activator of 4-1BB is an agonist antibody of 4-1BB. In some other of these embodiments, the activator of 4-1BB is a natural ligand of 4-1BB.

In some embodiments, the additional immunomodulating component is Fas receptor (Fas). In some of these embodiments, the Fas receptor is displayed on the surface of the extracellular vesicle. In some other embodiments, the additional immunomodulating component is Fas ligand (FasL). In some of these embodiments, the Fas ligand is displayed on the surface of the extracellular vesicle. In certain embodiments, the additional immunomodulating component is an antibody of Fas receptor. In certain embodiments, the additional immunomodulating component is an antibody of Fas ligand.

In some embodiments, the additional immunomodulating component is an activator of a CD28-superfamily co-stimulatory molecule. In certain embodiments, the CD28-superfamily co-stimulatory molecule is ICOS or CD28. In certain embodiments, the additional immunomodulating component is ICOSL, CD80, or CD86.

In certain embodiments, the additional immunomodulating component is an activator of inducible T cell co-stimulator (ICOS). In some of these embodiments, the activator of ICOS is an agonist antibody of ICOS. In some other of these embodiments, the activator of ICOS is ICOS ligand (ICOSL).

In certain embodiments, the additional immunomodulating component is an activator of CD28. In some of these embodiments, the activator of CD28 is an agonist antibody of CD28. In some other of these embodiments, the activator of CD28 is a natural ligand of CD28. In certain embodiments, the ligand of CD28 is CD80.

In certain embodiments, the additional immunomodulating component is a cytokine. In some embodiments, the cytokine is a soluble cytokine that has been translationally fused to an exosome surface protein or fragment thereof. In some embodiments, the cytokine is IL-2. In some embodiments, the cytokine is IL-7. In some embodiments, the cytokine is IL-12. In some embodiments, the cytokine is IL-15.

In some embodiments, the additional immunomodulating component is a T-cell receptor (TCR) or a derivative thereof. In certain embodiments, the additional immunomodulating component is a TCR α-chain or a derivative thereof. In certain embodiments, the additional immunomodulating component is a TCR β-chain or a derivative thereof. In some embodiments, the additional immunomodulating component is a co-receptor of the T-cell or a derivative thereof.

In some embodiments, the additional immunomodulating component is a tumor antigen. In certain embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In certain embodiments, the tumor antigen is a carcinoembryonic antigen (CEA). In certain embodiments, the tumor antigen is an epithelial tumor antigen (ETA).

In certain embodiments, the tumor antigen is a mucin. In some of these embodiments, the mucin is a secreted mucin. In some other of these embodiments, the mucin is a transmembrane mucin. In specific embodiments, the tumor antigen is mucin 1 (MUC1). In specific embodiments, the tumor antigen is Tn-MUC1. In specific embodiments, the tumor antigen is mucin 16 (MUC16).

In certain embodiments, the tumor antigen is a melanoma-associated antigen (MAGE). In some of these embodiments, the MAGE is a type-I MAGE. In some other of these embodiments, the MAGE is a type-II MAGE. In specific embodiments, the type-I MAGE is MAGE-A2. In specific embodiments, the type-I MAGE is MAGE-A4.

In certain embodiments, the tumor antigen is alpha-fetoprotein (AFP). In certain embodiments, the tumor antigen is tumor protein p53 (p53). In certain embodiments, the tumor antigen is tyrosinase. In certain embodiments, the tumor antigen is a tyrosinase-related protein (TRP). In some embodiments, the tumor antigen is programmed death ligand 1 (PD-L1) or programmed death ligand 2 (PD-L2). In various embodiments, the tumor antigen is selected from the group consisting of CD4, CD8, CD45, CD80, and CD86.

In some embodiments, the immunomodulating component is a chimeric antigen receptor (CAR) or a derivative thereof. In some embodiments, the CAR binds to one or more of alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In some embodiments, the additional immunomodulating component is an activator of a T-cell receptor or co-receptor. In certain embodiments, the additional immunomodulating component is an activator of CD3. In certain embodiments, the activator is a fragment of a monoclonal antibody of CD3. In certain embodiments, the antibody fragment is a scFv, $(scFv)_2$, Fab, Fab', and $F(ab')_2$, $F(ab1)_2$, Fv, dAb, or Fd of a monoclonal antibody of CD3. In certain embodiments, the activator is a nanobody, a bispecific antibody, or a multi-specific antibody against CD3. In certain embodiments, the additional immunomodulating component is an activator of CD28. In certain embodiments, the activator is a fragment of a monoclonal antibody of CD28. In certain embodiments, the antibody fragment is a scFv, $(scFv)_2$, Fab, Fab', and $F(ab')_2$, $F(ab1)_2$, Fv, dAb, or Fd of a monoclonal antibody of CD28. In certain embodiments, the activator is a nanobody, a bispecific antibody, or a multispecific antibody against CD28.

In some embodiments, the additional immunomodulating component is a major histocompatibility complex (MHC) or a derivative thereof. In some of these embodiments, the additional immunomodulating component is an MHC class I or a derivative thereof. In some of these embodiments, the additional immunomodulating component is an MHC class II or a derivative thereof. In some of these embodiments, the additional immunomodulating component is an MHC class III or a derivative thereof.

In some embodiments, the additional immunomodulating component is a human leukocyte antigen (HLA) or a derivative thereof. In some of these embodiments, the additional immunomodulating component is an HLA-A, HLA-B, HLA-C, or derivative thereof. In some of these embodiments, the additional immunomodulating component is an HLA-E, HLA-F, HLA-G, or a derivative thereof. In some of these embodiments, the additional immunomodulating component is an HLA-DP, HLA-DQ, HLA-DR, or a derivative thereof.

In various embodiments, the immunomodulating component can be a polypeptide, a polynucleotide, a polysaccharide, a lipid, a small molecule, or a toxin.

In some embodiments, the immunomodulating component can be a protein, a peptide, a glycolipid, or a glycoprotein.

In certain embodiments, the immunomodulating component is an agonist. In some of these embodiments, the agonist is an endogenous agonist, such as a hormone, or a neurotransmitter. In some other of these embodiments, the agonist is an exogenous agonist, such as a drug. In some embodiments, the agonist is a physical agonist, which can create an agonist response without binding to the receptor. In some embodiments, the agonist is a superagonist, which can produce a greater maximal response than the endogenous agonist. In certain embodiments, the agonist is a full agonist with full efficacy at the receptor. In certain other embodiments, the agonist is a partial agonist having only partial efficacy at the receptor relative to a full agonist. In some embodiments, the agonist is an inverse agonist that can inhibit the constitutive activity of the receptor. In some embodiments, the agonist is a co-agonist that works with other co-agonists to produce an effect on the receptor. In certain embodiments, the agonist is an irreversible agonist that binds permanently to a receptor through formation of covalent bond. In certain embodiments, the agonist is selective agonist for a specific type of receptor.

In certain embodiments, the immunomodulating component is an antagonist. In some of these embodiments, the antagonist is a competitive antagonist, which reversibly binds to the receptor at the same binding site as the endogenous ligand or agonist without activating the receptor. Competitive antagonist can affect the amount of agonist necessary to achieve a maximal response. In some other of these embodiments, the antagonist is a non-competitive antagonist, which binds to an active site of the receptor or an allosteric site of the receptor. Non-competitive antagonist can reduce the magnitude of the maximum response that can be attained by any amount of agonist. In some other embodiments, the antagonist is an uncompetitive antagonist, which requires receptor activation by an agonist before its binding to a separate allosteric binding site.

In various embodiments, the immunomodulating component comprises an antibody or an antigen-binding fragment. The immunomodulating component can be a full length protein or a fragment thereof. The antibody or antigen-binding fragment can be derived from natural sources, or partly or wholly synthetically produced. In some embodiments, the antibody is a monoclonal antibody. In some of these embodiments, the monoclonal antibody is an IgG antibody. In certain embodiments, the monoclonal antibody is an IgG1, IgG2, IgG3, or IgG4. In some other embodiments, the antibody is a polyclonal antibody. In certain embodiments, the antigen-binding fragment is selected from Fab, Fab', and $F(ab')_2$, $F(ab1)_2$, Fv, dAb, and Fd fragments. In certain embodiments, the antigen-binding fragment is an scFv or $(scFv)_2$ fragment. In certain other embodiments, the antibody or antigen-binding fragment is a Nanobody® (single-domain antibody). In some embodiments, the antibody or antigen-binding fragment is a bispecific or multispecific antibody.

In various embodiments, the antibody or antigen-binding fragment is fully human. In some embodiments, the antibody or antigen-binding fragment is humanized. In some embodiments, the antibody or antigen-binding fragment is chimeric. In some of these embodiments, the chimeric antibody has non-human V region domains and human C region domains. In some embodiments, the antibody or antigen-binding fragment is non-human, such as murine or veterinary.

In some embodiments, the immunomodulating component is a protein, a peptide, a glycolipid, or a glycoprotein.

In various embodiments, the composition comprises two or more above mentioned immunomodulating components, including mixtures, fusions, combinations and conjugates, of atoms, molecules, etc. In certain embodiments, the composition comprises a nucleic acid combined with a polypeptide. In certain embodiments, the composition comprises two or more polypeptides conjugated to each other. In certain embodiments, the composition comprises a protein conjugated to a biologically active molecule. In some of these embodiments, the biologically active molecule is a prodrug.

The Pharmaceutical Composition

The pharmaceutical compositions generally comprise a plurality of extracellular vesicles and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some embodiments, the pharmaceutical composition comprises one or more therapeutic agents and the extracellular vesicle described herein. In some embodiments, the extracellular vesicles are co-administered with of one or more separate therapeutic agents, wherein co-administration includes administration of the separate therapeutic agent before, after or concurrent with administration of the extracellular vesicles.

Pharmaceutically-acceptable excipients include excipients that are generally safe, non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The extracellular vesicles can be administered by parenteral, topical, intravenous, oral, subcutaneous, intra-arterial, intradermal, transdermal, rectal, intracranial, intraperitoneal, intranasal, intramuscular route or as inhalants. In certain embodiments, the pharmaceutical composition comprising extracellular vesicles is administered intravenously, e.g., by injection. The extracellular vesicles can optionally be administered in combination with other therapeutic agents that are at least partly effective in treating the disease, disorder or condition for which the extracellular vesicles are intended.

Solutions or suspensions can include the following components: a sterile diluent such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as manitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the extracellular vesicles in an effective amount and in an appropriate solvent with one or a combination of ingredients enumerated herein, as desired. Generally, dispersions are prepared by incorporating the extracellular vesicles into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The extracellular vesicles can be administered in the form of a depot injection or implant preparation which can be formulated in such a manner to permit a sustained or pulsatile release of the extracellular vesicles.

Systemic administration of compositions comprising extracellular vesicles can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain embodiments the pharmaceutical composition comprising extracellular vesicles is administered intravenously into a subject that would benefit from the pharmaceutical composition. In certain other embodiments, the composition is administered to the lymphatic system, e.g., by intralymphatic injection or by intranodal injection (see e.g., Senti et al., PNAS 105(46): 17908 (2008)), or by intramuscular injection, by subcutaneous administration, by direct injection into the thymus, or into the liver.

In certain embodiments, the pharmaceutical composition comprising extracellular vesicles is administered as a liquid suspension. In certain embodiments, the pharmaceutical composition is administered as a formulation that is capable of forming a depot following administration. In certain preferred embodiments, the depot slowly releases the extracellular vesicles into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the extracellular vesicles described herein and optionally a pharmaceutically active or therapeutic agent. The therapeutic agent can be a biological agent, a small molecule agent, or a nucleic acid agent.

Dosage forms are provided that comprise a pharmaceutical composition comprising the extracellular vesicles described herein. In some embodiments, the dosage form is formulated as a liquid suspension for intravenous injection.

In certain embodiments, the preparation of extracellular vesicles is subjected to radiation, e.g., X rays, gamma rays, beta particles, alpha particles, neutrons, protons, elemental nuclei, UV rays in order to damage residual replication-competent nucleic acids.

In certain embodiments, the preparation of extracellular vesicles is subjected to gamma irradiation using an irradiation dose of more than 1, 5, 10, 15, 20, 25, 30, 35, 40, 50, 60, 70, 80, 90, 100, or more than 100 kGy.

In certain embodiments, the preparation of extracellular vesicles is subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

Methods

Aspects of the subject disclosure also include methods of producing the composition comprising the extracellular vesicle and the immunomodulating component. In some embodiments, the method comprises: obtaining the extracellular vesicle from the producer cell, wherein the producer cell naturally contains the immunomodulating component; and optionally isolating the obtained extracellular vesicle. In some embodiments, the method comprises: modifying a producer cell with the immunomodulating component; obtaining the extracellular vesicle from the modified producer cell; and optionally isolating the obtained extracellular vesicles. In some other embodiments, the method comprises: obtaining the extracellular vesicle from a producer cell; isolating the obtained extracellular vesicles; and modifying the isolated extracellular vesicle with the immunomodulating component. In certain embodiments, the method further comprises formulating the isolated extracellular vesicles into a pharmaceutical composition.

Methods of Producing the Extracellular Vesicles
Methods of Modifying the Producer Cell with the Immunomodulating Component In various embodiments, the method comprises modifying a producer cell with the immunomodulating component.

The producer cell can be a mammalian cell line, a plant cell line, an insect cell line, a fungi cell line, or a prokaryotic cell line. In certain embodiments, the producer cell is a mammalian cell line. The mammalian cell lines include but are not limited to a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, and a mesenchymal stem cell (MSC) cell line. In some preferred embodiments, the mammalian cell line can be HEK-293 cells, BJ human foreskin fibroblast cells, fHDF fibroblast cells, AGE.HN® neuronal precursor cells, CAP® amniocyte cells, adipose mesenchymal stem cells, or RPTEC/TERT1 cells. The producer cell can also be a primary cell. In various embodiments, the primary cell can be a primary mammalian cell, a primary plant cell, a primary insect cell, a primary fungi cell, or a primary prokaryotic cell.

In certain preferred embodiments, the producer cell is an immune cell, such as a dendritic cell, a T cell, a B cell, a natural killer cell (NK cell), an antigen presenting cell, a macrophage, a T helper cell, or a regulatory T cell (Treg cell).

In various embodiments, the immunomodulating component can be expressed in a producer cell from a transgene or mRNA introduced into the producer cell by transfection (see, e.g., Bacchetti S, Graham F L (April 1977). "Transfer of the gene for thymidine kinase to thymidine kinase-deficient human cells by purified herpes simplex viral DNA". *Proceedings of the National Academy of Sciences of the United States of America.* 74 (4): 1590-4; Kriegler M (1991). Transfer and Expression: A Laboratory Manual. W. H. Freeman. pp. 96-97; Felgner P L, Gadek T R, Holm M, Roman R, Chan H W, Wenz M, Northrop J P, Ringold G M, Danielsen M (November 1987). "Lipofection: a highly efficient, lipid-mediated DNA-transfection procedure". *Proceedings of the National Academy of Sciences of the United States of America.* 84 (21): 7413-7; Felgner J H, Kumar R, Sridhar C N, Wheeler C J, Tsai Y J, Border R, Ramsey P, Martin M, Felgner P L (January 1994). "Enhanced gene delivery and mechanism studies with a novel series of cationic lipid formulations". *The Journal of Biological Chemistry.* 269 (4): 2550-61), viral transduction (see, e.g., Griffiths A J, Miller J H, Suzuki D T, Lewontin R C, Gelbart W M (2000). "*Transduction*". An Introduction to Genetic Analysis (7th ed.)), electroporation (see, e.g., Neumann, E; Schaefer-Ridder, M; Wang, Y; Hofschneider, P H (1982). "Gene transfer into mouse lyoma cells by electroporation in high electric fields". *The EMBO Journal.* 1 (7): 841-5)) extrusion (see, e.g., Sharei A, Zoldan J, Adamo A, Sim W Y, Cho N, Jackson E, Mao S, Schneider S, Han M J, Lytton-Jean A, Basto P A, Jhunjhunwala S, Lee J, Heller D A, Kang J W, Hartoularos G C, Kim K S, Anderson D G, Langer R, Jensen K F (February 2013). "A vector-free microfluidic platform for intracellular delivery". *Proceedings of the National Academy of Sciences of the United States of America.* 110 (6): 2082-7), sonication (see, e.g., Yizhi Song (2007). "Ultrasound-mediated DNA transfer for bacteria". *Nucleic Acids Res.* 35 (19): e129.), cell fusion (see, e.g., Felgner P L, Gadek T R, Holm M, Roman R, Chan H W, Wenz M, Northrop J P, Ringold G M, Danielsen M (November 1987). "Lipofection: a highly efficient, lipid-mediated DNA-transfection procedure". *Proceedings of the National Academy of Sciences of the United States of America.* 84 (21): 7413-), or other methods that are known to the skilled in the art.

In certain embodiments, the immunomodulating component is introduced to the producer cell by transfection. In some embodiments, the immunomodulating component can be introduced into suitable producer cells using synthetic macromolecules such as cationic lipids and polymers (Papapetrou et al., Gene Therapy 12: S118-S130 (2005)). In some embodiments, the cationic lipids form complexes with the immunomodulating component through charge interactions. In some of these embodiments, the positively charged complexes bind to the negatively charged cell surface and are taken up by the cell by endocytosis. In some other embodiments, a cationic polymer can be used to transfect producer cells. In some of these embodiments, the cationic polymer is polyethylenimine (PEI). In certain embodiments, chemicals such as calcium phosphate, cyclodextrin, or polybrene, can be used to introduce the immunomodulating component to the producer cells. The immunomodulating component can also be introduced into a producer cell using a physical method such as particle-mediated transfection, "gene gun," biolistics, or particle bombardment technology (Papapetrou et al., Gene Therapy 12: S118-S130 (2005)). A reporter gene such as, for example, beta-galactosidase, chloramphenicol acetyltransferase, luciferase, or green fluorescent protein can be used to assess the transfection efficiency of the producer cell.

In certain embodiments, the immunomodulating component is introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain embodiments, the immunomodulating component is introduced to the producer cell by electroporation. Electroporation creates transient pores in the cell membrane, allowing for the introduction of various molecules into the cell. In some embodiments, DNA and RNA as well as polypeptides and non-polypeptide therapeutic agents can be introduced into the producer cell by electroporation.

In certain embodiments, the immunomodulating component is introduced to the producer cell by microinjection. In some embodiments, a glass micropipette can be used to inject the immunomodulating component into the producer cell at the microscopic level.

In certain embodiments, the immunomodulating component is introduced to the producer cell by extrusion.

In certain embodiments, the immunomodulating component is introduced to the producer cell by sonication. In some embodiments, the producer cell is exposed to high intensity sound waves, causing transient disruption of the cell membrane allowing loading of an immunomodulating component.

In certain embodiments, the immunomodulating component is introduced to the producer cell by cell fusion. In some embodiments, the immunomodulating component is introduced by electrical cell fusion. In some other embodiments, polyethylene glycol (PEG) is used to fuse the producer cells. In some other embodiments, sendai virus is used to fuse the producer cells.

In some embodiments, the immunomodulating component is introduced to the producer cell by hypotonic lysis. In some of these embodiments, the producer cell is exposed to low ionic strength buffer causing them to burst allowing loading of an immunomodulating component. In some alternative embodiments, controlled dialysis against a hypotonic solution is used to swell the producer cell and to create pores in the producer cell membrane. The producer cell is subsequently exposed to conditions that allow resealing of the membrane.

In some embodiments, the immunomodulating component is introduced to the producer cell by detergent treatment. In certain embodiments, producer cell is treated with a mild detergent which transiently compromises the producer cell membrane by creating pores allowing loading of an immunomodulating component. After producer cells are loaded, the detergent is washed away thereby resealing the membrane.

In some embodiments, the immunomodulating component is introduced to the producer cell by receptor mediated endocytosis. In certain embodiments, producer cells have a surface receptor which upon binding of the immunomodulating component induces internalization of the receptor and the associated immunomodulating component.

In some embodiments, the immunomodulating component is introduced to the producer cell by filtration. In certain embodiments, the producer cells and the immunomodulating component can be forced through a filter of pore size smaller than the producer cell causing transient disruption of the producer cell membrane and allowing the immunomodulating component to enter the producer cell.

In some embodiments, the producer cell is subjected to several freeze thaw cycles, resulting in cell membrane disruption allowing loading of an immunomodulating component.

Methods of Modifying the Extracellular Vesicle with the Immunomodulating Component In various alternative embodiments, the immunomodulating component is introduced directly to the extracellular vesicles after the isolation of the extracellular vesicles.

In certain embodiments, the immunomodulating component is introduced to the extracellular vesicle by transfection. In some embodiments, the immunomodulating component can be introduced into the extracellular vesicles using synthetic macromolecules such as cationic lipids and polymers (Papapetrou et al., Gene Therapy 12: S118-S130 (2005)). In certain embodiments, chemicals such as calcium phosphate, cyclodextrin, or polybrene, can be used to introduce the immunomodulating component to the extracellular vesicles.

In certain embodiments, the immunomodulating component is introduced to the extracellular vesicle by electroporation. In some embodiments, extracellular vesicles are exposed to an electrical field which causes transient holes in the extracellular vesicle membrane, allowing loading of an immunomodulating component.

In certain embodiments, the immunomodulating component is introduced to the extracellular vesicle by microinjection. In some embodiments, a glass micropipette can be used to inject the immunomodulating component directly into the extracellular vesicle at the microscopic level.

In certain embodiments, the immunomodulating component is introduced to the extracellular vesicle by extrusion.

In certain embodiments, the immunomodulating component is introduced to the extracellular vesicle by sonication.

In some embodiments, extracellular vesicles are exposed to high intensity sound waves, causing transient disruption of the extracellular vesicle membrane allowing loading of an immunomodulating component.

In some embodiments, the immunomodulating component can be conjugated to the surface of the extracellular vesicle. Conjugation can be achieved chemically or enzymatically, by methods known in the art.

In some embodiments, the extracellular vesicle comprises an immunomodulating component that is chemically conjugated. Chemical conjugation can be accomplished by covalent bonding of the immunomodulating component to another molecule, with or without use of a linker. The formation of such conjugates is within the skill of artisans and various techniques are known for accomplishing the conjugation, with the choice of the particular technique being guided by the materials to be conjugated. In certain embodiments, polypeptides are conjugated to the extracellular vesicle. In certain other embodiments, non-polypeptides, such as lipids, carbohydrates, nucleic acids, and small molecules, are conjugated to the extracellular vesicle.

In some embodiments, the immunomodulating component is introduced to the extracellular vesicle by hypotonic lysis. In some of these embodiments, the extracellular vesicles are exposed to low ionic strength buffer causing them to burst allowing loading of an immunomodulating component. In some alternative embodiments, controlled dialysis against a hypotonic solution is used to swell the extracellular vesicle and to create pores in the extracellular vesicle membrane. The extracellular vesicle is subsequently exposed to conditions that allow resealing of the membrane.

In some embodiments, the immunomodulating component is introduced to the extracellular vesicle by detergent treatment. In certain embodiments, extracellular vesicles are treated with a mild detergent which transiently compromises the extracellular vesicle membrane by creating pores allowing loading of an immunomodulating component. After extracellular vesicles are loaded, the detergent is washed away thereby resealing the membrane.

In some embodiments, the immunomodulating component is introduced to the extracellular vesicle by receptor mediated endocytosis. In certain embodiments, extracellular vesicles have a surface receptor which upon binding of the immunomodulating component induces internalization of the receptor and the associated immunomodulating component.

In some embodiments, the immunomodulating component is introduced to the extracellular vesicle by mechanical firing. In certain embodiments, extracellular vesicles can be bombarded with an immunomodulating component attached to a heavy or charged particle such as gold microcarriers. In some of these embodiments, the particle can be mechanically or electrically accelerated such that it traverses the extracellular vesicle membrane.

In some embodiments, the immunomodulating component is introduced to the extracellular vesicle by filtration. In certain embodiments, the extracellular vesicles and the immunomodulating component can be forced through a filter of pore size smaller than the extracellular vesicle causing transient disruption of the extracellular vesicle membrane and allowing the immunomodulating component to enter the extracellular vesicle.

In some embodiments, extracellular vesicles are subjected to several freeze thaw cycles, resulting in extracellular vesicle membrane disruption allowing loading of an immunomodulating component.

Methods of Isolating the Extracellular Vesicles

The extracellular vesicles can be isolated from the producer cells. In certain embodiments, the extracellular vesicle is released by the producer cell into the cell culture medium. It is contemplated that all known manners of isolation of extracellular vesicles are deemed suitable for use herein. For example, physical properties of extracellular vesicles can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using extracellular vesicle or producer cell-specific surface markers. For example, specific surface markers can be used in immunoprecipitation, FACS sorting, affinity purification, and magnetic separation with bead-bound ligands.

In some embodiments, size exclusion chromatography can be utilized to isolate the extracellular vesicles. Size exclusion chromatography techniques are known in the art. Exemplary, non-limiting techniques are provided herein. In some embodiments, a void volume fraction is isolated and comprises the extracellular vesicles of interest. Further, in some embodiments, the extracellular vesicles can be further isolated after chromatographic separation by centrifugation techniques (of one or more chromatography fractions), as is generally known in the art. In some embodiments, for example, density gradient centrifugation can be utilized to further isolate the extracellular vesicles. In certain embodiments, it can be desirable to further separate the producer cell-derived extracellular vesicles from extracellular vesicles of other origin. For example, the producer cell-derived extracellular vesicles can be separated from non-producer cell-derived extracellular vesicles by immunosorbent capture using an antigen antibody specific for the producer cell.

In some embodiments, the isolation of extracellular vesicles can involve combinations of methods that include, but are not limited to, differential centrifugation, size-based membrane filtration, immunoprecipitation, FACS sorting, and magnetic separation.

Methods of Measuring the Size of Extracellular Vesicles

In some embodiments, the methods described herein comprise measuring the size of extracellular vesicles and/or populations of extracellular vesicles. Generally, extracellular vesicle size is measured as the longest measurable dimension. Generally, the longest measurable dimension of an extracellular vesicle is also referred to as its diameter.

Extracellular vesicle size can be measured using dynamic light scattering (DLS) and/or multiangle light scattering (MALS). Methods of using DLS and/or MALS to measure the size of extracellular vesicles are known to those of skill in the art, and include the nanoparticle tracking assay (NTA, e.g., using a Malvern NanoSight NS300 nanoparticle tracking device). In a specific embodiment, the extracellular vesicle size is determined using a Malvern NanoSight NS300. In some embodiments, the extracellular vesicles described herein have a longest dimension of about 20-300 nm as measured by NTA (e.g., using a Malvern NanoSight NS300). In other embodiments, the extracellular vesicles described herein have a longest dimension of about 40-200 nm as measured by NTA (e.g., using a Malvern NanoSight NS300). In other embodiments, the extracellular vesicle populations described herein comprise a population, wherein 90% of the extracellular vesicles have a longest dimension of about 20-300 nm as measured by NTA (e.g., using a Malvern NanoSight NS300). In other embodiments, the extracellular vesicle populations described herein comprise a population, wherein 95% of the extracellular vesicles have a longest dimension of about 20-300 nm as measured by NTA (e.g., using a Malvern NanoSight NS300). In other embodiments, the extracellular vesicle populations described herein comprise a population, wherein 99% of the extracellular vesicles have a longest dimension of about 20-300 nm as measured by NTA (e.g., using a Malvern NanoSight NS300). In other embodiments, the extracellular vesicle populations described herein comprise a population, wherein 90% of the extracellular vesicles have a longest dimension of about 40-200 nm as measured by NTA (e.g., using a Malvern NanoSight NS300). In other embodiments, the extracellular vesicle populations described herein comprise a population, wherein 95% of the extracellular vesicles have a longest dimension of about 40-200 nm as measured by NTA (e.g., using a Malvern NanoSight NS300). In other embodiments, the extracellular vesicle populations described herein comprise a population, wherein 99% of the extracellular vesicles have a longest dimension of about 40-200 nm as measured by NTA (e.g., using a Malvern NanoSight NS300).

Extracellular vesicle size can be measured using tunable resistive pulse sensing (TRPS). In a specific embodiment, extracellular vesicle size as measured by TRPS is determined using an iZON qNANO Gold. In some embodiments, the extracellular vesicles described herein have a longest dimension of about 20-300 nm as measured by TRPS (e.g., using an iZON qNano Gold). In other embodiments, the extracellular vesicles described herein have a longest dimension of about 40-200 nm as measured by TRPS (e.g., an iZON qNano Gold). In other embodiments, the extracellular vesicle populations described herein comprise a population, wherein 90% of the extracellular vesicles have a longest dimension of about 20-300 nm as measured by TRPS (e.g., using an iZON qNano Gold). In other embodiments, the extracellular vesicle populations described herein comprise a population, wherein 95% of the extracellular vesicles have a longest dimension of about 20-300 nm as measured by TRPS (e.g., using an iZON qNano Gold). In other embodiments, the extracellular vesicle populations described herein comprise a population, wherein 99% of the extracellular vesicles have a longest dimension of about 20-300 nm as measured by TRPS (e.g., using an iZON qNano Gold). In other embodiments, the extracellular vesicle populations described herein comprise a population, wherein 90% of the extracellular vesicles have a longest dimension of about 40-200 nm as measured by TRPS (e.g., using an iZON qNano Gold). In other embodiments, the extracellular vesicle populations described herein comprise a population, wherein 95% of the extracellular vesicles have a longest dimension of about 40-200 nm as measured by TRPS (e.g., using an iZON qNano Gold). In other embodiments, the extracellular vesicle populations described herein comprise a population, wherein 99% of the extracellular vesicles have a longest dimension of about 40-200 nm as measured by TRPS (e.g., using an iZON qNano Gold).

Extracellular vesicles size can be measured using electron microscopy. In some embodiments, the method of electron microscopy used to measure extracellular vesicle size is transmission electron microscopy. In a specific embodiment, the transmission electron microscope used to measure extracellular vesicle size is a Tecnai™ $G^2$ Spirit BioTWIN. Methods of measuring extracellular vesicle size using an electron microscope are well-known to those of skill in the art, and any such method can be appropriate for measuring extracellular vesicle size. In some embodiments, the extracellular vesicles described herein have a longest dimension of about 20-300 nm as measured by a scanning electron microscope (e.g., a Tecnai™ $G^2$ Spirit BioTWIN scanning electron microscope). In other embodiments, the extracellular vesicles described herein have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population, wherein 90% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population, wherein 95% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population, wherein 99% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population wherein 90% of the extracellular vesicles have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population wherein 95% of the extracellular vesicles have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population wherein 99% of the extracellular vesicles have a longest dimension of about 40-200 nm as measured by a scanning electron microscope (e.g., a Tecnai™ $G^2$ Spirit BioTWIN scanning electron microscope).

Methods for Determining Macrophage Polarization

Disclosed herein are methods and compositions for increasing macrophage polarization from an M2 to an M1 phenotype using an extracellular vesicle comprising one or more immunomodulating component(s) that inhibit expression of a macrophage target gene. The compositions are preferentially taken up by macrophages (as compared to other cell types such as T-cells, B-cells, macrophages, or dendritic cells), and are as or more effective in increasing macrophage polarization than an equimolar amount of the immunomodulating component alone. Methods for determining macrophage polarization, including detection of M2 and M1 phenotypes of macrophages, can be performed by any method known in the art for the determination of M2 and M1 phenotypes. Tissue sections (e.g., from tumor biopsies), blood samples, etc. can be assayed (e.g., stained) for markers of pan-macrophages as well as M2 and M1 macrophages including, but not limited to, M2 cell surface markers (e.g., YM1, FIZZ1, Dectin-1, MGL), M2 associated cytokines (e.g., IL-10, TGFβ, PGE2, CCL2, CCL17, CCL18, CCL22 and CCL24), M1 associated cytokines (e.g., INFγ, IL-12, IL-23, TNFα, IL-6, IL-1, CCLS, CSCL9, CXCL10 and CXCL11), growth factors (e.g., VEGF-A, VEGF-C, EGF, and TGF-β), enzymes (e.g., matrix metalloproteinases MMP2, MMP9, cysteine cathepsin proteases); M2 associated miRNAs (e.g., miRNA146a, miRNA let 7b, and miR-223) and/or M1 associated miRNAs (e.g., miRNA155, miR-33). See, e.g., Mosser, D. M., & Edwards, J. P. (2008). Exploring the full spectrum of macrophage activation. *Nature Reviews Immunology*, 8(12), 958-969; Murray, P. J., Allen, J. E., Biswas, S. K., Fisher, E. A., Gilroy, D. W., Goerdt, S., Wynn, T. A. (2014). Macrophage activation and polarization: nomenclature and experimental guidelines. *Immunity*, 41(1), 14-20. Macrophages and/or macrophage components, secretions or macrophage activity within samples (see, e.g., Gautier, E. L., Shay, T., Miller, J., Greter, M., Jakubzick, C., Ivanov, S., Randolph, G. J. (2007). Gene expression profiles and transcriptional regulatory pathways underlying mouse tissue macrophage identity and diversity, *Nature Immunology* 13(11), 1118-1128) can be detected by flow cytometry, immunohisto-chemistry, immunoblotting, quantitative PCR, or any other method known in the art to detect cells, or cellular products in biological samples.

Methods of Treating Cancer

Also, provided herein are methods of treating cancer in a subject.

In various embodiments, the composition of extracellular vesicles, e.g., exosomes, comprising one or more immunomodulating components that inhibit at least one gene and thereby increase macrophage polarization from the M2 to M1 phenotype is administered to a subject with cancer. In some of these embodiments, the composition can up-regulate an immune response and enhance the tumor targeting of the subject's immune system. In some aspects, the increased macrophage polarization from the M2 to M1 phenotype per se up-regulates the subject's immune response and enhances the tumor targeting of the subject's immune system. Some authors mention the M2d subtype activation as a response to IL-6 and adenosines, and these macrophages are also referred as tumor-associated macrophages (TAM). See, e.g., Rőszer, T. (2015). Understanding the Mysterious M2 Macrophage through Activation Markers and Effector Mechanisms. Mediators of Inflammation, 2015, 1-16; Funes, S. C., Rios, M., Escobar-Vera, J., & Kalergis, A. M. (2018). Implications of macrophage polarization in autoimmunity. Immunology, 154(2), 186-195; and Q. Wang, H. Ni, L. Lan, X. Wei, R. Xiang, and Y. Wang, "Fra-1 protooncogene regulates IL6 expression in macrophages and promotes the generation of M2d macrophages," Cell Research, vol. 20, no. 6, pp. 701-712, 2010. Tumor-associated macrophages (TAM) are typical for their protumoral functions like promotion of cancer cell motility, metastasis formation and angiogenesis and their formation is dependent on microenvironmental factors which are present in developing tumor. TAMs produce immunosuppressive cytokines like IL-10, TGFβ, PGE2 and a very small amount of NO or ROI and low levels of inflammatory cytokines (IL-12, IL-1β, TNFα, IL-6). Ability of TAMs to present tumor-associated antigens is decreased as well as stimulation of the anti-tumor functions of T and NK cells. Also TAMs are not able to lyse tumor cells. https://en.wikipedia.org/wiki/Macrophagepolarization-cite_note-Sica2008-31 Targeting of TAM may be a novel therapeutic strategy against cancer, as has been demonstrated through the delivery of agents to either alter the recruitment and distribution of TAMs, deplete existing TAMs, or induce the re-education of TAMs from an M2 to an M1 phenotype. See, e.g., Lewis, Claire E., and Jeffrey W. Pollard. "Distinct role of macrophages in different tumor microenvironments." Cancer research 66.2 (2006): 605-612; Sica, Antonio, et al. "Macrophage polarization in tumour progression." Seminars in Cancer Biology. Vol. 18. No. 5. Academic Press, 2008; Sica, Antonio, et al. Autocrine production of IL-10 mediates defective IL-12 production and NF-kappa B activation in tumor-associated macrophages. J Immunol. 2000 Jan. 15; 164(2):762-7; Cuccarese, Michael F.; Dubach, J. Matthew; Pfirschke, Christina; Engblom, Camilla; Garris, Christopher; Miller, Miles A.; Pittet, Mikael J.; Weissleder, Ralph (2017 Feb. 8). "Heterogeneity of macrophage infiltration and therapeutic response in lung carcinoma revealed by 3D organ imaging". Nature Communications. 8: 14293; Zeisberger, S M; Odermatt, B; Marty, C; Zehnder-Fjallman, A H M; Ballmer-Hofer, K; Schwendener, R A (2006 Jul. 11). "Clodronate-liposome-mediated depletion of tumour-associated macrophages: a new and highly effective antiangiogenic therapy approach". British Journal of Cancer. 95 (3): 272-281; Rodell, Christopher B.; Arlauckas, Sean P.; Cuccarese, Michael F.; Garris, Christopher S.; Li, Ran; Ahmed, Maaz S.; Kohler, Rainer H.; Pittet, Mikael J.; Weissleder, Ralph (2018 May 21). "TLR7/8-agonist-loaded nanoparticles promote the polarization of tumour-associated macrophages to enhance cancer immunotherapy". Nature Biomedical Engineering; Guerriero, Jennifer L.; Sotayo, Alaba; Ponichtera, Holly E.; Castrillon, Jessica A.; Pourzia, Alexandra L.; Schad, Sara; Johnson, Shawn F.; Carrasco, Ruben D.; Lazo, Suzan (March 2017). "Class IIa HDAC inhibition reduces breast tumours and metastases through anti-tumour macrophages". Nature. 543 (7645): 428-432.

In some embodiments, the cancer being treated is characterized by infiltration of leukocytes (T-cells, B-cells, macrophages, dendritic cells, monocytes) into the tumor microenvironment, or so-called "hot tumors" or "inflammatory tumors.". In some embodiments, the cancer being treated is characterized by low levels or undetectable levels of leukocyte infiltration into the tumor microenvironment, or so-called "cold tumors" or "non-inflammatory tumors". In some embodiments, the composition is administered in an amount and for a time sufficient to convert a "cold tumor" into a "hot tumor", i.e., said administering results in the infiltration of leukocytes (such as T-cells) into the tumor microenvironment.

In some embodiments, the compositions comprise an extracellular vesicle and a combination of more than one immunomodulating component, including a component that promotes macrophage polarization from an M2 to an M1 phenotype, and a component that additionally enhances an immune response, such as a checkpoint blockade inhibitor, e.g., Ipilimumab, targeting CTLA-4, Nivolumab Cemiplimab and Pembrolizumab targeting PD-1, and Atezolizumab, Avelumab, Durvalumab, each targeting PD-L1, and inhibitors of CSFR-1, such as Pexidartinib, PLX7486, ARRY-382, JNJ-40346527, BLZ945, Emactuzumab, AMG820, IMC-CS4 and Cabiralizumab. Administration of these compositions as treatments for subjects with cancer can further up-regulate an immune response and enhance the tumor targeting of the subject's immune system through the combined actions of the immunomodulating components.

In some embodiments, the additional immunomodulating component is an antibody or active fragment that targets CTLA-4, PD-1, PD-L1, or CSF1-R. In embodiments, the antibody or active fragment thereof comprises CDRs that are at least 90%, 91%, 92%, 93%, 94%, 95%, 96%, 97%, 98%, 99%, or 100% identical to the CDRs of Ipilimumab. In embodiments, the antibody or active fragment thereof comprises CDRs that are at least 90%, 91%, 92%, 93%, 94%, 95%, 96%, 97%, 98%, 99%, or 100% identical to the CDRs of Nivolumab. In embodiments, the antibody or active fragment thereof comprises CDRs that are at least 90%, 91%, 92%, 93%, 94%, 95%, 96%, 97%, 98%, 99%, or 100% identical to the CDRs of Cemiplimab. In embodiments, the antibody or active fragment thereof comprises CDRs that are at least 90%, 91%, 92%, 93%, 94%, 95%, 96%, 97%, 98%, 99%, or 100% identical to the CDRs of Pembrolizumab. In embodiments, the antibody or active fragment thereof comprises CDRs that are at least 90%, 91%, 92%, 93%, 94%, 95%, 96%, 97%, 98%, 99%, or 100% identical to the CDRs of Atezolizumab. In embodiments, the antibody or active fragment thereof comprises CDRs that are at least 90%, 91%, 92%, 93%, 94%, 95%, 96%, 97%, 98%, 99%, or 100% identical to the CDRs of Avelumab. In embodiments, the antibody or active fragment thereof comprises CDRs that are at least 90%, 91%, 92%, 93%, 94%, 95%, 96%, 97%, 98%, 99%, or 100% identical to the CDRs of Durvalumab. In embodiments, the antibody or active fragment thereof comprises CDRs that are at least 90%, 91%, 92%, 93%, 94%, 95%, 96%, 97%, 98%, 99%, or 100% identical to the CDRs of Pexidartinib. In embodiments, the antibody or active fragment thereof comprises CDRs that are at least 90%, 91%, 92%, 93%, 94%, 95%, 96%, 97%, 98%, 99%, or 100% identical to the CDRs of PLX7486. In embodiments, the antibody or active fragment thereof comprises CDRs that are at least 90%, 91%, 92%, 93%, 94%, 95%, 96%, 97%, 98%, 99%, or 100% identical to the CDRs of ARRY-382. In embodiments, the antibody or active fragment thereof comprises CDRs that are at least 90%, 91%, 92%, 93%, 94%, 95%, 96%, 97%, 98%, 99%, or 100% identical to the CDRs of JNJ-40346527. In embodiments, the antibody or active fragment thereof comprises CDRs that are at least 90%, 91%, 92%, 93%, 94%, 95%, 96%, 97%, 98%, 99%, or 100% identical to the CDRs of BLZ945. In embodiments, the antibody or active fragment thereof comprises CDRs that are at least 90%, 91%, 92%, 93%, 94%, 95%, 96%, 97%, 98%, 99%, or 100% identical to the CDRs of Emactuzumab. In embodiments, the antibody or active fragment thereof comprises CDRs that are at least 90%, 91%, 92%, 93%, 94%, 95%, 96%, 97%, 98%, 99%, or 100% identical to the CDRs of AMG820. In embodiments, the antibody or active fragment thereof comprises CDRs that are at least 90%, 91%, 92%, 93%, 94%, 95%, 96%, 97%, 98%, 99%, or 100% identical to the CDRs of IMC-CS4. In embodiments, the antibody or active fragment thereof comprises CDRs that are at least 90%, 91%, 92%, 93%, 94%, 95%, 96%, 97%, 98%, 99%, or 100% identical to the CDRs of Cabiralizumab.

In some embodiments, the composition comprising an extracellular vesicle and an immunomodulating component is administered to a subject as a cancer vaccine. In some of these embodiments, the composition is administered to a subject as a personalized cancer vaccine. In some embodiments, the immunomodulating component is a tumor antigen or a peptide derived from a tumor antigen. Examples of suitable tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived a genome sequence of the subject receiving the composition.

The cancers that can be treated with the composition include but are not limited to the cancers listed in Table 5.

Methods of Modulating Gene Expression, Transcriptional Networks and Polarization in Macrophages Some embodiments provide methods of modulating gene expression in a macrophage, comprising administering to a subject an extracellular vesicle comprising one or more immunomodulating component(s), wherein the immunomodulating component is targeted to the gene, and wherein the modulation is equal to or greater than modulation produced by administration of an equimolar amount of free immunomodulating component targeted to the gene. Also provided are methods of inhibiting gene expression in a macrophage, comprising administering to a subject an extracellular vesicle comprising one or more immunomodulating component(s), wherein the immunomodulating component is targeted to the gene, and wherein the inhibition is equal to or greater than inhibition produced by administration of an equimolar amount of free immunomodulating component targeted to the gene. Some embodiments provide methods of repressing a downstream target of a gene in a macrophage, comprising administering to a subject an extracellular vesicle comprising one or more immunomodulating component(s), wherein the immunomodulating component is targeted to the gene, and wherein the repression is equal to or greater than repression produced by administration of an equimolar amount of free immunomodulating component targeted to the gene. Some embodiments provide methods of altering polarization of a population of macrophages, comprising administering to a subject an extracellular vesicle comprising one or more immunomodulating component(s), wherein the immunomodulating component is targeted to the gene, and wherein the alteration of polarization is equal to or greater than alteration of polarization produced by administration of an equimolar amount of free immunomodulating component targeted to the gene. In some embodiments the extracellular vesicle is an exosome. In some embodiments, the immunomodulating component is an ASO. In some embodiments the alteration in polarization is a change from an M2 to an M1 phenotype Methods of Treating Fibrotic Conditions Also, provided herein are methods of treating a fibrotic condition in a subject comprising administering to the subject in need thereof an effective amount of a composition comprising exosomes comprising an immunomodulating component that repolarizes macrophages from the M2 to M1 phenotype. In some embodiments, the fibrotic condition is lung fibrosis, liver fibrosis, or pancreatic fibrosis. In certain embodiments, the liver fibrosis is non-alcoholic steatohepatitis, or NASH. See, e.g., See Mayo Clinic Staff. "Definition [of pulmonary fibrosis]". Mayo Foundation for Medical Education and Research. Archived from the original on 15 Jul. 2014. Retrieved 26 Jul. 2014, available from the world wide at webmayoclinic.org/diseases-conditions/pulmonary-fibrosis/symptoms-causes/syc-20353690; Ferri F F. Idiopathic pulmonary fibrosis. In: Ferri's *Clinical Advisor* 2016. Philadelphia, Pa.: Mosby Elsevier; 2016; Gross T J, Hunninghake G W (2001). "Idiopathic pulmonary fibrosis". *N Engl J Med.* 345 (7): 517-525; Friedman L S (2014). *Current medical diagnosis and treatment* 2014. [S.1.]: Mcgraw-Hill. pp. Chapter 16. Liver, Biliary Tract, & Pancreas Disorders; Chalasani N, Younossi Z, Lavine J E, Charlton M, Cusi K, Rinella M, Harrison S A, Brunt E M, Sanyal A J (January 2018). "The diagnosis and management of nonalcoholic fatty liver disease: Practice guidance from the American Association for the Study of Liver Diseases". *Hepatology.* 67 (1): 328-357; Xue J, Sharma V, Hsieh M H, Chawla A, Murali R, Pandol S J, Habtezion A. *Nat Commun.* 2015 May 18; 6:7158.

Modes of Administration

In some embodiments, the composition is administered intravenously to the circulatory system of the subject. In some embodiments, the composition is infused in suitable liquid and administered into a vein of the subject.

In some embodiments, the composition is administered intra-arterialy to the circulatory system of the subject. In some embodiments, the composition is infused in suitable liquid and administered into an artery of the subject.

In some embodiments, the composition is administered to the subject by intrathecal administration. In some embodiments, the composition is administered via an injection into the spinal canal, or into the subarachnoid space so that it reaches the cerebrospinal fluid (CSF).

In some embodiments, the composition is administered to the subject by intranasal administration. In some embodiments, the composition can be insufflated through the nose in a form of either topical administration or systemic administration. In certain embodiments, the composition is administered as nasal spray.

In some embodiments, the composition is administered to the subject by intraperitoneal administration. In some embodiments, the composition is infused in suitable liquid and injected into the peritoneum of the subject. In some embodiments, said intraperitoneal administration results in distribution of the composition (e.g., the extracellular vesicles in the composition) to the lymphatics. In some embodiments, said intraperitoneal administration results in distribution of the composition (e.g., the extracellular vesicles in the composition) to the thymus, spleen, and/or bone marrow. In some embodiments, said intraperitoneal administration results in distribution of the composition (e.g., the extracellular vesicles in the composition) to one or more lymph nodes. In some embodiments, said intraperitoneal administration results in distribution of the composition (e.g., the extracellular vesicles in the composition) to one or more of the cervical lymph node, the inguinal lymph node, the mediastinal lymph node, or the sternal lymph node. In some embodiments, said intraperitoneal administration results in distribution of the composition (e.g., the extracellular vesicles in the composition) to the pancreas.

In some embodiments, the composition is administered to the subject by periocular administration. In some embodiments, the composition is injected into the periocular tissues. Periocular drug administration includes the routes of subconjunctival, anterior sub-Tenon's, posterior sub-Tenon's, and retrobulbar administration.

In some embodiments, the composition is administered into the same subject by multiple routes of administration. In some embodiments, said multiple routes of administration comprise intravenous administration, intra-arterial administration, intrathecal administration, intranasal administration, intraperitoneal administration, and/or periocular administration. In a preferred embodiment, said multiple routes of administration comprise intravenous administration and intraperitoneal administration.

In certain embodiments, the dosage of the extracellular vesicles is between 1 ng to 10 ng, 10 ng to 100 ng, 100 ng to 1 µg, 1 µg to 5 µg, 5 µg to 10 µg, 10 µg to 50 µg, 50 µg to 75 µg, 75 µg to 100 µg, 100 µg to 150 µg, 150 µg to 200 µg, 200 µg to 300 µg, 300 µg to 500 µg, 500 µg to 1 mg, or 1 mg to 10 mg.

The compositions can be administered once to the subject. Alternatively, multiple administrations can be performed over a period of time. For example, two, three, four, five, or more administrations can be given to the subject. In some embodiments, administrations can be given as needed, e.g., for as long as symptoms associated with the disease, disorder or condition persists. In some embodiments, repeated administrations can be indicated for the remainder of the subject's life. Treatment periods can vary and can be, e.g., no longer than a year, six months, three months, two months, one month, two weeks, one week, three days, two days, or no longer than one day.

In certain embodiments, doses of extracellular vesicles are administered at intervals such as once daily, every other day, once weekly, twice weekly, once monthly or twice monthly.

In some embodiments, the pharmaceutical composition is administered at a frequency sufficient to effectively increase the concentration of the immunomodulating component in the target cell or tissue above a level that is associated with a symptom of the disease, disorder or condition.

In some embodiments, the compositions are administered at least twice over a treatment period such that the disease, disorder or condition is treated, or a symptom thereof is ameliorated. In some embodiments, the compositions are administered at least twice over a treatment period such that the disease, disorder or condition is treated or a symptom thereof is prevented. In some embodiments, the pharmaceutical composition is administered a sufficient number of times over a treatment period such that a sufficient amount of immunomodulating component is delivered to the target cell or tissue during the treatment period. In some embodiments, the pharmaceutical composition is administered a sufficient number of times over a treatment period such that a sufficient amount of immunomodulating component is delivered to the target cell or tissue during the treatment period such that one or more symptoms of the disease, disorder or condition is prevented, decreased, ameliorated or delayed. In some embodiments, increasing the immunomodulating component concentration in the target cell or tissue includes increasing the peak concentration, while in others it includes increasing the average concentration. In some embodiments, a substantial increase during the treatment period can be determined by comparing a pretreatment or post-treatment period in the subject, or by comparing measurements made in a population undergoing treatment with a matched, untreated control population.

In some embodiments, the pharmaceutical composition is administered a sufficient number of times per treatment period such that the concentration of immunomodulating component in the target cell or tissue is increased for at least about one week, two weeks, three weeks, four weeks, one month, two months, three months, four months, five months, six months or greater than six months. In some embodiments, the pharmaceutical composition is administered a sufficient number of times per treatment period such that the concentration of immunomodulating component in the target cell or tissue is increased for a period of time at least as long as the treatment period.

In some embodiments, the time interval between repeated administrations within a treatment period is no longer than the period in which the number of extracellular vesicles in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of extracellular vesicles present in the administered pharmaceutical composition.

In some embodiments, the methods of treatment further comprise one or multiple doses of non-therapeutic extracellular vesicles prior to the injection of a suitable therapeutic dose of extracellular vesicles harboring a therapeutic agent. In certain embodiments, the non-therapeutic extracellular vesicle is administered separately to and at a different dosage than the therapeutic extracellular vesicles. In certain embodiments, the dosage of the non-therapeutic extracellular vesicle is greater than the dosage of the therapeutic extracellular vesicle. In certain other embodiments, the dosage of the non-therapeutic extracellular vesicle is smaller than the dosage of the therapeutic extracellular vesicle. In certain embodiments, the dosage of the non-therapeutic extracellular vesicle is the same as the therapeutic extracellular vesicle. In various embodiments, the methods of non-therapeutic extracellular vesicles prior to injection of a suitable dose of therapeutic extracellular vesicles reduce the update of the therapeutic extracellular vesicles in the liver, lung, and/or spleen. See co-owned PCT application PCT/US2017/047794, incorporated herein by reference for all purposes.

An effective amount of the composition is provided based, at least in part, on the target tissue, target cell type, means of administration, physical characteristics of the extracellular vesicle (e.g., size, and in some cases the extent of molecules to be delivered) and other determinants. In general, an effective amount of the composition provides efficient cellular response of the target cell. Increased efficiency can be demonstrated by increased cell transfection (i.e., the percentage of cells transfected with the extracellular vesicle constituents), increased cellular response or reduced innate immune response of the host subject.

The dosing and frequency of the administration of the extracellular vesicles and pharmaceutical compositions thereof can be determined, e.g., by the attending physician based on various factors such as the severity of disease, the patient's age, sex and diet, the severity of any inflammation, time of administration and other clinical factors. In an example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse effects that can appear.

Additional Embodiments

Other aspects and embodiments are provided in the following numbered items.

1. An extracellular vesicle comprising one or more nucleic acid molecules that inhibits at least one gene and thereby increases macrophage polarization from the M2 to M1 phenotype.
2. The extracellular vesicle of embodiment 1, wherein the extracellular vesicle is an exosome.
3. The extracellular vesicle of embodiment 1 or 2, wherein the nucleic acid is an inhibitory RNA.
4. The extracellular vesicle of any one of embodiments 1-3, wherein the inhibitory RNA is an antisense RNA, siRNA, ShRNA, miRNA, an lncRNA or pre-miRNA.

5. The extracellular vesicle of any one of embodiments 1-4, wherein the at least one gene is selected from the group consisting of:

KRAS, HRAS, NRAS, HIF1-alpha, HIF1-beta, Sp1, P300, LKB1, AMPK, STAT3, STATE, n-MYC, and c-MYC, HCAR1, A2AB, DO, TDO, Arginase, Glutaminase, and PKM2.

6. The extracellular vesicle of embodiment 5, wherein the gene is KRAS.

7. The extracellular vesicle of embodiment 6, wherein the nucleic acid is an inhibitory RNA that targets wild-type human KRAS.

8. The extracellular vesicle of embodiment 7, wherein the inhibitory RNA also targets mouse $Kras^{G12D}$.

9. The extracellular vesicle of any one of embodiments 1-8, wherein the macrophage is a tumor resident macrophage.

10. The extracellular vesicle of embodiment 9, wherein the tumor is a pancreatic tumor.

11. The extracellular vesicle of any one of embodiments 1-10, further comprising an additional immunomodulating component.

12. The extracellular vesicle of embodiment 11, wherein the additional immunomodulating component is a small molecule drug, an antibody or a therapeutic protein.

13. The extracellular vesicle of embodiment 12, wherein the antibody is an immune checkpoint inhibitor.

14. A pharmaceutical composition comprising the extracellular vesicle of any one of embodiments 1-13.

15. A method of treating a disease in a patient in need thereof comprising administering the extracellular vesicle of any one of embodiments 1-13 or the pharmaceutical composition of embodiment 14 to the patient, thereby treating the disease in the patient.

16. The method of embodiment 15, wherein the disease is a cancer.

17. The method of embodiment 15 or 16, wherein the patient is human.

18. The method of any one of embodiments 1-17, wherein the nucleic acid is an inhibitory RNA targeting a proto-oncogene.

19. The method of embodiment 18, wherein the proto-oncogene is human KRAS.

20. The method of embodiment 19, wherein the cancer is pancreatic cancer.

21. The method of any one of embodiments 15-20, further comprising performing at least a second therapy.

22. The method of embodiment 21, wherein the second therapy comprises a surgical therapy, chemotherapy, radiation therapy, cryotherapy, hormonal therapy, or immunotherapy.

23. The extracellular vesicle of any one of the above embodiments wherein the M2 macrophage is a tumor associated macrophage selected from the group consisting of a M2a, M2b, and M2c macrophage.

24. The extracellular vesicle of any one of the above embodiments wherein the M1 macrophage exhibits increased secretion of inflammatory cytokines and chemokines selected from the group consisting of INFγ, IL-12, IL-23, TNFα, IL-6, IL-1, CSCL9, CXCL10 and CXCL11 compared to the M2 macrophage prior to polarization.

25. The extracellular vesicle of any one of the above embodiments wherein the M1 macrophage exhibits decreased secretion of immunosuppressive cytokines and chemokines selected from the group consisting IL-10, TGFβ, $PGE_2$, CCL2, CCL17, CCL18, CCL22 and CCL24 compared to the M2 macrophage prior to polarization.

26. The extracellular vesicle of any one of the above embodiments wherein the M1 macrophage expresses increased tumor associated antigen compared to the M2 macrophage prior to polarization.

27. The extracellular vesicle of any one of the above embodiments wherein the M1 macrophage increases stimulation of $CD8^+$ T-Cells and/or Natural Killer cells compared to the M2 macrophage prior to polarization.

28. A method of treating pancreatic cancer in a subject comprising: administering to the subject an extracellular vesicle comprising an inhibitory RNA targeting human wild-type KRAS; wherein the treatment increases the percentage of polarization of tumor-resident macrophages from the M2 to M1 phenotype to a greater level than that observed in a patient treated with an inhibitory RNA targeting human $KRAS^{G12D}$.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pa.: Mack Publishing Company, 2005); Carey and Sundberg Advanced Organic Chemistry $3^{rd}$ Ed. (Plenum Press) Vols A and B (1992).

Example 1: Knockdown of Transcription Factors in M2 Macrophages

Methods:
Monocyte Isolation from PBMC:
  50 ml of Buffy coat was received
  15 ml of ficol was pipetted into 50 ml STEMCELL SepMate tubes
  Buffy coat was diluted in PBS 2 mM EDTA, such that final volume was ~250 mL
  The diluted buffy coat sample was poured into Sepmate tubes until final volume in the tube was ~45-50 ml
  The tubes were centrifuged at 1000 g for 15 min with brake on 1
  Plasma was aspirated from the spun tubes, and the buffy coat layer was collected with a pipetaid into a 50 ml conical tube. Tubes were filled with PBS/EDTA and centrifuged to pellet the cells at 500 g for 3 min.

If red blood cells were highly present, the cells were resuspended in 10 ml of ACK lysing buffer (ThermoFisher, Catalog no. A1049201) and incubated at room temperature for 3 minutes (manufacturers protocol). The tubes were filled with PBS/EDTA and centrifuge at 500 g for 3 minutes.

Tubes were spun down 5 min at 400×g, and pellet was washed with PBS EDTA once more and re-pelleted The pellet was resuspended in RoboSep buffer (STEM-CELL, catalog no. 20104) and cells were counted using a 1:1 dilution with trypan blue (Thermofisher) (~500 million PBMCs yielded from one buffy coat)

CD14+ monocytes were isolated using EasySep Human Monocyte Enrichment Kit (STEMCELL, Catalog no. 19059RF), according to manufacturer's protocol (~10% of total cells were isolated as monocytes)

5 million monocytes were plated in one plate in RPMI 10% FBS 1% Anti Anti+40 ng/mlM-CSF Macrophage Differentiation and Polarization:
(Adaptedfrom https://www.atsjournals.org/doi/full/10.1165/rcmb.2015-0012OC)

The plated cells were cultured in RPMI-1640 10% FBS 1% Anti Anti 1% PenStrep+40 ng/ml M-CSF (Biolegend) for 5-6 days at 37 C, 5% CO2. 5 ml of the same fresh media was added on Day 1 and 3 post plating. At day 5, polarizing cytokines were added as follows (with 40 ng/ml MSCF; all cytokines added at 20 ng/ml):

M0: no cytokines
M2a: IL-4
M2c: IL-10
M2++: I14, I110, TGFb
M1: IFN-g+LPS (100 ng/ml)
TAM: 75% Panc-1 supernatant
Cells were incubated with cytokines for 24 hours At Day 6, media was aspirated, cells were wash with PBS and then 10 ml of PBS 5 mM EDTA (ice cold) was added per plate, and incubate at 4 C for 30 min Cells were gently scraped off plates, and counted.

50,000 cells per well were then plated in a 96 well plate in in RPMI-1640 10% FBS 1% Anti Anti 1% PenStrep+40 ng/ml M-CSF (Biolegend) with the respective cytokines for different macrophage populations (see above) for 24 hours, after which treatments were initiated.

Exosome Purification:

Exosomes were collected from the supernatant of high density suspension cultures of HEK293 SF cells after 9 days. The supernatant was filtered and fractionated by anion exchange chromatography and eluted in a step gradient of sodium chloride. The peak fraction with the highest protein concentration contained exosomes and contaminating cellular components. The peak fraction was isolated and further fractionated on an Optiprep™ (60% iodixanol w/v) density gradient by ultracentrifugation.

The exosome fraction was concentrated by ultracentrifugation in a 38.5 mL Ultra-Clear (344058) tube for a SW 32 Ti rotor at 133,900×g for 3 hours at 4° C. The pelleted material was resuspended in 1 mL PBS and 3 mL of Optiprep™, bringing the final iodixanol concentration to 45%. For the Optiprep™ gradient, a 4-tier sterile gradient was prepared with 4 mL of 45% iodixanol containing the resuspended material, 3 mL 30% iodixanol, 2 mL 22.5% iodixanol, 2 mL 17.5% iodixanol, and 1 mL PBS in a 12 mL Ultra-Clear (344059) tube for a SW 41 Ti rotor. The Optiprep™ gradient was ultracentrifuged at 150,000×g for 16 hours at 4° C. to separate the exosome fraction. Ultracentrifugation resulted in a Top Fraction known to contain exosomes, a Middle Fraction containing cell debris of moderate density, and a Bottom Fraction containing high density aggregates and cellular debris. The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 µL) and stored at 4° C.

Figure 2:
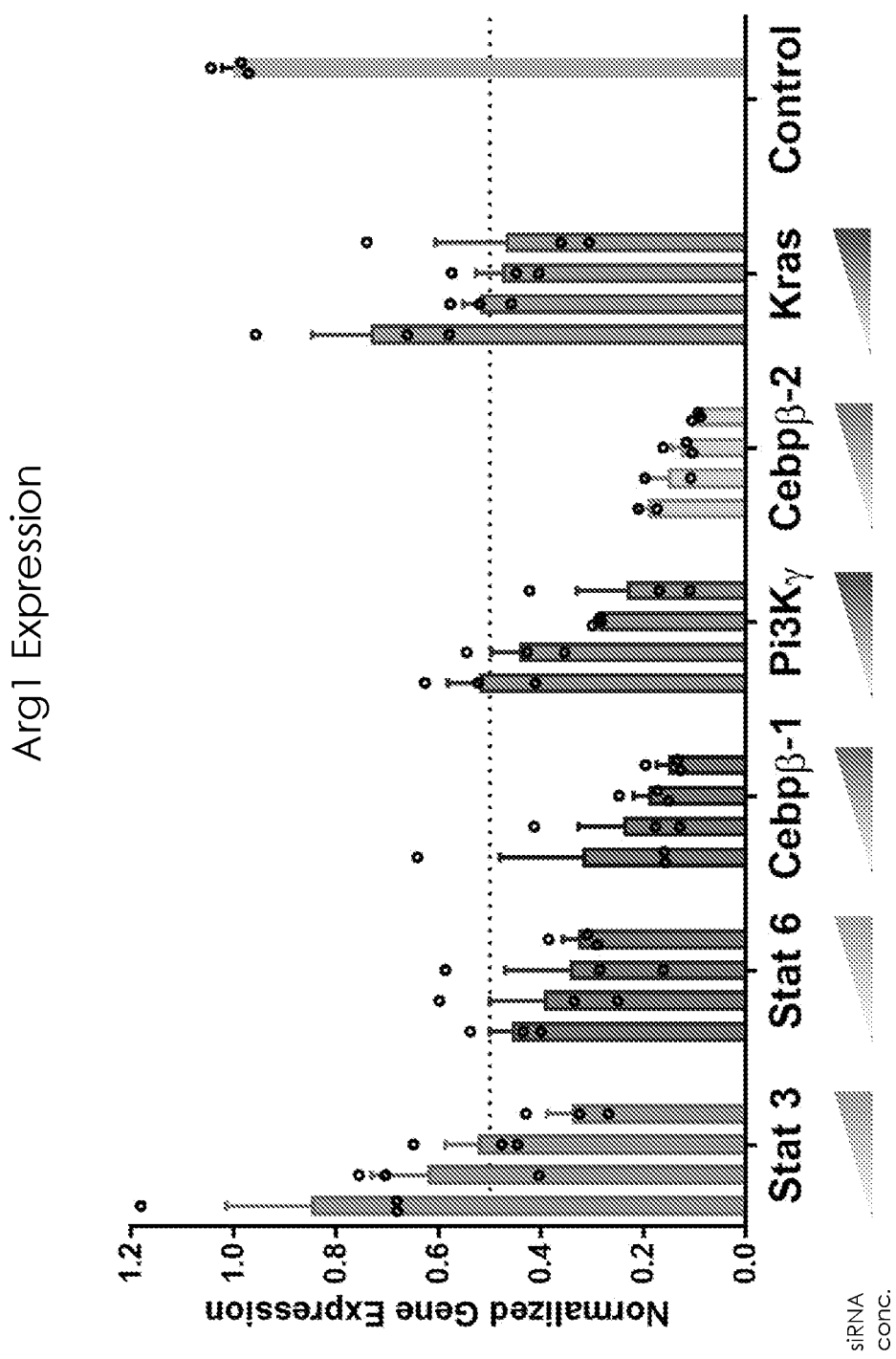
FIG. 2 shows Arg1 expression after transfection of increasing amounts of siRNAs targeting Stat 3, Stat 6, Cebpβ-1, Pi3Kγ, CEBPβ-2, and Kras respectively. Scrambled siRNA transfected macrophages were used as control.

Many solid tumors are characterized by a myeloid-rich cellular infiltrate, often comprising tumor-associated macrophages, characterized as having an alternatively-activated, or M2, phenotype. M2 macrophages express high levels of phosphorylated STAT3 and STAT6, which promote the expression of the metabolic enzyme Arginase (Arg1). To demonstrate that knockdown of critical M2 genes alters the M2 phenotype of in vitro differentiated macrophages, murine RAW264.7 macrophages were polarized to an M2 state as described above. Cultured polarized macrophages were transfected with increasing amounts of siRNA targeting STAT3, STAT6, CEBPβ-1, CEBPβ-2, Pi3Kγ, or KRAS (12.5 nM, 25 nM, 50 nM, and 100 nM). Each of the genes was repressed in a dose-dependent manner (FIG. 1), and the knockdown of each M2 gene led to the concomitant reduction of Arg1 (FIG. 2), demonstrating that the M2 phenotype could be altered by reducing the expression of upstream regulators.

Example 2: Differential Exosome Uptake by Macrophage Subtypes

Figure 3:
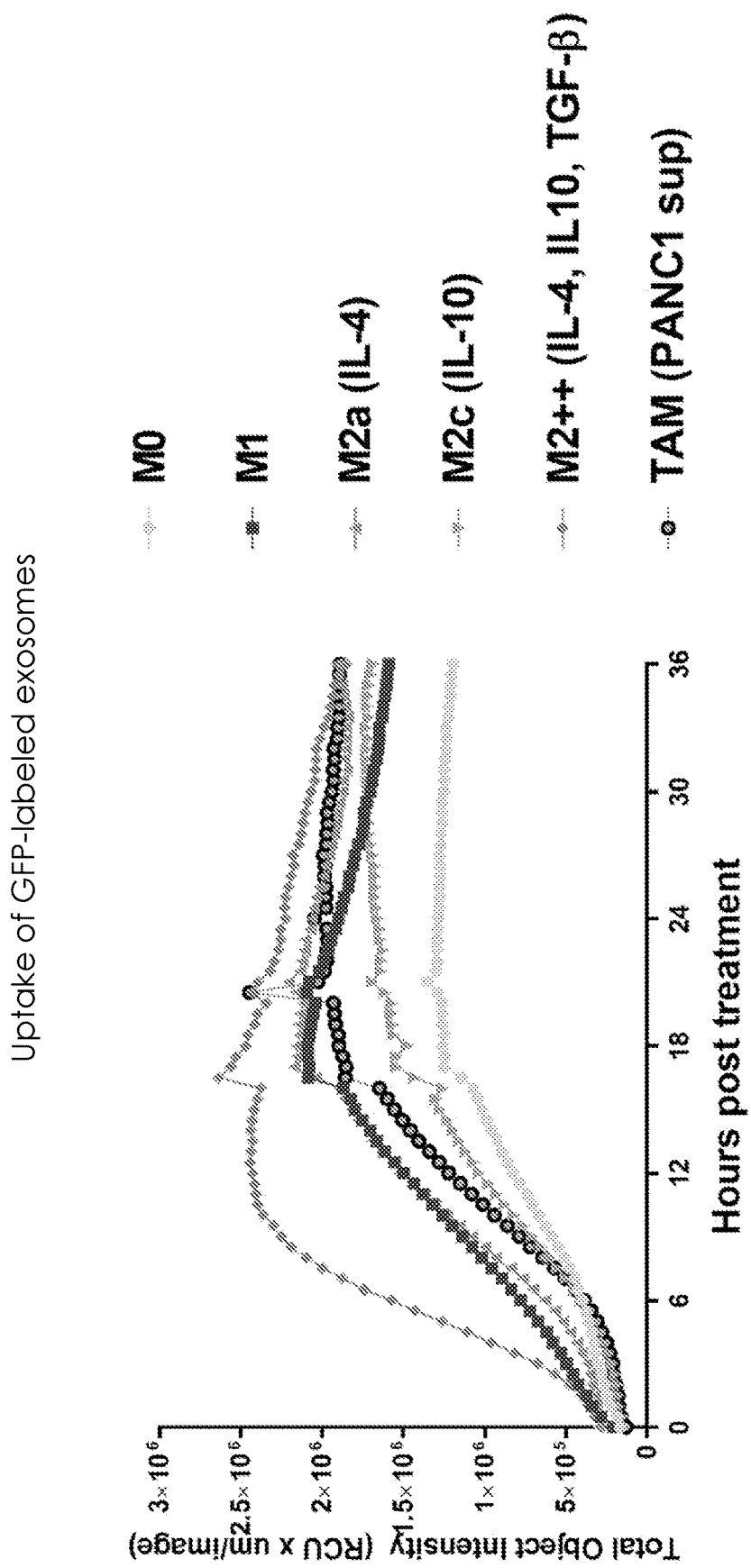
FIG. 3 shows the exosome uptake as determined by total cellular GFP intensity of six macrophage subpopulations (M0, M1, M2a, M2c, M2++, and TAM).

Macrophage subtypes are characterized by alterations in metabolic and other phenotypic activity. To understand whether certain macrophage subtypes preferentially take up exosomes, six macrophage subpopulations (M0, M1, M2a, M2c, M2++, and TAM) were incubated with increasing levels of HEK293 SF-derived exosomes engineered to express lumenal GFP. Exosome uptake was determined by measuring total cellular GFP intensity over 36 hours in an IncuCyte® live cell analysis system (Essen Bioscience). As shown in FIG. 3, while all macrophage subtypes showed uptake of exosomes, M0 macrophages were the least efficient at taking up exosomes, while M2++ macrophages were substantially more efficient at taking up exosomes compared to other macrophage subtypes.

Figure 4:
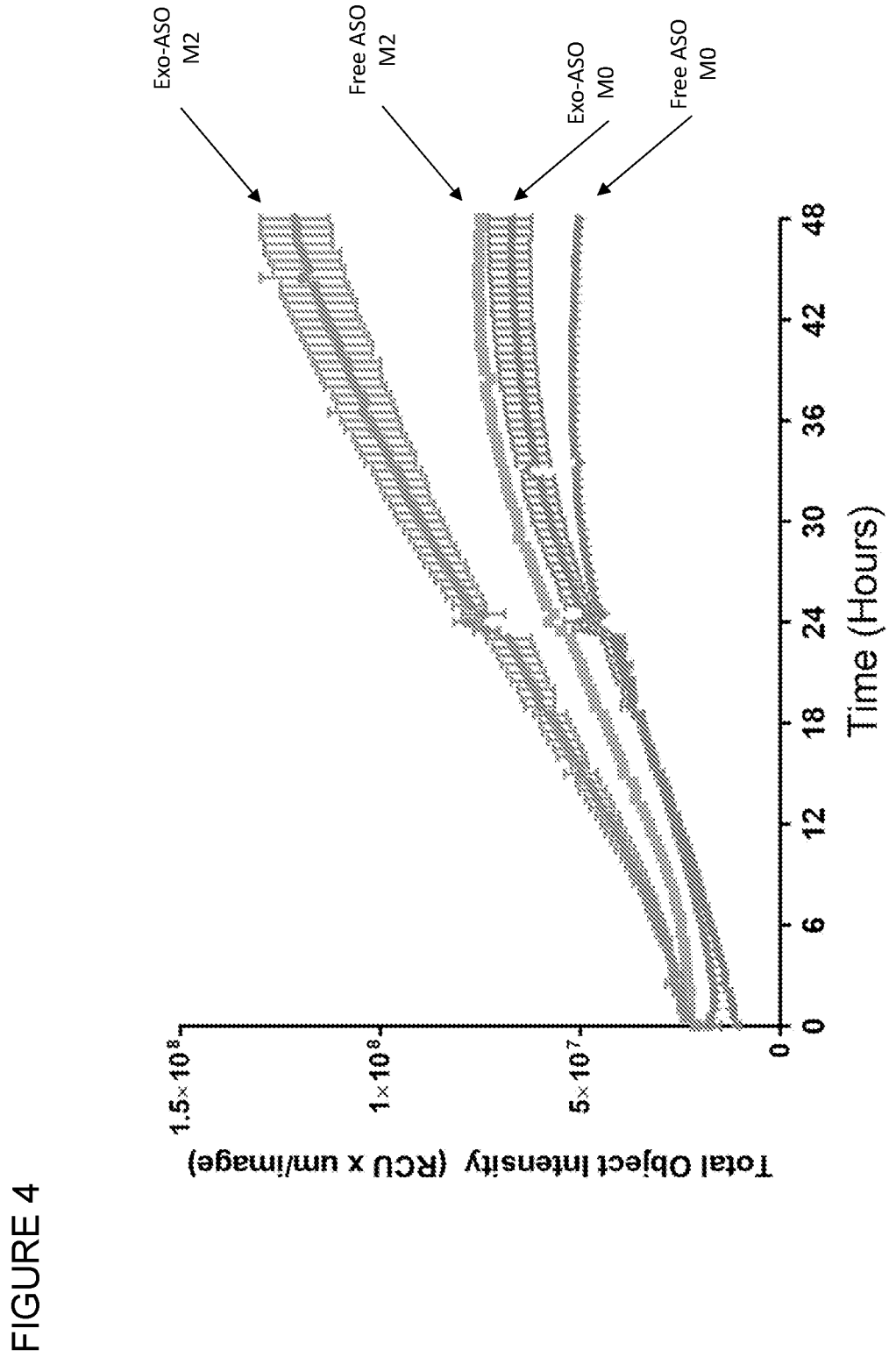
FIG. 4 shows the uptake of free antisense oligos (Free-ASO) and ASO-loaded exosomes (Exo-ASO) by M2 or M0 macrophages as measured by total fluorescence intensity.

Since M2 macrophages are efficient at taking up exosomes, we investigated whether ASO-loaded exosomes would be more efficient at targeting intracellular macrophage targets (e.g., more efficient at knocking down expression of the target gene, and down-stream effector molecules within the gene's signaling pathway) than ASOs alone. 2'-methoxyethyl (MOE) single stranded DNA/RNA ASOs targeting STAT3 and carrying a Cy5 fluorescent tracer and 5' cholesterol linker were generated. HEK293 SF exosomes were mixed with the cholesterol-tagged fluorescent ASOs, and free ASOs were removed by ultracentrifugation and removal of the ASO-containing supernatant. M2 and M0 macrophages were plated at equal density and incubated with matched concentrations of free ASOs or ASO-loaded exosomes (Exo-ASO) as measured by total fluorescence intensity. Total cellular fluorescence was measured over 48 hours and quantified using an IncuCyte® live-cell analysis system. As shown in FIG. 4, M2 macrophages more readily took up both free ASOs and Exo-ASO compared to M0 macrophages. Interestingly, Exo-ASOs were taken up more efficiently by both M0 and M2 macrophages, suggesting that delivery of ASOs to M2 macrophages may be enhanced by loading on exosomes.

Figure 5B:
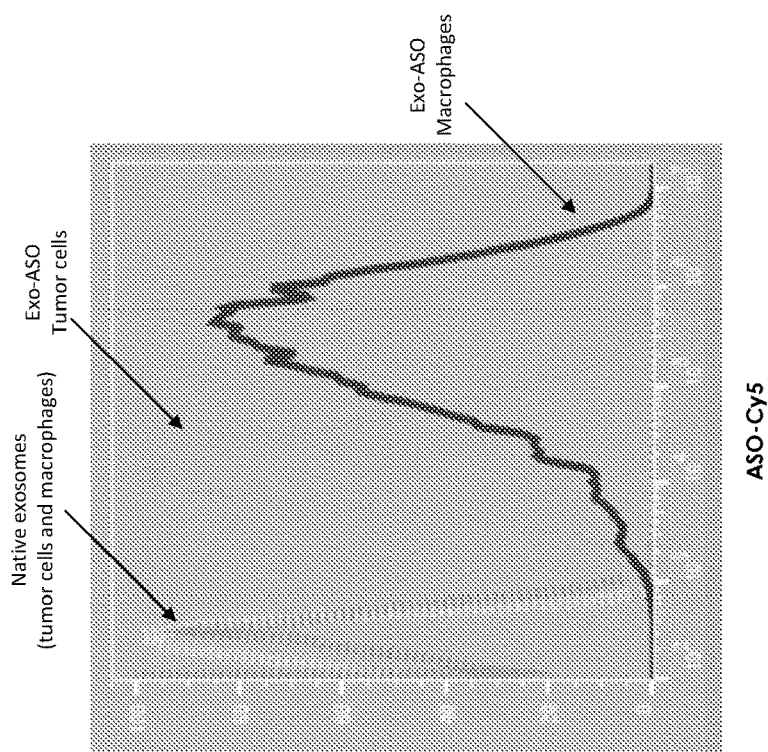
FIG. 5B shows the native exosome and Exo-ASO update by tumor cells and macrophages in vivo after injection of a single dose of native unlabeled exosomes or Cy5-labeled Exo-ASO in B16F10 tumor-bearing mice.
Figure 5A:
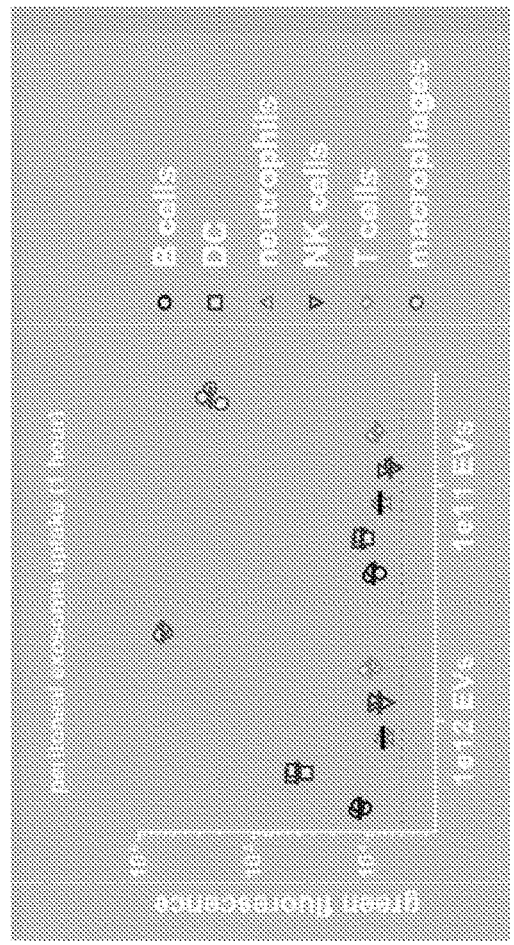
FIG. 5A shows the exosome uptake by macrophages in vivo after intraperitoneal injection of $1\times10^{11}$ or $1\times10^{12}$ GFP-containing exosomes in naïve mice.

To determine whether exosomes or Exo-ASO were differentially taken up by macrophages as compared to other cell types in vivo, naïve mice were dosed intraperitoneally with either $1 \times 10^{11}$ or $1 \times 10^{12}$ GFP-containing exosomes. One hour post-injection, total peritoneal cells were isolated and characterized by flow cytometry for GFP positivity among different immune cell subsets, i.e., B cells, Dendritic cells, neutrophils, Natural Killer (NK) cells, T cells and macrophages. As shown in FIG. 5A, at both doses, macrophages were the predominant cell type to take up fluorescent exosomes. To determine whether this difference occurred in a disease setting, B16F10 tumor-bearing mice were injected with a single dose of Cy5-labeled Exo-ASO or native unlabeled exosomes. The injected tumors were isolated, dissociated, and measured by flow cytometry. As shown in FIG. 5B, macrophages took up Exo-ASO much more readily than tumor cells (~100-fold greater overall Cy5 signal), suggesting that delivery of Exo-ASO can reach macrophage populations in several complex cellular mixtures. Furthermore, the preferential uptake of Exo-ASO by macrophages as compared to the other tested cell types (B cells, Dendritic cells, neutrophils, Natural Killer (NK) cells and T cells) enables methods of ASO delivery targeted to macrophage cells, comprising administering an Exo-ASO composition to a subject, wherein the administered composition is preferentially taken up by macrophages present in the subject (as compared to uptake by other immune cell subsets, e.g., B cells, Dendritic cells, neutrophils, Natural Killer (NK) cells and T cells). This enhanced macrophage specificity of the Exo-ASO composition improves safety of the administered composition by reducing effects in off-target cells.

Figure 6:
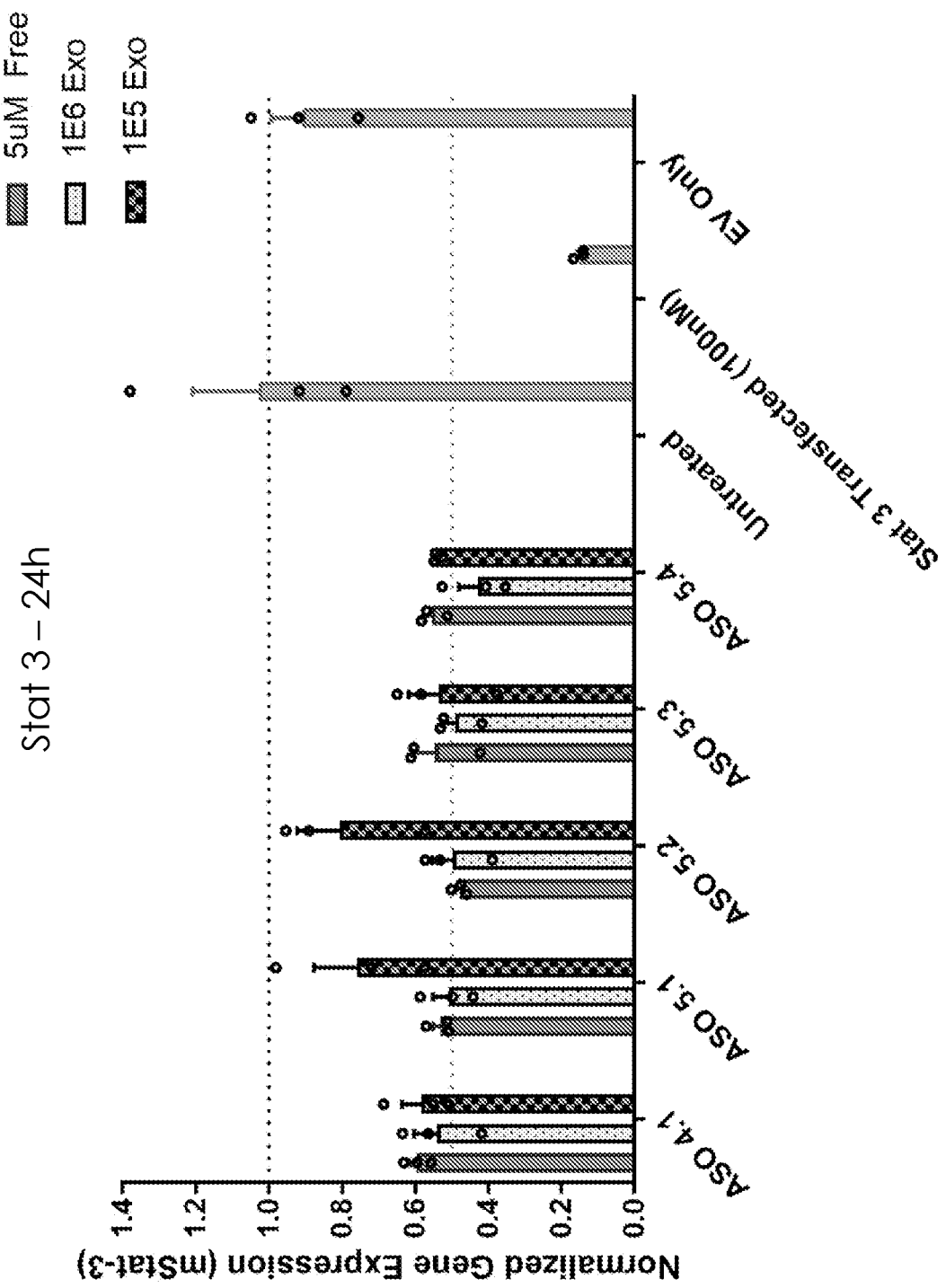
FIG. 6 shows Stat 3 expression in M2 polarized murine RAW264.7 cells after incubation with 5 μM free cholesterol-tagged ASO or either $1\times10^5$ or $1\times10^6$ exosomes loaded with the cholesterol-tagged ASO. Five different cholesterol-tagged ASOs targeting STAT3 were tested: ASO 4.1, double-stranded MOE chemistry; ASO 5.1 and ASO 5.2, single-stranded O-methyl chemistry; ASO 5.3 and ASO 5.4, single-stranded MOE chemistry. Untreated polarized macrophages and polarized macrophages incubated with unmodified exosomes were used as negative control. Stat 3 siRNA transfected macrophages were used as positive control.
Figure 7:
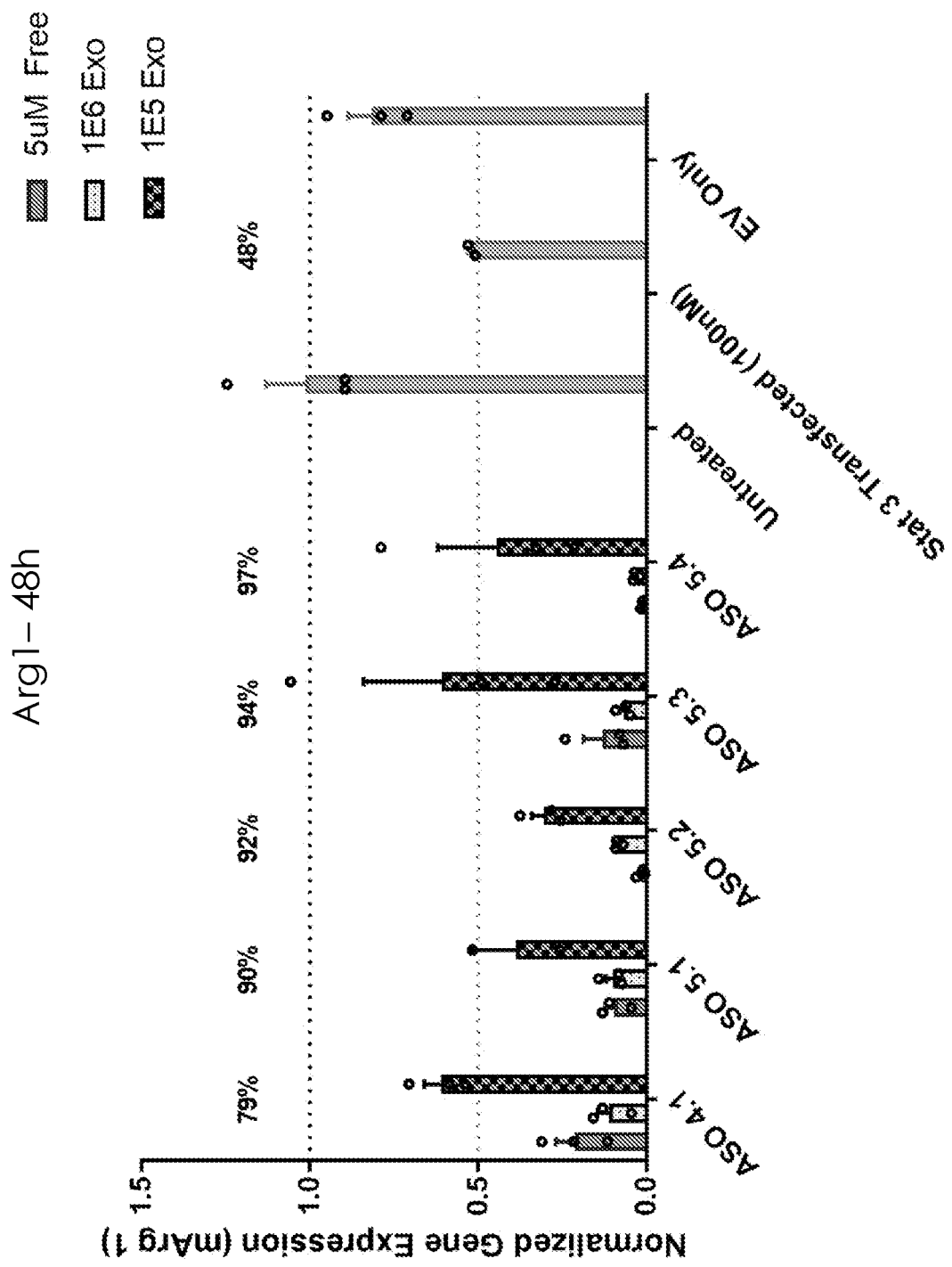
FIG. 7 shows Arg1 transcript level in M2 polarized murine RAW264.7 cells after incubation with 5 μM free cholesterol-tagged ASO or either $1\times10^5$ or $1\times10^6$ exosomes loaded with the cholesterol-tagged ASO. Five different cholesterol-tagged ASOs targeting STAT3 were tested: ASO 4.1, double-stranded MOE chemistry; ASO 5.1 and ASO 5.2, single-stranded O-methyl chemistry; ASO 5.3 and ASO 5.4, single-stranded MOE chemistry. Untreated polarized macrophages and polarized macrophages incubated with unmodified exosomes were used as negative control. Stat 3 siRNA transfected macrophages were used as positive control.
Figure 8A:
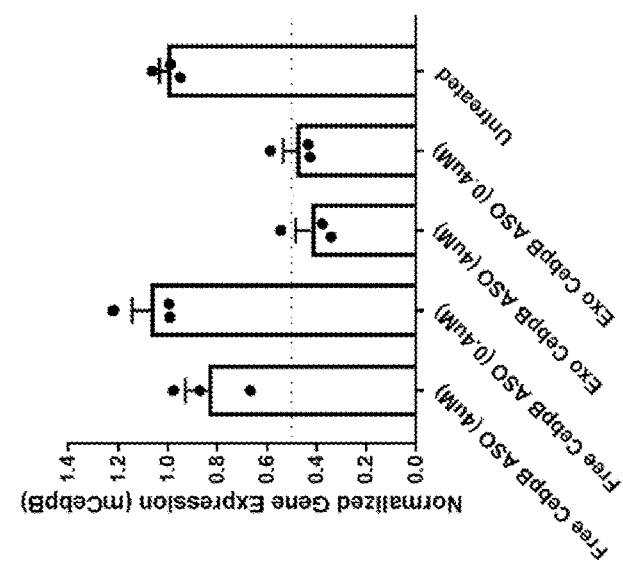
FIG. 8A shows STAT3 expression in M2 polarized murine RAW264.7 cells after incubation with high (4 μM) dose of ASO or high (4 μM) and low (0.4 μM) doses of Exo-ASO for STAT3.
Figure 8B:
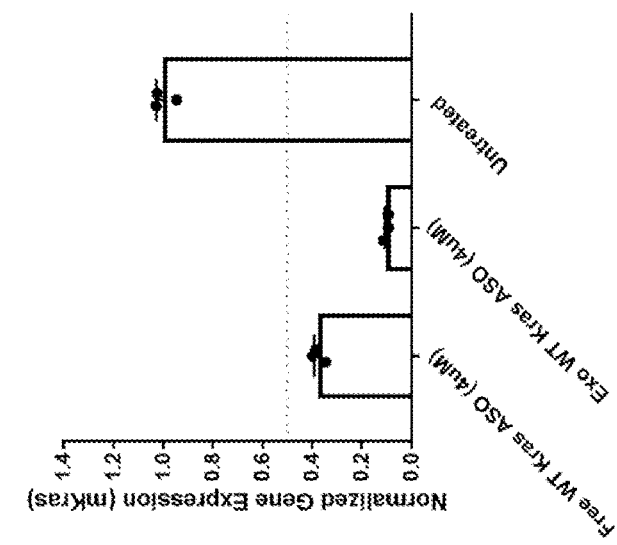
FIG. 8B shows KRAS expression in M2 polarized murine RAW264.7 cells after incubation with high (4 μM) high dose of ASO or Exo-ASO for KRAS.
Figure 8C:
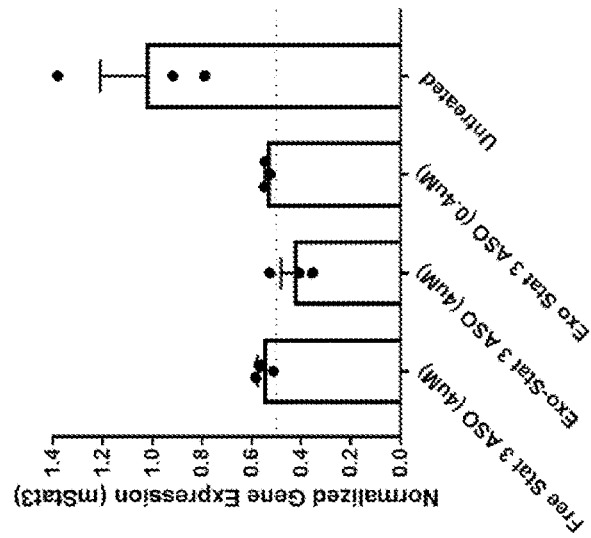
FIG. 8C shows C/EBPβ expression in M2 polarized murine RAW264.7 cells after incubation with high (4 μM) and low (0.4 μM) doses of ASO or Exo-ASO for C/EBPβ.

Example 3: Exosome-Mediated Delivery of Antisense Oligos Potently Dysregulates Macrophage Transcriptional Networks and Alters Polarization The previous experiments suggest that exosome-mediated delivery of ASOs may be an effective method of altering macrophage gene expression patterns. HEK293 SF-derived exosomes purified according to the above methods were loaded with one of five different cholesterol-tagged ASOs targeting STAT3 (4.1, double-stranded MOE chemistry; 5.1 and 5.2, single-stranded O-methyl chemistry; 5.3 and 5.4, single-stranded MOE chemistry). The ASO sequences are shown in Table 0. M2 polarized murine RAW264.7 cells were incubated with 5 µM free cholesterol-tagged ASO or either $1 \times 10^5$ or $1 \times 10^6$ exosomes loaded with the cholesterol-tagged ASO. STAT3 transcript levels were measured 24 hours after treatment, revealing comparable or superior knockdown of STAT3 with Exo-ASO treatment as compared to free ASO. Unmodified exosomes incubated with the polarized macrophages had no impact on STAT3 expression (FIG. 6). To examine downstream targets of STAT3, ARG1 transcript levels were measured 48 hours after treatment. As shown in FIG. 7, STAT3 knockdown with free ASO or Exo-ASO led to robust repression of Arg1, in several cases by more than 90% (FIG. 7). M2-polarized RAW264.7 cells were incubated with high (4 µM) and low (0.4 µM) ASO or Exo-ASO for STAT3, KRAS, and C/EBPβ. As shown in FIGS. 8A-C, Exo-ASO samples were equally (STAT3) or more potent (KRAS, C/EBPβ) at all tested doses (FIGS. 8A-C). The ASO sequences are shown in Table 0.

This result demonstrates that Exo-ASO is a potent modulator of macrophage expression networks, and may provide a superior, differentiated modality, as compared to administration of free ASO for various therapeutic applications. One such method to modulate gene expression in a macrophage, comprising administering to a subject an Exo-ASO, wherein said ASO is targeted to the gene, and wherein the modulation is equal to or greater than modulation produced by administration of an equimolar amount of free ASO targeted to the gene. Another embodiment comprises a method of inhibiting gene expression in a macrophage, comprising administering to a subject an Exo-ASO, wherein said ASO is targeted to the gene, and wherein the inhibition is equal to or greater than inhibition produced by administration of an equimolar amount of free ASO targeted to the gene. Another embodiment comprises a method of repressing a downstream target of a gene in a macrophage, comprising administering to a subject an Exo-ASO, wherein said ASO is targeted to the gene, and wherein the repression is equal to or greater than repression produced by administration of an equimolar amount of free ASO targeted to the gene. Yet another embodiment comprises a method of altering polarization of a population of macrophages, comprising administering to a subject an Exo-ASO, wherein said ASO is targeted to a gene expressed in the macrophages, and wherein the alteration of polarization is equal to or greater than alteration of polarization produced by administration of an equimolar amount of free ASO targeted to the gene. In such embodiments the alteration in polarization can be a change from an M2 to an M1 phenotype.

Figure 9A:
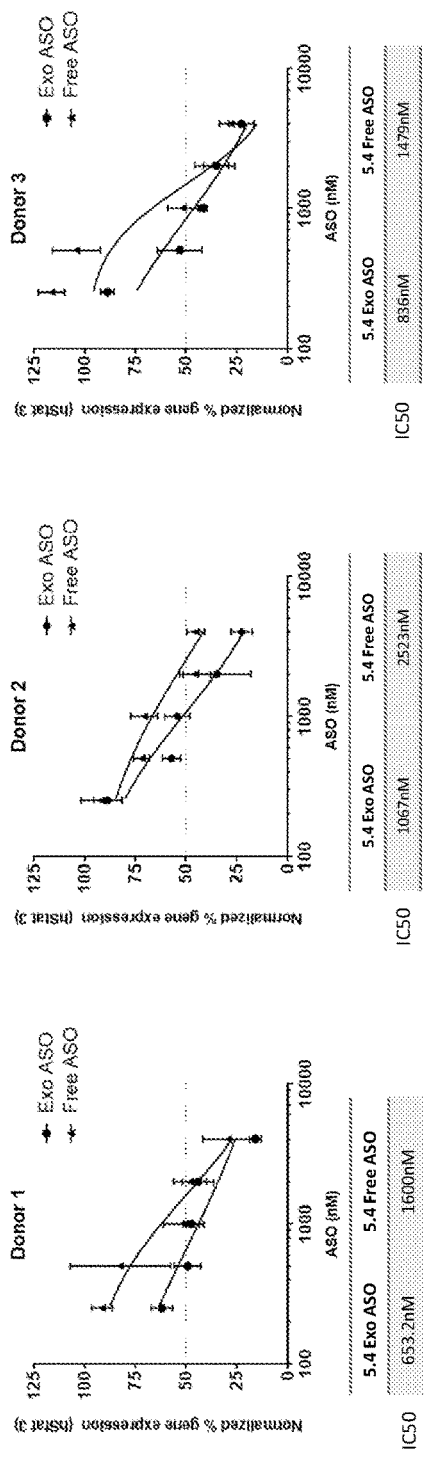
FIG. 9A shows STAT3 transcript level in primary human macrophages from three separate donors after treatment with varying doses of free STAT3 ASO or STAT3 Exo-ASO. The IC50 of each treatment and the fold improvement of STAT3 Exo-ASO compared to free STAT3 ASO are presented.
Figure 9B:
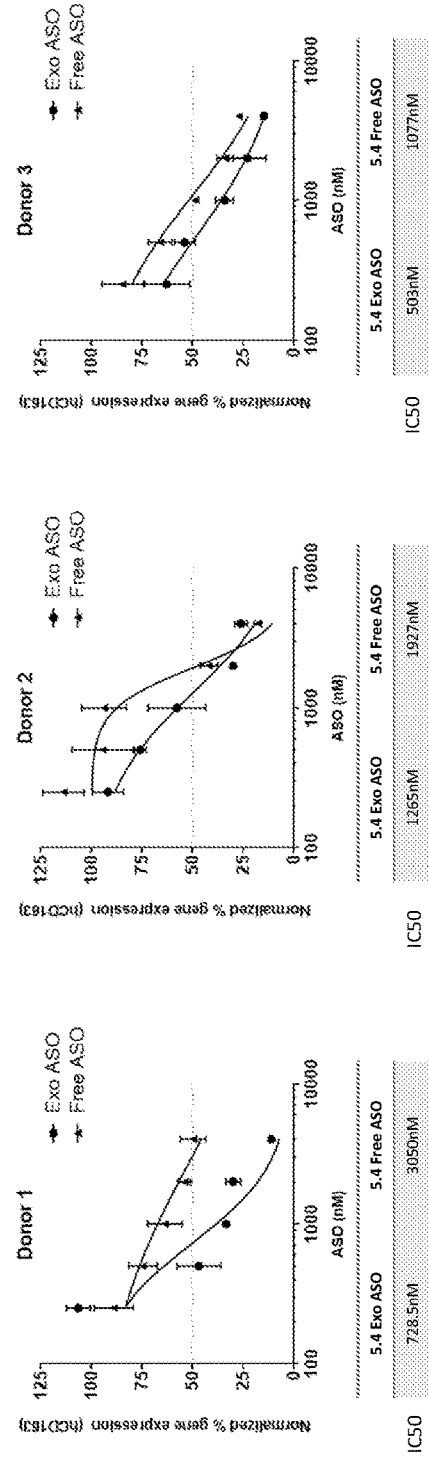
FIG. 9B shows CD163 level in primary human macrophages from three separate donors after treatment with varying doses of free STAT3 ASO or STAT3 Exo-ASO. The IC50 of each treatment and fold improvement of STAT3 Exo-ASO compared to free STAT3 ASO are presented.
Figure 10:
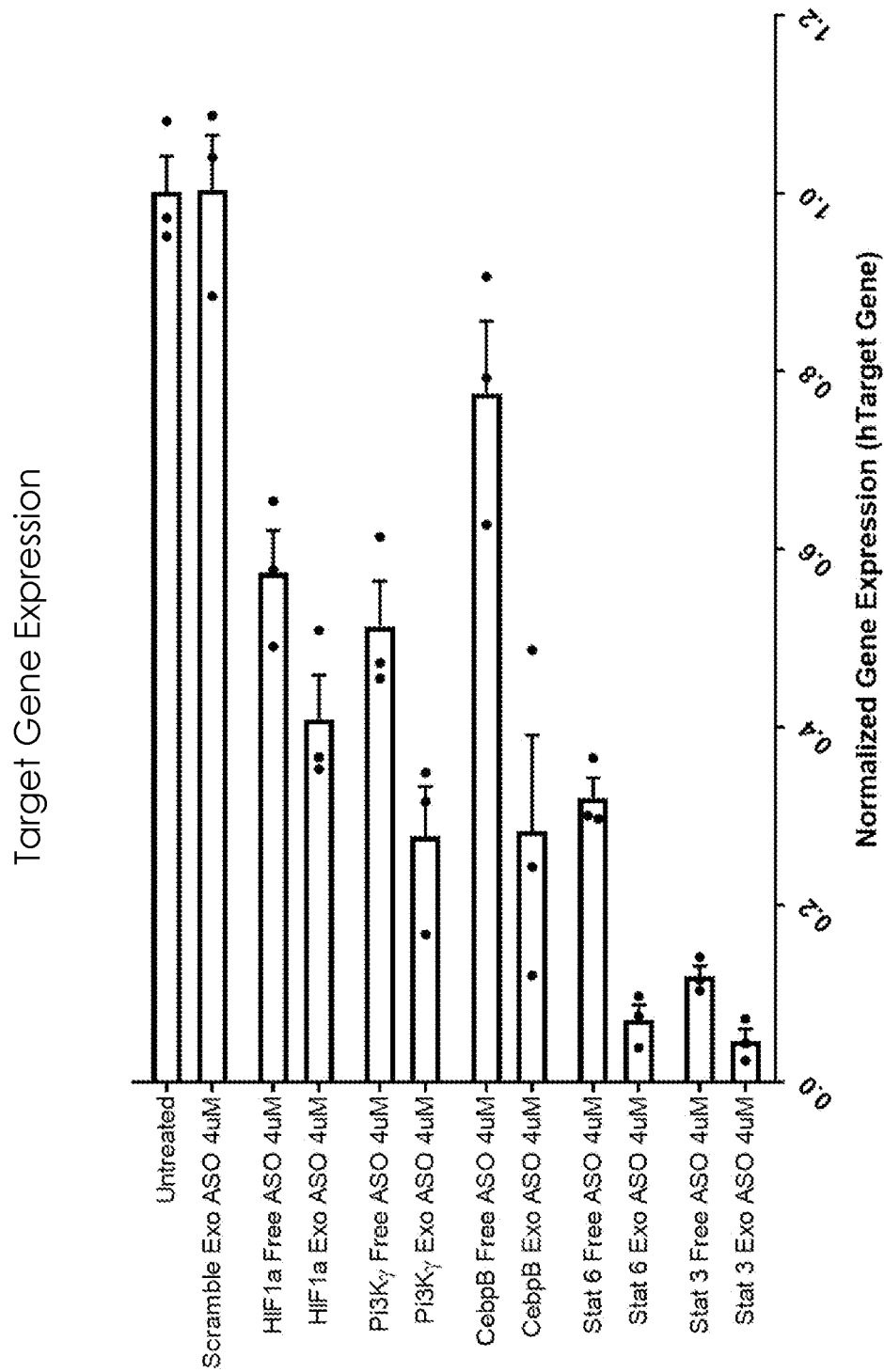
FIG. 10 shows the target gene expression in human M2 macrophages after treatment with 4 μM free ASO or Exo-ASO for HIF1α, Pi3Kγ, CEBP/β, STAT6, and STAT3 respectively. Untreated human M2 macrophages and human M2 macrophages treated with 4 μM scrambled Exo ASO were used as control.
Figure 11:
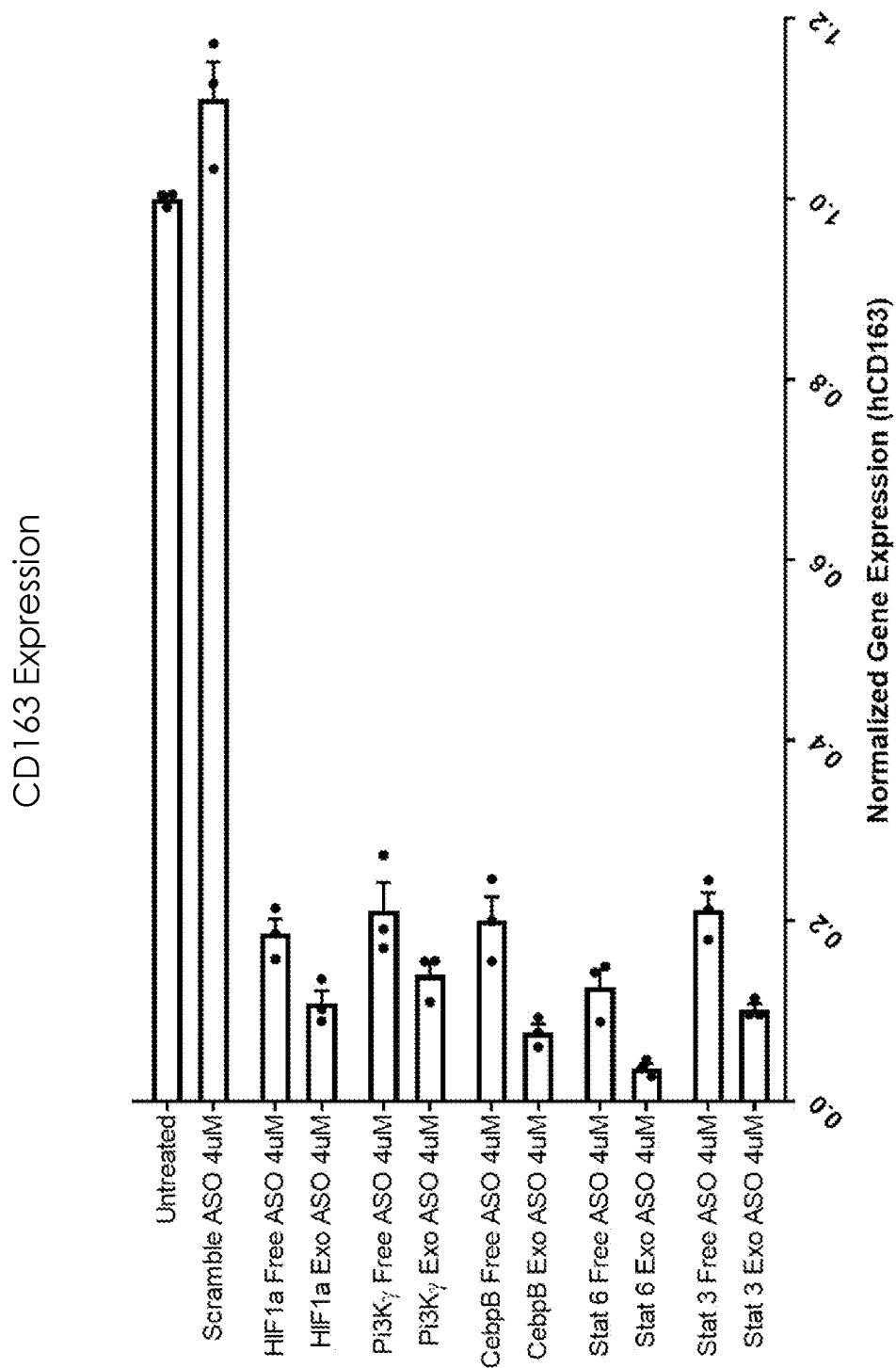
FIG. 11 shows CD163 expression in human M2 macrophages after treatment with 4 μM free ASO or Exo-ASO for HIF1α, Pi3Kγ, CEBP/β, STAT6, and STAT3 respectively. Untreated human M2 macrophages and human M2 macrophages treated with 4 μM scrambled Exo ASO were used as control.

To test the role of Exo-ASO in human cells, primary human macrophages were polarized to an M2 phenotype and treated with varying doses of a free STAT3 ASO or STAT3 Exo-ASO. Using macrophages from three separate human donors, Exo-ASO was consistently more potent in repressing STAT3 transcript levels 24 hours after treatment (FIG. 9A). The downstream human marker of M2 polarization, CD163, was also more dramatically modulated by Exo-ASO compared to free ASO (FIG. 9B). Human M2 macrophages were also treated with 4 µM free ASO or Exo-ASO for HIF1α, Pi3Kγ, CEBP/β, STAT6, and STAT3. As shown in FIG. 10, all treatment groups resulted in the repression of the target gene, but in all cases Exo-ASO was more potent than the free ASO treatment. Importantly, Exo-ASO knockdown of any of the macrophage targets led to robust reduction in CD163 expression (FIG. 11), demonstrating that exosome-mediated delivery of ASOs potently and reproducibly disrupts important macrophage signaling networks.

Figure 12B:
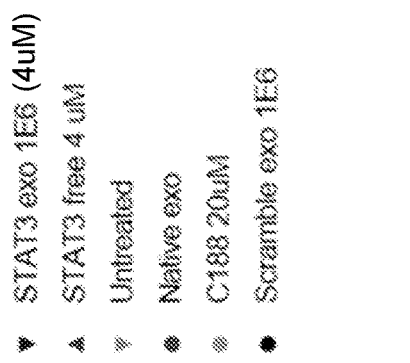
FIG. 12B shows the induction of IL-23 after treatment with 4 μM free STAT3 ASO, 4 μM STAT3 Exo-ASO, 4 μM scrambled Exo-ASO, native exosomes, or C188-9, a small molecule inhibitor of STAT3 in the presence or absence of LPS.
Figure 12B:
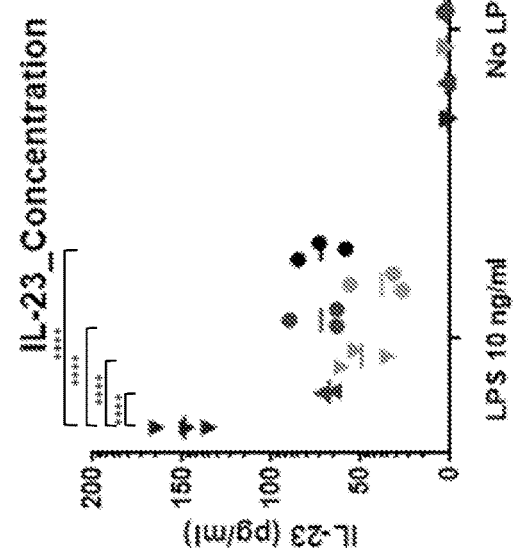
Figure 12A:
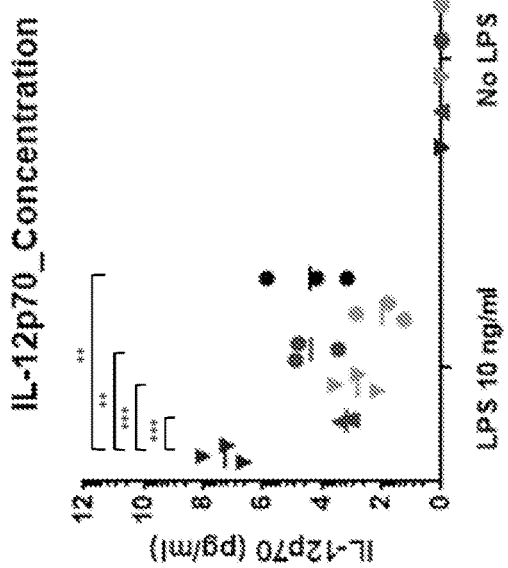
FIG. 12A shows the induction of IL-12 after treatment with 4 μM free STAT3 ASO, 4 μM STAT3 Exo-ASO, 4 μM scrambled Exo-ASO, native exosomes, or C188-9, a small molecule inhibitor of STAT3 in the presence or absence of LPS.

A functional consequence of M2 macrophage polarization is a reduction in pro-inflammatory cytokines, which contribute to a pro-tumorigenic microenvironment. Conversion of macrophages from M2 to M1 phenotype should therefore result in enhanced pro-inflammatory signaling. Conversion of M2 macrophages to the M1 state can be induced by LPS, which leads to the induction of cytokines including IL-12 and IL-23. STAT3 is a negative regulator of this cytokine expression network, and thus we tested whether STAT3 inhibition in the presence of LPS can further enhance the production of pro-inflammatory cytokines. M2-polarized human macrophages were treated with 4 µM free STAT3 ASO, 4 µM STAT3 Exo-ASO, 4 µM scrambled Exo-ASO, native exosomes, or C188-9, a small molecule inhibitor of STAT3. 24 hours later, media was exchanged to media containing 10 ng/ml LPS, and supernatant was isolated 24 hours later. As shown in FIG. 12, LPS induced the secretion of IL-12 and IL-23 (LPS 10 ng/ml group vs. No LPS group). Treatment with STAT3 Exo-ASO but not free STAT3 ASO further enhanced the expression of each cytokine, suggesting that Exo-ASO can more potently lead to the promotion of an M1 phenotype in response to relevant immunomodulatory signals.

Figure 13A:
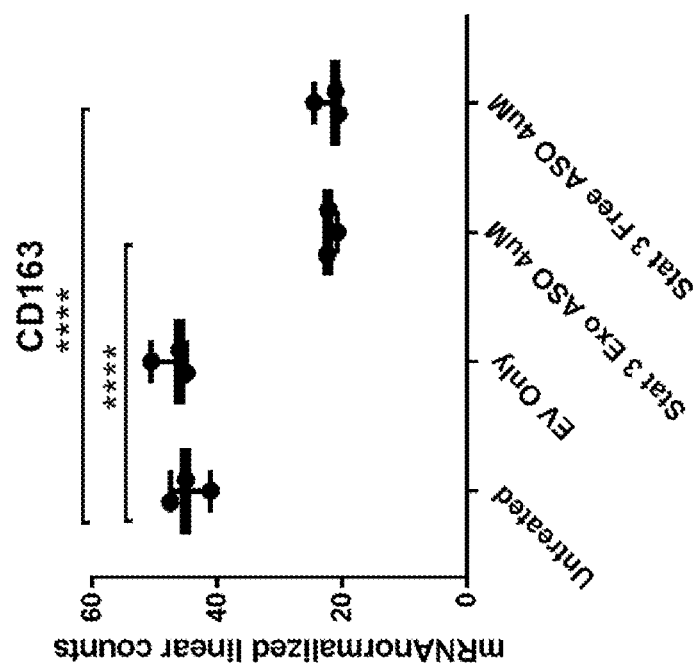
FIG. 13A shows the STAT3 transcript level after treatment with unmodified exosomes (EV only), and concentration-matched Stat 3 Free ASO and Stat 3 Exo-ASO.
Figure 13B:
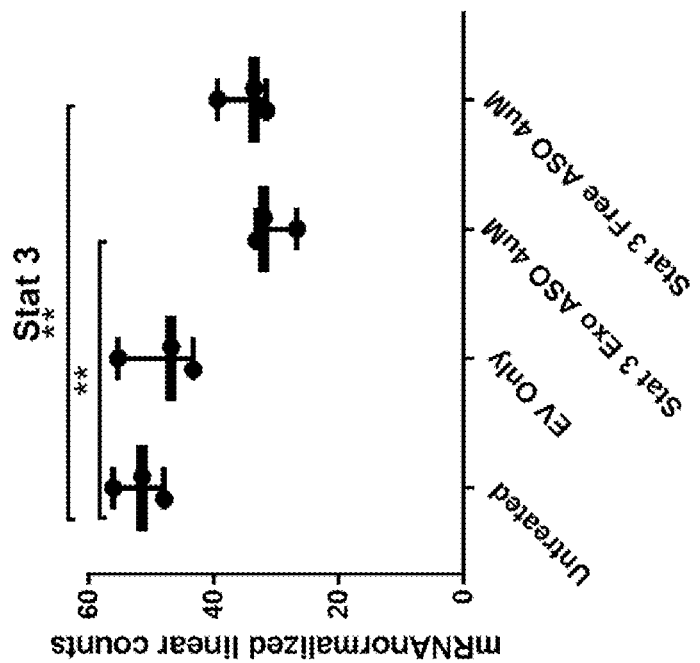
FIG. 13B shows the CD163 transcript level after treatment with unmodified exosomes (EV only), and concentration-matched Stat 3 Free ASO and Stat 3 Exo-ASO.
Figure 13C:
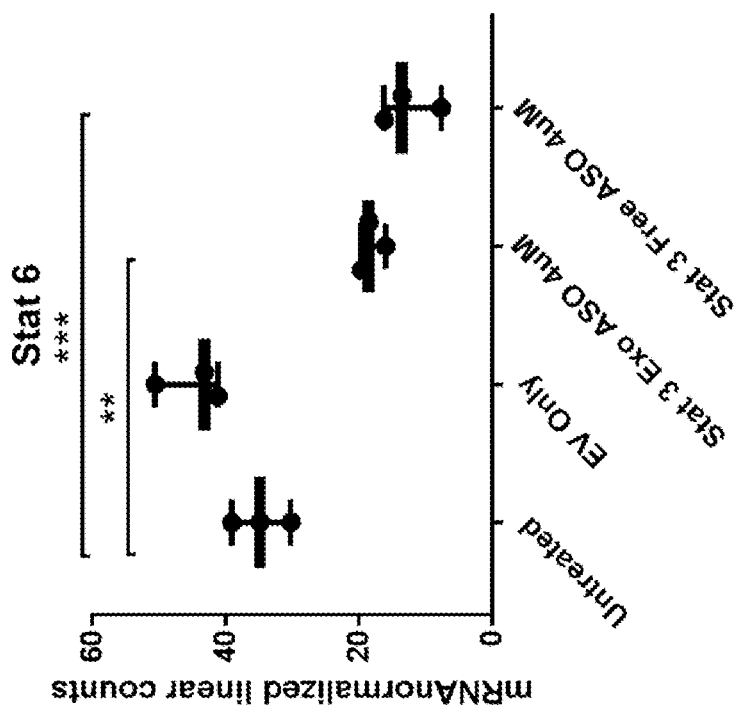
FIG. 13C shows the TGFβ transcript level after treatment with unmodified exosomes (EV only), and concentration-matched Stat 3 Free ASO and Stat 3 Exo-ASO.
Figure 13D:
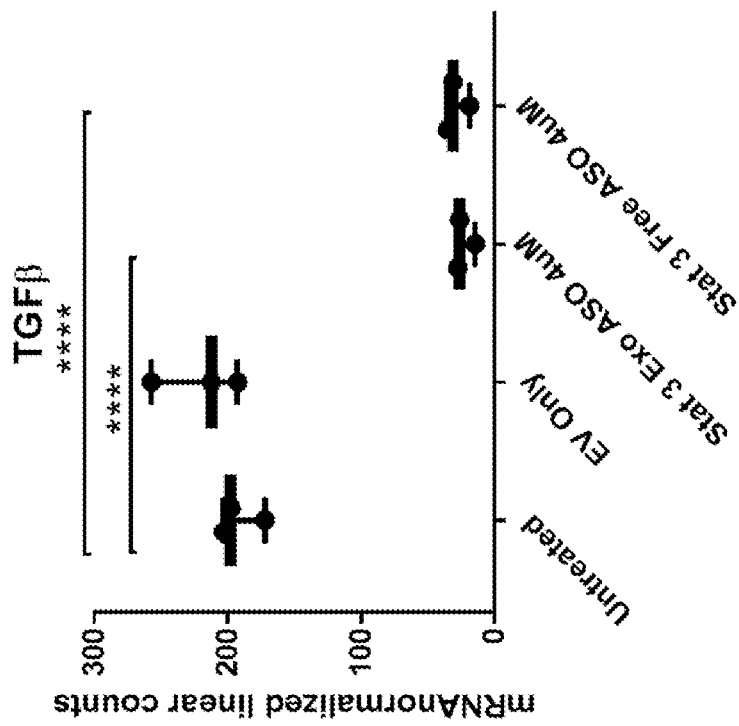
FIG. 13D shows the STAT6 transcript level after treatment with unmodified exosomes (EV only), and concentration-matched Stat 3 Free ASO and Stat 3 Exo-ASO.

Dysregulation of STAT3, STAT6, and the other macrophage modulatory pathways leads to broad changes in gene expression patterns. To understand the differentiated global impact of Exo-ASO treatment, NanoString mRNA analysis was carried out on human M2 macrophages at their steady state and in response to treatment with unmodified exosomes (EV only), and concentration-matched ASO and Exo-ASO. Normalized mRNA counts using the nCounter® Human Myeloid Innate Immunity Panel demonstrated that STAT3 transcripts were reduced after both free ASO and Exo-ASO treatment (FIG. 13A). Downstream markers CD163 (FIG. 13D), TGFβ (FIG. 13C), and STAT6 (FIG. 13D) were all potently downregulated after ASO treatment.

Figure 14:
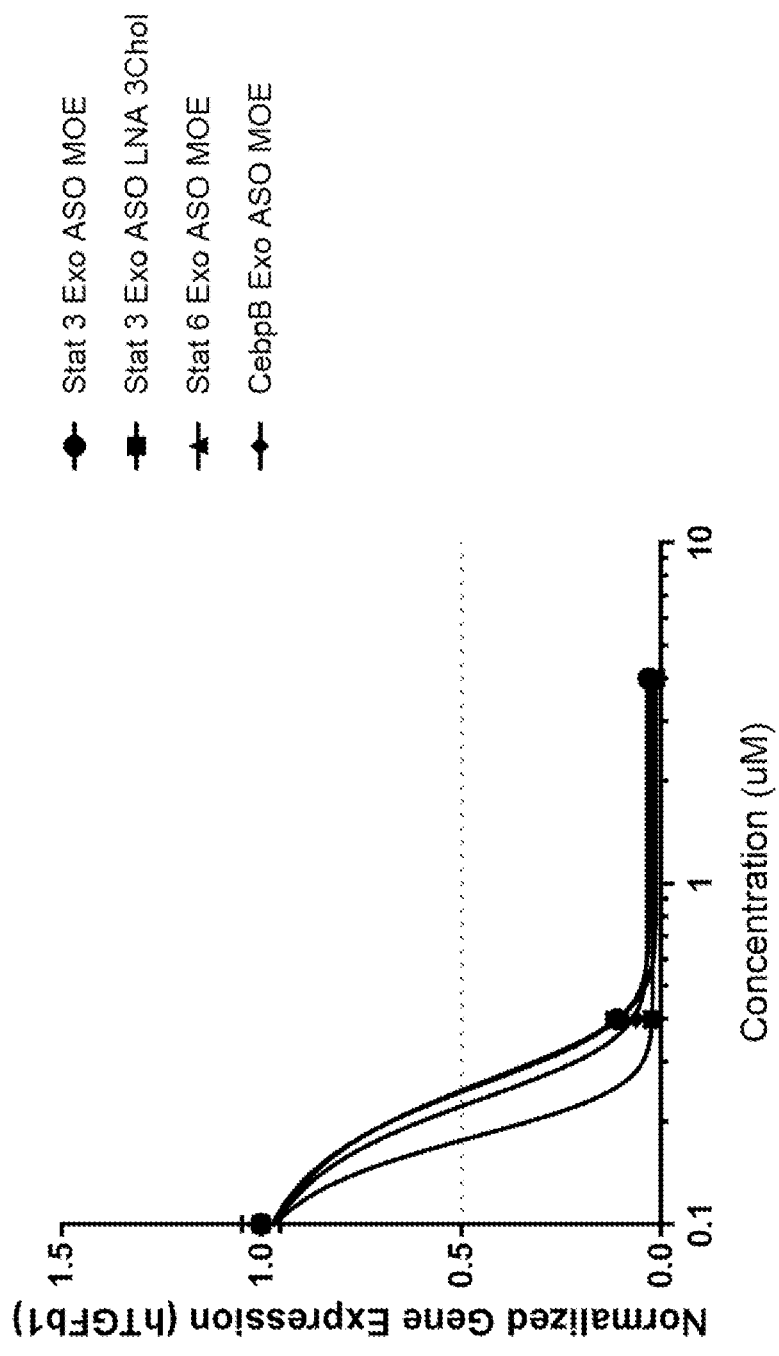
FIG. 14 shows the TGFβ expression level after treatment with exosomes loaded with ASOs against STAT3 (both MOE and LNA chemistry), STAT6 (MOE chemistry), and CEBP/β (MOE chemistry) respectively.

Robust repression of TGFβ (<85%) is a critical regulator of M2 macrophage polarization, (Yang and Zhang Journal of Hematology & Oncology (2017) 10:58). We examined the impact of STAT3, STAT6, and CEBP/β Exo-ASO treatment on TGFβ expression. Human M2-polarized macrophages were treated with exosomes loaded with ASOs against STAT3 (both MOE and LNA chemistry), STAT6 (MOE chemistry), and CEBP/β (MOE chemistry). In all cases, TGFβ levels were dramatically reduced after treatment with sub-micromolar levels of ASO (FIG. 14). These results demonstrate that exosome-mediated delivery of ASOs against numerous macrophage polarization regulators can lead to robust, stable dysregulation of cellular programs that may be impactful in the treatment of numerous cancers. Importantly, each of the macrophage targets, including the novel recognition of KRAS as a regulator of this process, have been characterized as "undruggable" targets, in that their role in disease and other cellular processes is well-recognized, but safe, effective treatment has eluded classical approaches of drug development.

Example 4: Inhibition of Wild-Type KRAS Leads to Increased Macrophage Polarization and Reduced Tumor Size In Vivo in an Orthotopic Mouse Model of Pancreatic Cancer Methods:

Production and isolation of KRAS exosomes: Electroporation methods are used to insert KRAS siRNA constructs into exosomes without functionally damaging exosomes. Exosomes are isolated from human embryonic kidney (HEK) 293SF suspension cells grown in chemically-defined medium using established ultracentrifugation methods (Kahlert et al., 2014). The purity and homogeneity (80-150 nm diameter particles) of the exosomes is validated by Nanosight™ measurements, transmission electron microscopy, and CD9 immunogold labeling. Sucrose gradient ultracentrifugation and qPCR are also performed to validate the presence and abundance of the KRAS siRNA. Scrambled siRNA containing exosomes are also generated.

RNAi strategies. The KRAS siRNA sequence targeted against mouse wild-type KRAS comprises a TT nucleotide overhang to promote silencing efficiency. The RNAi is also labeled with an Alexa Fluor® 647 fluorophore at the 3' end on the sense strand to track its delivery.

Mice and imaging. Female athymic nu/nu mice (Charles Rivers) between 4-6 weeks of age are housed in individually ventilated cages on a 12 h light-dark cycle at 21-23° C. and 40%-60% humidity. Mice are allowed free access to an irradiated diet and sterilized water. Under general anesthesia, tumorigenic human pancreas Panc-1 ($Kras^{asp12}$ (Rejiba et al., 2007; Sun et al., 2001)) cells or BXPC-3 cells ($10^6$, resuspended in 10 µl PBS) are injected into the tail of the pancreas using a 27-gauge syringe. For orthotopic tumor size/volume analyses, Living Image version 4.4 (Caliper Life Sciences) is used to quantify all tumor calculations. A circular region of interest (ROI) around the pancreas and tumor is defined and set as a standard to compare all the images within the same experimental group. In addition, exposure conditions (time, aperture, stage position, binning) are kept identical for all measurements in all experimental groups. Subsequent tumor measurements (p/sec/cm²/sr) are then obtained under the same conditions for all experimental groups. The mice are imaged regularly and randomly divided into groups for treatments. Mice receive $2\times10^8$ exosomes i.p. in 100 µl volume of PBS every other day. Exosomes are electroporated with 2 µg of siRNA and washed with PBS prior to injection.

Histology, histopathology, and immunohistochemistry. Tissues are fixed in formalin and processed for paraffin embedding. Tissue sections of 5 µm thickness are cut and stained for hematoxylin and eosin (H&E) and Masson's trichrome (MTS) (Leica). For histopathological scoring, H&E stained slides were scored based on the morphological stages of pancreas cancer: Normal, pancreatic intraepithelial neoplasia (PaNIN) and pancreatic ductal adenocarcinoma (PDAC). For each tissue section, a percentage score for each of the three stages (Normal, PaNIN, PDAC) is obtained manually in a blinded fashion by experts in pancreas histology, which was then averaged to give an overall score out of 100 for each cohort. An average of these percentage scores is then taken for each mouse in the respective cohorts. Tumor tissue sections are also stained for macrophages (with either pan-macrophage markers (e.g., F4/80 antibody and/or M2 and M1 specific cell markers for detection of tumor resident macrophages).

Assays for Macrophage phenotype characterization. Blood samples and tumor samples are collected from mice. Macrophages are isolated and stained for analyses of M1 and M2 markers by flow cytometry. Macrophages are stained for pan-macrophage markers as well as M2 phenotype cell surface markers (e.g., YM1, FIZZ1, Dectin-1 and/or MGL) and M1 phenotype cell surface markers. M2 and M1 macrophages are then counted and sorted for further analyses, such as quantitative PCR to detect cytokine and/or miRNA expression of miRNAs associated with either M1 and/or M2 phenotype).

The results from the xenograft experiments and orthotopic tumor volume analyses confirm that exosomes comprising KRAS wild-type siRNA effectively reduce the size of pancreatic tumors and increase the number of M1 phenotype tumor associated macrophages compared to exosomes harboring a scrambled siRNA, indicating that administration of exosomes comprising inhibitory RNA targeted against human wild-type KRAS is effective for the treatment of cancer.

TABLE 0

| | Sequences of antisense oligonucleotides (ASOs) | |
|---|---|---|
| Target | Sequence | SEQ ID NO: |
| Stat3 | TAAGCTGATAATTCAACTCA | SEQ ID NO:1 |
| Stat6 | TGAGCGAATGGACAGGTCTT | SEQ ID NO:2 |

TABLE 0-continued

Sequences of antisense oligonucleotides (ASOs)

| Target | Sequence | SEQ ID NO: |
|---|---|---|
| CebpB | TGGATTTAAAGGCAGGCGGC | SEQ ID NO:3 |
| Pi3Kγ | TTGGGTAAAGTCGTGCAGCA | SEQ ID NO:4 |
| HIF1-α | GTGCAGTATTGTAGCCAGGC | SEQ ID NO:5 |
| Kras | GTAGCATGTAAATATAGCCC | SEQ ID NO:6 |

All antisense oligonucleotides have a phosphorothioate bond between each nucleotide.

TABLE 1

Exosome lipids

| | |
|---|---|
| Lysobisphosphatidic acid | Ganglioside GM3 24:1 |
| Sphingomyelin (SM) | Ganglioside GM3 16:0 |
| Ganglioside GM3 | PE40:5 |
| Phosphatidylserine (PS) | PE40:6 |
| Phosphatidylinositol (PI) | PE38:3 |
| Phosphatidylcholine (PC) | PE38:4 |
| Phosphatidylethanolamine (PE) | PE36:1 |
| Lysophosphatidylcholine (LPC) | PE36:2 |
| Cholesterol (Chol) | PE34:1 |
| Diacylglycerol (DG) | PE34:2 |
| PI18:0/20:3 | PE-ether38:5 |
| PI18:0/20:4 | PE-ether38:6 |
| PI18:0/18:1 | PE-ether34:1 |
| PI18:1/18:1 | PE-ether34:2 |
| PI18:0/16:0 | PC34:1 |
| PA18:0/18:1 | PC36:4 |
| PS18:0/18:1 | PC34:3 |
| BMP18:0/18:1 | PC32:0 |
| BMP18:1/18:1 | PC30:0 |
| BMP18:1/16:0 | SM24:1 |
| CL(18:1)3/16:1 | SM16:0 |
| CL(18:1)2/(16:1)2 | Dihydrosphingomyelin16:0 |

TABLE 2

Exosome polypeptides

| | | | |
|---|---|---|---|
| ACLY | TCP1 | ACTR1A | LY75 |
| ACTB | PRDX2 | THOC4 | ABCC1 |
| ACTG1 | TSPAN6 | INADL | MYO1E |
| ALB | CCT3 | CTDSPL | NACA |
| ALDOA | TSTA3 | ZMPSTE24 | NAP1L4 |
| ALDOB | TUBA3C | DNAJA2 | NCL |
| AKR1B1 | HIST1H2AK | NDRG1 | NEDD8 |
| AMBP | HIST1H2AJ | RAP GEF3 | YBX1 |
| ANPEP | HIST1H2AB | SP ON2 | PA2G4 |
| ANXA2 | HIST2H2AC | UBAC1 | PECAM1 |
| ANXA3 | IFITM1 | N4BP2L2 | PFAS |
| ANXA4 | PDXK | CAP1 | SERPINB9 |
| ANXA5 | LIN7A | VAT1 | PI4KA |
| ANXA6 | BUB3 | NEBL | PLAT |
| ANXA7 | MAP4K4 | DCTN2 | PLCG2 |
| ANXA11 | EDIL3 | ARPC1A | PPA1 |
| | ATP6AP2 | C6orf108 | PPP2CA |
| CAPZB | PSME3 | SMC2 | PRKCB |
| CD63 | TUBB3 | AHSA1 | PSMA6 |
| CD81 | IFITM3 | STAMBP | PSMA7 |
| CKB | ACAA2 | PMVK | PSMB8 |
| CLU | CCT7 | GIPC1 | PSMB9 |
| CLIC1 | CCT4 | HBS1L | PSMD7 |
| TPP1 | IFITM2 | NCKAP1 | P SME1 |
| CLTC | GNA13 | ALDH1L1 | PTPRA |
| CNP | RUVBL2 | FTCD | RAC2 |
| COL6A1 | PRSS23 | FGL2 | RPL3 |
| CR1 | ACOT7 | CFHR3 | RPL4 |
| CTNND1 | CCT5 | MMP24 | RPL5 |
| ACE | DIP2C | COPS8 | RPL11 |

TABLE 2-continued

Exosome polypeptides

| | | | |
|---|---|---|---|
| DDT | ASCC3L1 | CKAP4 | RPL22 |
| DEFA1 | TNIK | C10orf116 | RPL24 |
| DEFA3 | NEDD4L | SLC27A2 | RPL27 |
| DNAH8 | NCSTN | MID2 | RPL30 |
| DPEP1 | TSPAN15 | KIF3A | RPL28 |
| DPP4 | PLXNB2 | NUDT5 | RPL31 |
| EEF1A1 | SDCBP2 | TREH | RPL34 |
| EEF2 | IGKV1-5 | CEP250 | RPL35A |
| EGF | IGHV4-31 | PDCD10 | RPL37A |
| EIF5A | IGKV3-20 | PADI2 | RPS2 |
| ENO1 | IGKV2-24 | PACSIN2 | RPS3A |
| ENO3 | MINK1 | CHP | RPS5 |
| ENPEP | IGKα | SNF8 | RP S9 |
| STOM | VPS36 | DDX19B | RPS19 |
| EPS8 | DERA | SCN11A | RPS25 |
| FABP3 | GOLGA7 | LYPLA2 | RPS26 |
| FGA | KRT76 | PARK7 | RPS28 |
| MLANA | EIF3EIP | COBLL1 | RPS29 |
| FN1 | LSR | CNKSR2 | RSU1 |
| FTL | TUBA8 | ENPP4 | SARS |
| FUS | RAB4B | RAB3GAP1 | SLAMF1 |
| GAA | SETD4 | AKR7A3 | SLC1A4 |
| GAPDH | TOLLIP | SPEN | SLC2A3 |
| GDI2 | PLEKHB2 | GANAB | SNRPD2 |
| GGT1 | VPS37C | MGRN1 | SPINK1 |
| GLB1 | LIN7C | CUX2 | SPN |
| GLG1 | H2AFJ | DNAJC13 | STK10 |
| GNA11 | CAND1 | ZCCHC11 | STXBP3 |
| GNAI1 | PLSCR3 | PHF15 | TALD01 |
| GNAI2 | KIAA1199 | KIAA0841 | TNFAIP3 |
| GNAI3 | GNB4 | ARHGEF12 | TPM3 |
| GNAS | MYH14 | COTL1 | TPM4 |
| GNB1 | TSPAN14 | ANGPTL2 | TYK2 |
| GNB2 | NCALD | DDAH2 | VIM |
| GNG7 | REG4 | HEBP2 | WARS |
| SFN | VPS25 | CD2AP | WAS |
| GPI | TUBB6 | PLD3 | LAT2 |
| GSTA1 | TUBA1C | TMEM2 | HI5T1H2BL |
| GSTA2 | TNKS1BP1 | SH3BP4 | STX7 |
| GSTA3 | FAM125B | BHMT2 | CPNE1 |
| GSTM3 | LRSAM1 | GCA | RPL14 |
| GSTP1 | HIST2H2A | MXRA5 | PDCD5 |
| GUSB | TUBA3E | AHCTF1 | SYNGR2 |
| HIST1H2AD | TUBA3D | PTPN23 | RPL23 |
| HLA-A | DCD | DAK | RAB9A |
| HLA-B | HIS T4H4 | ACOT11 | IGSF2 |
| HLA-DQB1 | ALDH16A1 | APPL1 | EEF1E1 |
| HLA-DRA | RP S4Y2 | PHGDH | SCAMP2 |
| HLA-DRB1 | MYL6B | TIAM2 | SCAMP3 |
| HLA-DRB5 | BRI3BP | KCNG2 | DPP3 |
| HPGD | AGR3 | CYFIP2 | ARPC1B |
| HRAS | EEF1AL3 | GHITM | PDIA6 |
| HSPA1A | KRT28 | C11orf54 | WASF2 |
| HSPA1B | KRT24 | DBNL | ANP32B |
| HSPA8 | RPLP0-like | ATAD2 | PAICS |
| HSP90AA1 | RPSAP15 | PHPT1 | AHCYL1 |
| | RANP1 | C16orf80 | VAMP5 |
| KRT1 | PCSK9 | OLA1 | 41891 |
| KRT9 | METRNL | ZDHHC1 | HSPH1 |
| KRT10 | LOC284889 | SNX12 | SUB1 |
| LDHA | KRT6C | PSAT1 | CDC37 |
| LDHB | KRT79 | NT5C | CORO1A |
| TACSTD1 | RAB43 | EHD2 | CD300A |
| MCAM | KRT27 | TAX1BP3 | TMC6 |
| MDH1 | ACTBL2 | CRNN | RFTN1 |
| MEP1A | RP11-631M21.2 | NOX3 | SCRIB |
| MSN | TUBB2B | ATP6V0A4 | SERBP1 |
| 2-Sep | KRT77 | ITSN2 | TTLL3 |
| PGAM1 | AGRN | GEMIN4 | CACYBP |
| PGK1 | RAB15 | LAP3 | SIT1 |
| PKM2 | LOC388524 | CRYL1 | SLC43A3 |
| PPP1CA | LOC388720 | MYO15A | PILRA |
| | HSP90AB2P | ATP6V1D | RPL26L1 |
| PTPRC | ACTBL3 | SNX9 | MPP6 |
| RAN | LOC442497 | PCYOX1 | GNG2 |
| RDX | A26C1A | ANKFY1 | TMED9 |
| SDCBP | HIST2H4B | UFC1 | DOCK10 |
| STX3 | hCG_1757335 | FAM49B | C3orf10 |

TABLE 2-continued

Exosome polypeptides

| | | | |
|---|---|---|---|
| STXBP1 | HLA-A29.1 | CUTA | MYO1G |
| STXBP2 | LOC653269 | ATP6V1H | FLJ21438 |
| TPI1 | A26C1B | VPS24 | SLC38A1 |
| EZR | LOC100128936 | CMPK1 | FERMT3 |
| YWHAE | LOC100130553 | UPB1 | ITFG3 |
| TUBA1A | LOC100133382 | CLIC5 | HIST1H2AH |
| WDR1 | LOC100133739 | MUPCDH | SLAMF6 |
| PDCD6IP | AP2A2 | CLIC6 | TMC8 |
| GPA33 | ALDH3B1 | SIAE | LOC153364 |
| TUBA1B | FASLG | CPVL | SVIP |
| TUBB2C | ATP4A | RHOF | TMEM189-UBE2V1 |
| CAPN7 | CAPS | ARL15 | hCG_16001 |
| DDAH1 | COL12A1 | ZNHIT6 | FABP5L7 |
| PGLS | DMBT1 | GIPC2 | Del(X)1Brd |
| SAMM50 | DSP | PCDH24 | ABP1 |
| CLIC4 | EGFR | VPS13C | ACTN3 |
| CHMP2B | EPHA5 | CC2D1A | AFM |
| ULK3 | EPHB1 | EPS8L1 | AKT1 |
| RNF11 | FAT | C10orf18 | ALDH3A2 |
| VPS4A | HSD17B4 | CHCHD3 | ALOX12P2 |
| ARFIP1 | L1CAM | C2orf18 | ANXA2P1 |
| CHMP2A | LAMA5 | C17orf80 | KRT33B |
| SMPDL3B | MUC4 | EPN3 | MYOC |
| PACSIN3 | NOTCH1 | UACA | SERPINE1 |
| EHD4 | PPP2R1B | VPS13D | PIK3CA |
| EHD3 | PTPRF | APPL2 | NRP1 |
| HEBP1 | SORT1 | ARL8B | SPRY1 |
| VPS28 | SERPINB3 | DDX19A | EMILIN1 |
| DCXR | SELP | NAGK | LRG1 |
| RHCG | FSCN1 | ITLN1 | AZGP1P1 |
| CHMP5 | TGFB1 | CCDC132 | LOC728533 |
| VTA1 | CLTCL1 | OTUB1 | ALDH7A1 |
| RAB14 | CHST1 | CDK5RAP2 | AXL |
| GPRC5B | EIF3I | MBD5 | CFB |
| CAB39 | TNFSF10 | SLC22A11 | C1S |
| RAB8B | MAP7 | SUSD2 | CAT |
| TM7SF3 | COPB2 | SUCNR1 | CD47 |
| MXRA8 | HEPH | BDH2 | CD151 |
| C11orf59 | | NIT2 | CDH13 |
| MOBKL1B | CIB1 | RPL23AP13 | CFTR |
| UEVLD | SLC34A2 | FAM20C | CEACAM8 |
| TSNAXIP1 | SLC6A14 | SLC12A9 | AP1S1 |
| GPRC5C | DIP2A | RAB25 | CLTA |
| GNG12 | TNP03 | SMURF 1 | CNGB1 |
| BAIAP2L1 | FER1L3 | TMEM27 | COL1A1 |
| MUC13 | CNTLN | RAB22A | COL1A2 |
| CHMP1B | TUBB4Q | NDRG3 | COL2A1 |
| SLC44A2 | KIF15 | ERMN | COL3A1 |
| CPNE5 | SERINC1 | TAOK1 | COL4A1 |
| TMBIM1 | PDIA2 | KIAA1529 | COL4A2 |
| EPS8L3 | EP S 8L2 | RNF213 | COL4A3 |
| MMRN2 | PLVAP | WIZ | COL5A1 |
| TTYH3 | MYADM | ACE2 | COL5A2 |
| SLC44A4 | MUC16 | PLEKHA1 | COL7A1 |
| RAB1B | KRT25 | SCPEP1 | COMP |
| RAB33B | SERINC5 | AASDHPPT | CPS1 |
| RBP5 | LOC440264 | FIGNL1 | CSF1 |
| C5orf32 | AGT | PBLD | VCAN |
| ABHD14B | ALPP | KIF9 | SLC25A10 |
| MOBKL1A | APOA2 | LEPRE1 | CTBP2 |
| ARRDC1 | APOB | RAB17 | CTNNA2 |
| | APOE | IKZF5 | DCTN1 |
| FAM125A | SERPING1 | MMP25 | DECR1 |
| SNX18 | C1QB | MPP5 | DNASE1L1 |
| CHMP4B | C1R | TEKT3 | ENG |
| MITD1 | C4A | ALDH8A1 | STX2 |
| S100A16 | C4B | SLC13A3 | ETFB |
| CPNE8 | C4BPA | DUSP26 | F2R |
| C1orf58 | C4BPB | GGCT | F8 |
| GLIPR2 | CD5L | TMEM38A | ACSL1 |
| TUBB | FCN1 | C1orf116 | FAP |
| ATP6V1C2 | FCN2 | GDPD3 | FBLN1 |
| FTLL1 | FGB | OR2A4 | FBN1 |
| PEF1 | FGG | FAM65A | FBN2 |
| SERPINA3 | GRIN1 | NARG1L | FEN1 |
| ACP2 | MSH6 | CHMP6 | FLT1 |
| ACPP | HBA1 | DYNC2H1 | FUCA2 |
| ACTA2 | HBA2B | PRKRIP1 | GAS6 |
| ACTC1 | ITGA2B | GSTCD | GDI1 |
| ACTG2 | PPARG | PIP4K2C | GLDC |
| ACY1 | PDLIM7 | CYBRD1 | GNAL |
| APCS | CD274 | FUZ | GRM2 |
| APOD | AlBG | ARMC9 | GRM3 |
| APRT | ACAT1 | NAT13 | GRM7 |
| AQP1 | AC01 | COASY | GSTM1 |
| AQP2 | ADCY1 | UBXN6 | GSTM5 |
| ARF1 | ADFP | COL18A1 | H2AFX |
| ARF3 | ADH5 | BHLHB9 | HBE1 |
| ARF4 | ADH6 | WNT5B | HMGCS2 |
| ARF5 | PARP4 | CAB39L | TNC |
| ARF6 | AHSG | ITM2C | IDH3B |
| ARL3 | AK1 | L0081691 | IFRD1 |
| RHOA | ALAD | AMN | ITGA5 |
| ASAH1 | ALCAM | SH3BGRL3 | ITGB5 |
| ASS1 | ALDH2 | C9orf58 | ITPR2 |
| FXYD2 | ALDH9A1 | BCL2L12 | KRT84 |
| BHMT | ALDOC | RAB34 | LAMB1 |
| BST2 | ALK | TBC1D10A | LCN1 |
| C3 | AL0X12 | GPR98 | LGALS8 |
| CA2 | ALPL | HDHD2 | LMNA |
| CA4 | ANXA13 | ARL6 | LOXL2 |
| CALB1 | A0X1 | IQCG | LTBP2 |
| CALR | APAF1 | C2orf16 | MAP1A |
| CD9 | AP0A4 | PARD6B | MAT1A |
| CD59 | SHROOM2 | TXNDC17 | MC1R |
| HSPA5 | RHOB | ABCC11 | MCC |
| HSPA6 | ARHGAP1 | FAM40A | ME1 |
| HSP90AB1 | ARHGDIB | SCIN | MECP2 |
| HSPD1 | ARSE | SCRN2 | MAP3K1 |
| IDH1 | ARSF | ZNF486 | MFAP4 |
| KNG1 | ASL | ACY3 | SCGB2A1 |
| KRAS | ASNA1 | C11orf52 | ALDH6A1 |
| LAMP1 | ATIC | CRB3 | MOS |
| LGALS3BP | ATP6V1A | C20orf114 | CITED1 |
| LRP2 | ATP6V1B1 | NAPRT1 | NEFH |
| MAN1A1 | ATP6V1B2 | RG9MTD2 | OPRM1 |
| RAB8A | ATP6VOC | SAT2 | OTC |
| MIF | ATP6V1C1 | KIF12 | OXTR |
| MME | ATP6V1E1 | MAL2 | PAPPA |
| MUC1 | ATP6V0A1 | OSBPL1A | PC |
| MYH9 | ATP6AP1 | VASN | PCOLCE |
| NAGLU | AZU1 | SLC22Al2 | PDGFRB |
| NONO | BCR | ACSM1 | PFKFB3 |
| NPM1 | BGN | TTC18 | PGAM2 |
| NRAS | BLMH | GSTO2 | SERPINE2 |
| P2RX4 | BLVRA | CLRN3 | PLP2 |
| P4HB | BLVRB | LRRK2 | PPP1CC |
| PEBP1 | BPI | C12orf59 | SRGN |
| SERPINA5 | BTG1 | LOC124220 | MAP2K6 |
| PFN1 | BTN1A1 | SLC5A10 | PSMB7 |
| PFN2 | TSPO | CCDC105 | PSMB10 |
| ABCB1 | C1QC | C1orf93 | PTK7 |
| SERPINA1 | CAPN5 | ARL8A | PTPRK |
| PIGR | C5 | L0C128192 | PZP |
| PIK3C2B | C9 | GALM | RAD21 |
| PKD1 | PTTG1IP | LRRC15 | RASA1 |
| PLSCR1 | CACNA2D1 | LOC131691 | RDH5 |
| PODXL | CALML3 | H1F00 | RPL18 |
| CTSA | CAMK4 | ENPP6 | RPL29 |
| PPIA | CAMP | CMBL | RPS10 |
| PSAP | CAPG | MUM1L1 | RPS24 |
| PSMB3 | CAPN1 | C20orf117 | S100A13 |
| PTBP1 | CAPN2 | SIRPA | SAA4 |
| PTPRJ | CAPZA2 | PLEKHA7 | ATXN1 |
| RAB1A | CD14 | A2ML1 | CLEC11A |
| RAB2A | CD80 | C16orf89 | SDC2 |
| RAB3B | CD36 | T0M1L2 | SMARCA4 |
| RAB5A | SCARB2 | KIF18B | SPOCK1 |
| RAB5B | CD40 | C19orf18 | STAT1 |
| RAB13 | CDC2 | PM20D1 | STC1 |
| RAB27B | CEL | PROM2 | SURF4 |
| RAB5C | CETP | GPR155 | SYT1 |
| RAC1 | CTSC | SLC36A2 | TAGLN |
| RALB | AP2M1 | VPS37D | TCN1 |
| RAP1B | CSN1S1 | SLC5Al2 | TERF1 |

TABLE 2-continued

Exosome polypeptides

| | | | |
|---|---|---|---|
| RBM3 | CSN2 | SLC5A8 | TGFB2 |
| RNASE2 | CSN3 | EML5 | TSPAN4 |
| S100A6 | ACSL3 | TBC1D21 | TSN |
| S100A11 | FOLR1 | ZNF114 | TSNAX |
| SI00P | B4GALT1 | ANO6 | C0L14A1 |
| SLC1A1 | GNAQ | SLC5A9 | WNT5A |
| SLC2A5 | HBB | CRTC2 | ZNF134 |
| SLC12A1 | HBD | C20orf106 | PXDN |
| SLC12A3 | CFH | TMEM192 | SMC1A |
| SNCG | HLA-G | ARMC3 | OFD1 |
| SNRPD1 | HP | NAPEPLD | COPS3 |
| SOD1 | HPR | C10orf30 | STC2 |
| SRI | IGHAl | ATP6V0D2 | ADAM9 |
| TF | IGJ | STXBP4 | CREG1 |
| THBS1 | IGLC1 | C17orf61 | CDK5R2 |
| THY1 | IGLC2 | TXNDC | TNF5F18 |
| TMPRSS2 | IGLC3 | LRRC57 | MPZL1 |
| TSG101 | LAMC1 | H5PA12A | SEMA5A |
| TUBB2A | LPA | MAGI3 | CLDN1 |
| UBE2N | LPL | C11orf47 | RGN |
| UMOD | LRP1 | SLC39A5 | 5LC16A3 |
| UPK2 | LTF | C12orf51 | ARH GEF 1 |
| VTN | TACSTD2 | 5LC46A3 | LRRFIP2 |
| EIF4H | MBL2 | VMO1 | TAAR2 |
| YWHAB | MYH8 | 5LC26A11 | CRIPT |
| YWHAG | NEB | LOC284422 | ENTPD4 |
| YWHAZ | PON1 | CRB2 | IFT140 |
| NPHS2 | PKN2 | HIST2H2AB | RNF40 |
| RAB7A | PROS 1 | FAM151A | RB1CC1 |
| PSCA | MASP1 | 5LC6A19 | PSMD6 |
| CUBN | RELN | PKD1L3 | MRC2 |
| BBOX1 | PTX3 | L0C342897 | HDAC5 |
| RAB11A | RARS | EGFL11 | RASA4 |
| NAPA | SILV | SERINC2 | SLC25A13 |
| PROM1 | THBS2 | PDDC1 | PSMD14 |
| FCGBP | TLR2 | SLCO4C1 | TFG |
| CPNE3 | TTN | SFT2D2 | CDIPT |
| MGAM | TTR | C9orf169 | CRTAP |
| GPRC5A | TYRP1 | LOC377711 | UNC13B |
| RAB11B | VWF | OR11L1 | ARL6IP5 |
| VAMP3 | CLIP2 | RAB19 | TGOLN2 |
| SLC9A3R1 | XDH | LOC440335 | POSTN |
| ITM2B | APOL1 | HIST2H2BF | CLPX |
| NAPSA | FCN3 | LOC441241 | TSPAN9 |
| VPS4B | SELENBP1 | KPRP | TMED10 |
| RAB3D | SMC3 | HSP90AB6P | SLC38A3 |
| PRDX6 | DDX21 | LOC643751 | IL1RAPL1 |
| KIAA0174 | CCPG1 | LOC651536 | GALNT5 |
| PDCD6 | ABCG2 | LOC652968 | PRR4 |
| ARPC4 | SFI1 | AEBP1 | ITGA11 |
| TSPAN1 | MVP | AMY1A | CLASP2 |
| PDZK1IP1 | AKAP9 | AMY1B | EPB41L3 |
| NUTF2 | PRG4 | AMY1C | KIAA0467 |
| FLOT1 | AKR1A1 | AMY2A | DULLARD |
| HRSP12 | ABCA7 | ANGPT1 | NOM01 |
| A2M | COLEC10 | APLP2 | KIAA0146 |
| ACP1 | GNB5 | APP | SLC39A14 |
| ACTA1 | MMRN1 | AQP5 | DNPEP |
| ACTN4 | CLASP1 | AZGP1 | CA5P14 |
| ACTN1 | SYNE1 | CEACAM1 | STX12 |
| ACTN2 | NIPBL | BMP3 | BRMS1 |
| ADAM10 | CHRDL2 | CA6 | ABI3BP |
| AHCY | HSPB8 | DDR1 | PLEKHG3 |
| ALDH1A1 | ANGPTL4 | CAPNS1 | FBXW8 |
| SLC25A4 | NIN | COL6A2 | GAPDHS |
| SLC25A5 | ZNF571 | COPA | GREM1 |
| SLC25A6 | LRP1B | CPD | DKK3 |
| ANXA1 | CNDP2 | DLD | SRPX2 |
| ANXA2P2 | DNAH7 | ETFA | IGHV3-11 |
| APOA1 | HCN3 | GLUD1 | IGHV3-7 |
| ARHGDIA | EXOC4 | H5D17B10 | IGLV4-3 |
| ARVCF | SNX25 | IMPDH2 | IGLV3-21 |
| | TC2N | HTATIP2 | IGLV1-40 |
| | HAPLN3 | MARVELD2 | ST6GALNAC6 |
| ATP1B1 | CD163L1 | CST4 | COPS4 |
| ATP5A1 | HRNR | CST5 | HERC5 |
| ATP5B | P704P | CTSB | NUSAP1 |
| ATP5I | CD24 | DAG1 | PLUNC |

TABLE 2-continued

Exosome polypeptides

| | | | |
|---|---|---|---|
| ATP5O | COL6A3 | DSG2 | PPME1 |
| B2M | COL15A1 | TOR1A | MBD3 |
| CALM1 | COMT | ECM1 | SLC38A2 |
| CALM2 | CP | EIF4G1 | FAM64A |
| CALM3 | CPN2 | EXT2 | GTPBP2 |
| CANX | CRABP2 | FAT2 | DIRAS2 |
| CAPZA1 | CRK | GP C4 | DCHS2 |
| CD2 | CRYAB | FOLH1 | QPCTL |
| CD247 | CRYM | FUT2 | PARP16 |
| CD 86 | CSE1L | FUT3 | TMEM51 |
| CD37 | CSK | FUT6 | MCM10 |
| CD44 | CSTB | FUT8 | CHST12 |
| CD53 | CTH | GLRX | LYAR |
| CDC42 | CTNS | GPC1 | ODZ3 |
| CDH1 | CT SD | GPX3 | WDR52 |
| CFL1 | CTSG | IGHA2 | ASH1L |
| CFL2 | DDB1 | IGHVa | UNC45A |
| COX4I1 | DDC | IGLa | SLC7A10 |
| COX5B | DDX3X | IVL | PNO1 |
| CLDN3 | DDX5 | KRT12 | CD248 |
| CSPG4 | CFD | LAMA4 | AHRR |
| CSRP1 | DNM2 | LAMB2 | ZBTB4 |
| CST3 | DPYS | LGALS7 | SPTBN1 |
| CTNNA1 | DSC2 | LMAN1 | LGR6 |
| CTNNB1 | DSG3 | LPO | RNF123 |
| NQ01 | ECE1 | LTBP3 | PRDM16 |
| DYNC1H1 | MEGF8 | DNAJB 9 | PARVG |
| EEF1A2 | ELA2 | MEST | RMND5A |
| EFNB1 | SERPINB1 | MGAT1 | FAT4 |
| CTTN | EPHX2 | MGP | F1113197 |
| EPHB4 | FBL | MUC5AC | TREML2 |
| ERBB2 | EVPL | MUC7 | SVEP1 |
| F5 | Fll | NEU1 | OBFC1 |
| FASN | FABP1 | NUCB1 | ZNF614 |
| FKBP1A | ACSL4 | NUCB2 | F1122184 |
| FLNA | FAH | FURIN | DBF4B |
| FLNB | EFEMP1 | PAM | CD276 |
| G6PD | FBP1 | PLG | CMIP |
| GCNT2 | FKBP4 | FXYD3 | ADAMTS12 |
| PDIA3 | FKBP5 | PLOD2 | SPACA1 |
| GSN | FRK | PLTP | VANGL1 |
| HADHA | FTH1 | PON3 | SPRY4 |
| HLA-DMB | FUCA1 | PPP 1CB | HYI |
| HLA-E | GABRB2 | PRELP | FAM108A1 |
| HNRPA2B1 | GALK1 | DNAJC3 | TMEM47 |
| HNRNPH2 | GBE1 | HTRA1 | MYCBPAP |
| HSPA1L | GDF2 | RARRES1 | RAB6C |
| HSPA2 | GFRA1 | SAA1 | FAM71F1 |
| HSPA4 | GK2 | SAA2 | ZNF503 |
| HSPA7 | GLO1 | SEPP 1 | PARP10 |
| HSPA9 | GLUL | SFRP1 | SHANK3 |
| HSP9OAA4P | GM2A | ST3GAL1 | LACRT |
| HSP9OAA2 | GNG5 | SLC5A5 | TRIM41 |
| HSP90AB3P | GOT1 | SLC9A1 | OXNAD1 |
| HSPE1 | GPD1 | SLC20A2 | LDHAL6B |
| HSPG2 | GPM6A | SLPI | L0C92755 |
| ICAM1 | GPT | SRPR | CACNA2D4 |
| ITGA6 | GPX4 | STAU1 | ARHGAP18 |
| ITGA2 | GRB2 | HSPA13 | AHNAK2 |
| ITGAV | GRID1 | TGFBI | RPLPOP2 |
| | GSR | TGM1 | PGLYRP2 |
| ITGB2 | GS S | TGM3 | RAB39B |
| ITGB4 | GS TM2 | YES1 | GYLTL1B |
| JUP | HGD | HIST2H2AA3 | KRT74 |
| CD82 | HINT1 | HIST2H2BE | SLAIN1 |
| KPNB1 | HNMT | GALNT4 | LOC122589 |
| KRT2 | HNRNPL | B4GALT3 | NLRP8 |
| KRT5 | HPD | TNFSF13 | PODN |
| KRT8 | HPX | TNFSF12 | C5orf24 |
| KRT13 | HRG | ANGPTL1 | CD109 |
| KRT14 | DNAJA1 | GCNT3 | TRIM40 |
| KRT15 | HSPB1 | TM9SF2 | GPR112 |
| KRT16 | DNAJB1 | DDX23 | KRT72 |
| KRT18 | CFI | ADAMTS 3 | VTI1A |
| KRT19 | IGF2R | GPR64 | SYT9 |
| LAMP2 | IGFALS | LHFPL2 | KRT80 |
| LGALS4 | IL1RN | ST3GAL6 | CCDC64B |

TABLE 2-continued

Exosome polypeptides

| | | | |
|---|---|---|---|
| LYZ | IRF6 | PRDX4 | ATP8B3 |
| | ITGA1 | MAN1A2 | C1orf84 |
| MFGE8 | EIF6 | OS9 | LOC149501 |
| MMP7 | ITGB8 | MGAT4A | LOC150786 |
| MYH10 | ITIH4 | TWF2 | WDR49 |
| MYL6 | KHK | CLCA4 | NEK10 |
| MY01C | KIFC3 | TXNDC4 | STOML3 |
| MY01D | KLK1 | PLCB1 | SASS6 |
| NME1 | LBP | CES3 | DCLK2 |
| NME2 | LCN2 | B3GAT3 | FREM3 |
| PRDX1 | LCP1 | TOR1B | C9orf91 |
| PCBP1 | LTA4H | IGHV30R16-13 | TREML2P |
| CHMP1A | BCAM | IGLV2-11 | CCDC129 |
| SERPINF1 | MAN2A1 | IGLV1-44 | PAN3 |
| PHB | MDH2 | IGKV3D-15 | MAMDC2 |
| PPIB | MFI2 | IGKV4-1 | RCOR2 |
| PRKAR2A | MLLT3 | C1GALT1C1 | LOC283412 |
| PRKDC | MLLT4 | RACGAP1 | LOC283523 |
| PSMA2 | MNDA | EFEMP 2 | NOM02 |
| QSOX1 | MPO | DUOX2 | SEC14L4 |
| PYGB | MPST | SDF4 | LCN1L1 |
| RAB6A | MY01B | CYB5R1 | LOC286444 |
| RALA | MSRA | ERAP 1 | TAS2R60 |
| RAP1A | MTAP | NUDT9 | KRT18P19 |
| RPL6 | MTHFD1 | FAM3B | LOC343184 |
| RPL8 | MYH3 | FAM20A | LOC345041 |
| RPLP1 | MY05B | FAM55D | GNAT3 |
| RPLP2 | MY06 | ANO1 | POLN |
| RPN1 | NID1 | LRRC16A | LOC376693 |
| RPS3 | NKX6-1 | TTC17 | ARMS2 |
| RPS7 | NQ02 | PDGFC | LOC387867 |
| RPS13 | NP | PCDHGB5 | LOC388339 |
| RPS14 | NPC1 | CCL28 | FLG2 |
| RPS15A | NPHS1 | UGCGL1 | LOC388707 |
| RPS18 | NRF1 | SEMA3G | LOC389141 |
| RPS20 | NT5E | CORO1B | LOC390183 |
| RPS21 | PAFAH1B1 | NDRG2 | KRT8P9 |
| RPS27A | PAFAH1B2 | KIAA1324 | LOC391777 |
| RRAS | PCBD1 | TXNDC16 | LOC391833 |
| S100A10 | PCK1 | ARH GAP 23 | LOC399942 |
| SDC1 | PDCD2 | MUTED | LOC400389 |
| SDC4 | PDE8A | TINAGL1 | LOC400578 |
| SLC1A5 | ENPP3 | TOR3A | LOC400750 |
| SLC2A1 | SLC26A4 | VWA1 | LOC400963 |
| PDZK1 | CHID1 | F1121767 | |
| SLC12A2 | PEPD | TMEM109 | LOC401817 |
| SLC16A1 | PFKL | GAL3S T4 | NOM03 |
| SPTBN1 | PGD | THSD4 | LOC439953 |
| SSBP1 | PGM1 | UXS1 | RPL12P6 |
| SSR4 | SLC25A3 | TXND C5 | LOC440589 |
| TBCA | SERPINA4 | CRISPLD1 | LOC440917 |
| TCEB1 | SERPINB6 | LOXL1 | LOC440991 |
| TFRC | SERPINB13 | GNPTG | LOC441876 |
| TKT | PIK3C2A | SCGB3A1 | LOC442308 |
| TSPAN8 | PIP | CHST14 | DIPAS |
| TPM1 | PKD2 | C1QTNF1 | LOC643300 |
| HSP90B1 | PKLR | C1QTNF3 | LOC643358 |
| TUBA4A | PKHD1 | SLC26A9 | LOC643531 |
| TUFM | PLCD1 | FAM129A | RPSAP8 |
| TXN | PLOD1 | HIST2H3C | LOC644464 |
| UBA52 | PLS1 | TPRG1L | LOC644745 |
| UBB | UBL3 | TMPRSS11B | LOC645018 |
| UBC | PPL | C20orf70 | LOC645548 |
| UBA1 | PPP1R7 | PPM1L | LOC646127 |
| UBE2V2 | PRCP | GBP6 | LOC646316 |
| UGDH | PRKCA | KRT78 | LOC646359 |
| UQCRC2 | PRKCD | SLC37A2 | LOC646785 |
| VCP | PRKCH | NPNT | LOC646875 |
| VIL1 | PRKCI | KRT73 | LOC646949 |
| YWHAH | PRKCZ | HIST2H3A | LOC647000 |
| CXCR4 | PRNP | VWA2 | LOC647285 |
| SLC7A5 | PRSS8 | GSTK1 | LOC650405 |
| HIST1H4I | PRTN3 | SBSN | LOC650901 |
| HIST1H4A | PSMA1 | C5 orf46 | LOC652493 |
| HIST1H4D | PSMA3 | LRRC26 | LOC652797 |
| HIST1H4F | PSMA4 | C4orf40 | LOC653162 |
| HIST1H4K | PSMA5 | L0C440786 | PPIAL3 |
| HIST1H4J | PSMB1 | SCFV | LOC653232 |
| HIST1H4C | PSMB2 | LGALS7B | HSPBL2 |
| HIST1H4H | PSMB5 | HIST2H3D | LOC728002 |
| HIST1H4B | PSMB6 | ACAT2 | LOC728088 |
| HIST1H4E | PSMC5 | ACTL6A | LOC728576 |
| HIST1H4L | PSMD12 | ADK | LOC728590 |
| HIST2H4A | PSME2 | ANXA8L2 | LOC728791 |
| | TAGLN2 | PTPN6 | LOC728979 |
| | RUVBL1 | PTPN13 | ANG |
| | VAMP8 | PTPRO | BDNF |
| SNAP23 | QDPR | CAV1 | CALU |
| IQGAP1 | RAB27A | CD70 | CCR4 |
| KRT75 | RAP1GDS1 | CS | CCR5 |
| TJP2 | RBL2 | DARS | C5F2 |
| ROCK2 | RBP4 | DHX9 | C5F3 |
| ARPC3 | RENBP | DPYSL2 | DCN |
| ACTR3 | RFC1 | EEF1D | EPO |
| LRPPRC | RHEB | EPRS | F3 |
| TRAP1 | RNH1 | FDPS | GPC5 |
| TUBB4 | RNPEP | FLNC | GDF1 |
| GNB2L1 | ROB02 | XRCC6 | GDF9 |
| BAIAP2 | RP2 | GFPT1 | GFRA3 |
| HYOU1 | RP511 | HIST1H1B | GRN |
| AGR2 | RREB1 | HIST1H2BB | CXCL2 |
| OLFM4 | RYR1 | H3F3A | GZMA |
| CCT2 | S100A4 | H3F3B | HIST1H2BD |
| ATP5L | S100A8 | HNRNPF | HGF |
| CCT8 | S100A9 | HNRNPK | IFNG |
| SLC12A7 | SERPINB4 | IARS | IGFBP3 |
| MASP2 | SCN10A | LAMA3 | IGFBP4 |
| IQGAP2 | SEC13 | LAMB3 | IGFBP6 |
| RAB10 | SECTM1 | LAMC2 | IGFBP7 |
| PRDX3 | SH3BGRL | LGAL51 | IL1RAP |
| EHD1 | 5HMT1 | NBR1 | IL3 |
| TMED2 | SHMT2 | MARS | IL5 |
| LMAN2 | SLC3A1 | MX1 | IL6ST |
| YWHAQ | SLC4A1 | PFKP | IL7 |
| GCN1L1 | SLC5A1 | PLAU | IL8 |
| RAB35 | SLC5A2 | PSMB4 | IL10 |
| DSTN | SLC6A13 | PSMC2 | IL11 |
| UPK1A | SLC9A3 | PSMC4 | IL13 |
| PHB2 | SLC15A2 | PSMD2 | IL15RA |
| RRAS2 | SLC25A1 | PSMD13 | INHBA |
| SEC31A | SLC22A2 | PYGL | INHBB |
| CLSTN1 | SLC22A5 | RPL10 | IP05 |
| PTGR1 | SMO | RPL15 | LIF |
| RAB21 | SORD | STX4 | LRP6 |
| CYFIP1 | SORL1 | TARS | LTBP1 |
| SLC44A1 | SPAST | CLDN5 | MMP1 |
| CORO1C | SPR | TPBG | MMP2 |
| MTCH2 | SPRR3 | XPO1 | MMP3 |
| QPCT | SRC | XRCC5 | MMP10 |
| PRDX5 | ST13 | BAT1 | NBL1 |
| SND1 | STK11 | HIST1H2BG | TNFRSF11B |
| FUR | VAMP7 | HIST1H2BF | OSM |
| LIMA1 | SYPL1 | HIST1H2BE | PDGFA |
| RAB6B | SERPINA7 | HIST1H2BI | PRKCSH |
| KRT20 | TECTA | HIST1H2BC | CCL2 |
| VPS35 | TGM4 | HIST1H4G | CCL7 |
| TOMM22 | TGFBR3 | EIF3A | CCL20 |
| AKR1B10 | TGM2 | EIF3B | SFRP4 |
| 5100A14 | TLN1 | EIF3C | 50D3 |
| DIP2B | DNAJC7 | SLC5A6 | SPARC |
| RAP2C | UBE2G1 | HIST2H2AA4 | TIMP1 |
| FAM129B | UPK1B | LOC728358 | TIMP2 |
| | UGP2 | LOC730839 | TIMP3 |
| AHNAK | UPK3A | LOC100126583 | ICAM5 |
| VPS37B | UTRN | AARS | TNFRSF1A |
| TUBA4B | VASP | AK2 | VEGFC |
| ARPC5L | VCL | APEH | GDF5 |
| EPPK1 | VDAC1 | FAS | HIST3H3 |
| ADSL | VDAC3 | BAX | HIST1H2AI |
| AP2A1 | XPNPEP2 | FMNL1 | HIST1H2AL |
| RHOC | BTG2 | CASP9 | HIST1H2AC |
| RHOG | GCS1 | CD19 | HIST1H2AM |
| ASNS | BAT2 | M54A1 | HIST1H2BN |
| | PTP4A2 | CD22 | HIST1H2BM |
| CAD | DYSF | TNFRSF8 | HIST1H2BH |
| CBR1 | EEA1 | SCARB1 | HIST1H2B0 |

TABLE 2-continued

Exosome polypeptides

| | | | | | | | |
|---|---|---|---|---|---|---|---|
| CBR3 | STK24 | ENTPD1 | HIST1H3A | KRT3 | TRIP10 | MRLC2 | LOC440093 |
| CCT6A | CUL4B | CD48 | HIST1H3D | KRT4 | SLC9A3R2 | PAGE2 | PGAM4 |
| CDH17 | CUL3 | CD58 | HIST1H3C | KRT6A | SLIT2 | HIST1H2BA | PC-3 |
| CEACAM5 | ATRN | CD74 | HIST1H3E | KRT6B | SLC22A6 | SNX33 | LOC729500 |
| COPB1 | CDC42BPA | CD79B | HIST1H3I | KRT7 | KL | PTRF | KRT18P26 |
| CLDN4 | PPFIA2 | CD97 | HIST1H3G | KRT17 | KIF3B | HIST2H2BC | S100A11P |
| CLDN7 | AKR7A2 | 41889 | HIST1H3J | RPSA | SLC22A8 | ANXA8 | LOC729679 |
| CRYZ | PPAP2A | CR2 | HIST1H3H | LFNG | GRHPR | NME1-NME2 | KRT17P3 |
| CD55 | ABCB11 | CSNK2B | HIST1H3B | LGALS3 | SLC22A13 | EIF2S1 | RCTPI1 |
| EEF1G | MAP2K1IP1 | DBI | FADD | LRP4 | TMPRSS11D | EIF2S3 | LOC729903 |
| EPHA2 | EIF3H | DHCR7 | IL1RL2 | CD46 | GSTO1 | EIF4E | RP11-556K13.1 |
| EIF4A1 | SLC4A4 | DLG1 | FGF18 | MICA | NPEPPS | EPB41L2 | LOC100129982 |
| EIF4A2 | SNX3 | DOCK2 | FGF16 | MYH11 | TMEM59 | EVI2B | LOC100130100 |
| ENO2 | MYH13 | DUT | HIST1H3F | NARS | ATP6V1G1 | FCER2 | LOC100130446 |
| SLC29A1 | NAPG | ECH1 | HIST1H2AG | NEDD4 | CDC42BPB | FGR | LOC100130562 |
| EPHB2 | FBP2 | VAPA | HIST1H2BJ | RPL10A | CREB5 | FH | LOC100130624 |
| EPHB3 | SCEL | H2AFY | NRG2 | PCNA | CROCC | GART | LOC100130711 |
| ESD | SUCLA2 | PDIA4 | GDF3 | PLEC1 | DHX34 | GOT2 | LOC100130819 |
| F7 | GGH | EIF4A3 | FGF19 | PLXNA1 | TMEM63A | NCKAP1L | LOC100131713 |
| FLOT2 | PROZ | ACTR1B | GDF11 | PPP2R1A | SLK | HLA-DPB1 | LOC100131863 |
| GARS | SQSTM1 | OPTN | FST | PSMC6 | RUSC2 | HLA-DQA1 | LOC100132795 |
| GMDS | AP1M1 | NAMPT | LASS1 | PSMD3 | OXSR1 | HNRNPA1 | LOC100133211 |
| GNB3 | RAB7L1 | MPZL2 | HPSE | PSMD11 | SLC23A1 | HNRNPC | LOC100133690 |
| HIST1H2AE | WASL | STIP1 | ESM1 | RAC3 | DOPEY2 | HPRT1 | SET |
| HLA-C | PLOD3 | PKP3 | DKK1 | RAP2A | ABI1 | ICAM3 | CCT6B |
| HLA-H | PGLYRP1 | POFUT2 | IL17B | RAP2B | GNPDA1 | INSR | ACTR3B |
| HPCAL1 | KALRN | QPRT | IL19 | RPL12 | TOM1 | EIF3E | PSMA8 |
| | CLIC3 | WBP2 | TNFRSF12A | RPLP0 | ABCB6 | ITGAL | ARP11 |
| IGHα | BAZ1B | ERO1L | IL23A | RPS4X | ABCC9 | ITGB3 | BCHE |
| IGHG1 | SPAG9 | H2AFY2 | FGFRL1 | RPS4Y1 | HUWE1 | ITGB7 | H2AFZ |
| IGHG2 | SLC13A2 | RCC2 | TREM1 | RPS8 | ARPC5 | IT1H2 | SNRPE |
| IGHG3 | ATP6V0D1 | RTN4 | IL1F9 | RPS16 | ACTR2 | STMN1 | TFPI |
| IGHG4 | HGS | GLT25D1 | CXCL16 | SPTAN1 | TSPAN3 | LCK | ADAMTS1 |
| IGHM | AP4M1 | RNASE7 | IL22RA1 | VAMP1 | ARPC2 | LSP1 | GDF15 |
| IGKC | ATP6V1F | FCRLA | HIST1H2BK | | | | |
| ITGA3 | PTER | H2AFV | HIST3H2BB | | | | |

TABLE 3

Polypeptide payloads and receivers

| Ankyrin repeat proteins | Fibronectins | Lyases | |
|---|---|---|---|
| General Classes | | | |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratricopeptide repeat proteins |
| Complement | | | |
| C1 inhibitor | C4 binding protein | CR3 | Factor I |
| C3 Beta chain Receptor | CD59 | CR4 | Homologous restriction factor |
| C3aR | CR1 | Decay-accelerating factor (DAF) | Membrane cofactor protein (MCP) |
| C3eR | CR2 | Factor H | PRELP |
| Enzymes | | | |
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycero phosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |

TABLE 3-continued

Polypeptide payloads and receivers

| Ankyrin repeat proteins | | Fibronectins | Lyases |
|---|---|---|---|
| 1,4-lactonase | carboxymethylenebuten olidase | fusarinine-C ornithinesterase | phosphoglycerate phosphatase |
| 11-cis-retinyl-palmitate hydrolase | cellulose-polysulfatase | galactolipase | phosphoglycolate phosphatase |
| 1-alkyl-2-acetylglycerophosp hocholine esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3', 5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacetaldehyde hydrolase |
| 3-oxoadipate enol-lactonase | choline-sulfatase | glycerophosphocholine phosphodiesterase | phosphonoacetate hydrolase |
| 3-phytase | choloyl-CoA hydrolase | Glycosidases, i.e. enzymes that hydrolyse O- and S-glycosyl compounds | phosphonopyruvate hydrolase |
| 4-hydroxybenzoyl-CoA | chondro-4-sulfatase thioesterase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol- | Phosphoric-monoester phosphatase hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxyacylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase CoA hydrolase | hydroxymethylglutaryl-methylesterase | protein-glutamate |
| acetoacetyl-CoA hydrolase | deoxylimonate A-ring-lactonase | iduronate-2-sulfatase | quorum-quenching N-acyl-homoserine lactonase |
| acetoxybutynylbithiophene deacetylase | dGTPase | inositol-phosphate phosphatase | retinyl-palmitate esterase |
| acetylajmaline esterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolaminephosphate phosphodiesterase |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoy[acyl-carrier-protein hydrolase | lysophospholipase | sinapine esterase |

TABLE 3-continued

Polypeptide payloads and receivers

| Ankyrin repeat proteins | | Fibronectins | Lyases |
|---|---|---|---|
| acetylxylan esterase | Endodeoxyribonucleases producing 3'-phosphomonoesters | mannitol-1-phosphatase | Site specific endodeoxyribonucleases: cleavage is not sequence specific |
| acid phosphatase | Endodeoxyribonuclease producing 5'-phosphomonoesters | Metallocarboxypeptidases | Site-specific endodeoxyribonucle that are specific for altered bases. |
| Acting on acid anhydrides to catalyse transmembrane movement of substances | Endopeptidases of unknown catalytic mechanism | Metalloendopeptidases. | Site-specific endodeoxyribonucleases: cleavage is sequence specific |
| Acting on acid anhydrides to facilitate cellular and subcellular movement | Endoribonucleases producing 3'-phosphomonoesters | methylphosphothioglycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosaminoglycan deacetylase | succinyl-CoA hydrolase |
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |
| Adenosine deaminase | Enzymes acting on peptide bonds (peptidases) | oxaloacetase | Thioether and trialkylsulfonium hydrolases |
| adenylyl-[glutamate—ammonia ligase hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |

TABLE 3-continued

Polypeptide payloads and receivers

| Ankyrin repeat proteins | | Fibronectins | Lyases |
|---|---|---|---|
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters. | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| | b-diketone hydrolase | phorbol-diester hydrolase | xylono-1,4-lactonase |

TABLE 4

Targets

General Classes of Targets

| | | | |
|---|---|---|---|
| Microbes | Polypeptides | DNA | Amino Acids |
| Fungi | Toxins | RNA | Prions |
| Bacteria | Lipids | Parasites | Cytokines |
| Virus | Cells | Cellular Debris | |

Infectious Disease-Related Targets

| | | | |
|---|---|---|---|
| Lipopolysaccharides | Cell invasion protein | Intermedilysin | Secreted effector protein sptP |
| Zona occludens toxin | Cholera enterotoxin | Invasion protein sipA | Seeligeriolysin |
| Actin polymerization protein RickA | Cysteine protease | Iota toxin component Ia | Serine protease |
| Actin polymerization protein RickA | Cytolethal distending toxin | Ivanolysin | Shiga toxin |
| Adenosine monophosphate-protein transferase vopS | Cytolysin | LepB | Sphingomy elinase |
| adenylate cyclase | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |

TABLE 4-continued

| Targets | | | |
|---|---|---|---|
| Binary ADP-ribosyltransferase CDT toxin | Exotoxin | Plasminogen activator | TolC |
| Botulinum neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |

| Lipid & Cell Targets | | | |
|---|---|---|---|
| Circulating tumor cells | very low density lipid (VLDL) | Triglycerides | Fatty acids |
| Metastases | high density lipoprotein | Chylomicrons | Cholesterol |
| Eukaryotic cells | low density lipoprotein | Apolipoproteins | |

TABLE 5

| Cancers | | | |
|---|---|---|---|
| Acute lymphoblastic leukaemia (ALL) | Colorectal cancer | Macroglobulinemia, Waldenstrom | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |
| Basal Cell Carcinoma | Esthesioneuroblastoma, Childhood | Mouth and oropharyngeal cancer | Rhabdomyosarcoma |
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sézary Syndrome |
| Brain Stem Glioma, Childhood | Gallbladder Cancer | Myelodysplastic/Myelo proliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |
| Bronchial Tumors, Childhood | Germ Cell Tumor Cancer | Nasopharyngeal cancer | Small Intestine |
| Burkitt Lymphoma | Gestational trophoblastic tumours (GTT) | Neuroblastoma | Soft Tissue Sarcoma |

TABLE 5-continued

| Cancers | | | |
|---|---|---|---|
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |
| Cancer spread to brain | Head and neck cancer Cancer | Oesophageal cancer | Stomach (Gastric) |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutaneous - see Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenstrom Macroglobulinemia |
| Lymphoma | Lung Cancer | Plasma Cell Neoplasm/Multiple Myeloma | WilmsTumor |

The present invention has been described with respect to representative examples that are to be considered illustrative embodiments that do not limit the scope of the invention which is defined solely by the claims. All references to publications, including scientific publications, treatises, textbooks, patent applications and issued patents are hereby incorporated by reference for all purposes.

The invention claimed is:

1. An extracellular vesicle comprising a single-stranded antisense oligonucleotide (ASO) that inhibits KRAS, wherein the ASO comprises a sequence having at least about 95% sequence identity to the sequence set forth in SEQ ID NO: 6.

2. The extracellular vesicle of claim 1, wherein the extracellular vesicle is an exosome.

3. The extracellular vesicle of claim 1, wherein the ASO comprises the sequence set forth in SEQ ID NO: 6.

4. The extracellular vesicle of claim 3, further comprising an additional immunomodulating component.

5. The extracellular vesicle of claim 4, wherein the additional immunomodulating component is a small molecule drug, an antibody or active fragment thereof, or a therapeutic protein or active fragment thereof.

6. The extracellular vesicle of claim 5, wherein the antibody or active fragment thereof is an immune checkpoint inhibitor that binds to CTLA-4, PD-1, or PD-L1 or an inhibitor that binds to CSF1-R.

7. The extracellular vesicle of claim 6, wherein the antibody or active fragment thereof comprises CDRs that are at least 95% identical to the CDRs of Ipilimumab, or at least 95% identical to the CDRs of Nivolumab, or at least 95% identical to the CDRs of Cemiplimab, or at least 95% identical to the CDRs of Pembrolizumab, or at least 95% identical to the CDRs of Atezolizumab, or at least 95% identical to the CDRs of Avelumab, or at least 95% identical to the CDRs of Durvalumab, or at least 95% identical to the CDRs of Pexidartinib, or at least 95% identical to the CDRs of PLX7486, or at least 95% identical to the CDRs of ARRY-382, or at least 95% identical to the CDRs of JNJ-40346527, or at least 95% identical to the CDRs of BLZ945, or at least 95% identical to the CDRs of Emactuzumab, or at least 95% identical to the CDRs of AMG820, or at least 95% identical to the CDRs of IMC-CS4, or at least 95% identical to the CDRs of Cabiralizumab; or wherein the antibody or active fragment thereof is at least one antibody selected from the group consisting of Ipilimumab, Nivolumab, Cemiplimab, Pembrolizumab, Atezolizumab, Avelumab, Durvalumab, Pexidartinib, PLX7486, ARRY-382, JNJ-40346527, BLZ945, Emactuzumab, AMG820, IMC-CS4 and Cabiralizumab.

8. The extracellular vesicle of claim 5, further comprising PTGFRN or a fragment thereof, wherein the antibody or fragment thereof is fused to the PTGFRN or fragment thereof.

9. A pharmaceutical composition comprising the extracellular vesicle of claim 1.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 1
taagctgata attcaactca                                                    20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tgagcgaatg gacaggtctt                                                    20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
tggatttaaa ggcaggcggc                                                    20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ttgggtaaag tcgtgcagca                                                    20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gtgcagtatt gtagccaggc                                                    20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
gtagcatgta aatatagccc                                                    20
```